United States Patent
Keene et al.

(10) Patent No.: US 9,738,670 B2
(45) Date of Patent: Aug. 22, 2017

(54) PENTAAZA MACROCYCLIC RING COMPLEXES POSSESSING ORAL BIOAVAILABILITY

(71) Applicant: Galera Labs, LLC, Creve Coeur, MO (US)

(72) Inventors: Jeffery L. Keene, St. Louis, MO (US); Otto F. Schall, Creve Coeur, MO (US); Dennis P. Riley, Chesterfield, MO (US)

(73) Assignee: Galera Labs, LLC, Creve Coeur, MO (US)

( * ) Notice: Subject to any disclaimer, the term of this patent is extended or adjusted under 35 U.S.C. 154(b) by 0 days.

(21) Appl. No.: 15/246,830

(22) Filed: Aug. 25, 2016

(65) Prior Publication Data
US 2017/0042907 A1    Feb. 16, 2017

Related U.S. Application Data

(63) Continuation of application No. PCT/US2016/046599, filed on Aug. 11, 2016.

(60) Provisional application No. 62/203,761, filed on Aug. 11, 2015.

(51) Int. Cl.

| | | |
|---|---|---|
| C07F 13/00 | (2006.01) |
| A61K 31/28 | (2006.01) |
| A61K 9/28 | (2006.01) |
| A61K 9/48 | (2006.01) |
| A61K 31/555 | (2006.01) |
| A61K 47/38 | (2006.01) |
| A61K 47/44 | (2017.01) |
| A61K 9/00 | (2006.01) |
| A61K 47/14 | (2017.01) |

(52) U.S. Cl.
CPC .......... *C07F 13/005* (2013.01); *A61K 9/0019* (2013.01); *A61K 9/2866* (2013.01); *A61K 9/4816* (2013.01); *A61K 31/28* (2013.01); *A61K 31/555* (2013.01); *A61K 47/14* (2013.01); *A61K 47/38* (2013.01); *A61K 47/44* (2013.01)

(58) Field of Classification Search
CPC .... A61K 31/555; A61K 31/28; A61K 9/0053; C07F 13/005
See application file for complete search history.

(56) References Cited

U.S. PATENT DOCUMENTS

| | | | |
|---|---|---|---|
| 5,874,421 A | 2/1999 | Riley et al. | |
| 6,180,620 B1 | 1/2001 | Salvemini | |
| 6,214,817 B1 * | 4/2001 | Riley | A61K 31/555 514/183 |
| 8,263,568 B2 * | 9/2012 | Slomczynska | G01N 30/96 514/43 |
| 8,444,856 B2 | 5/2013 | Slomczynska et al. | |

FOREIGN PATENT DOCUMENTS

| | | | |
|---|---|---|---|
| WO | 9302090 | 2/1993 | |
| WO | 9415925 | 7/1994 | |
| WO | 9639396 | 12/1996 | |
| WO | 02071054 | 9/2002 | |
| WO | WO 02071054 A1 * | 9/2002 | ............ G01N 30/34 |
| WO | 2006083508 | 8/2006 | |
| WO | 2009143454 | 11/2009 | |
| WO | WO 2009143454 A2 * | 11/2009 | ............ A61K 31/28 |

OTHER PUBLICATIONS

Strickley, R.G. "Solubilizing Excipients in Oral and Injectable Formulations" Pharmaceutical Research, vol. 21, No. 2, Feb. 2004, pp. 201-230.*
Hussan, S.D., et al. "A review on recent advances of enteric coating" J Pharm, Nov.-Dec. 2012, 2 (6), 5-11.*
Cuzzocrea et al., C. Tempol, a membrane-permeable radical scavenger, reduces dinitrobenzene sulfonic acid-induced colitis, Eur J Pharmacol., 2000, 406:127-137 2001.
Murphy et al., Efficacy of superoxide dismutase mimetic M40403 in attenuating radiation-induced oral mucosisis in hamsters, Clin. Can. Res., 2008, 14(13):4292-4297 2008.
Thompson et al., The manganese superoxide dismutase mimetic, M40403, protects adult mice from lethal total body irradiation, Free Radical Research, 2010; 44(5): 529-540.

(Continued)

*Primary Examiner* — Timothy Thomas
*Assistant Examiner* — Andrew S Rosenthal
(74) *Attorney, Agent, or Firm* — Bryan Cave LLP

(57) ABSTRACT

Aspects of the present disclosure relate to compounds which have enhanced oral bioavailability. A transition metal complex includes a transition metal coordinated by a macrocycle comprising the pentaaza 15-membered macrocyclic ring corresponding to Formula A and two axial ligands having the formula $-OC(O)X_1$.

FORMULA A

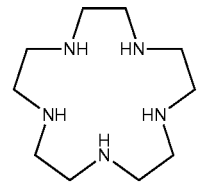

each of the two axial ligands has the formula $-OC(=O)X_1$ wherein each $X_1$ is independently substituted or unsubstituted phenyl or $-C(-X_2)(-X_3)(-X_4)$;
each $X_2$ is independently substituted or unsubstituted phenyl, or substituted or unsubstituted alkyl;
each $X_3$ is independently hydrogen, hydroxyl, alkyl, amino, $-X_5C(=O)R_{13}$ where $X_5$ is NH or O, and $R_{13}$ is $C_1$-$C_{18}$ alkyl, substituted or unsubstituted aryl or $C_1$-$C_{18}$ aralkyl, or $-OR_{14}$, where $R_{14}$ is $C_1$-$C_{18}$ alkyl, substituted or unsubstituted aryl or $C_1$-$C_{18}$ aralkyl, or together with $X_4$ is $(=O)$; and
each $X_4$ is independently hydrogen or together with $X_3$ is $(=O)$.

8 Claims, 12 Drawing Sheets

(56) References Cited

OTHER PUBLICATIONS

Tuder et al., Oxidative Stress and Apoptosis Interact and Cause Emphysema Due to Vascular Endothelial Growth Factor Receptor Blockade, Am. J. Respir. Cell Mol. Biol., 2003, 29: 88-97.
Salvemini et al., A nonpeptidyl mimic of superoxide dismutase with therapeutic activity in rats, Science, 1999, 286: 304-306.
Salvemini et al., Amelioration of Joint Disease in a Rat Model of Collagen-Induced Arthritis by M40403, a Superoxide Dismutase Mimetic, Arthritis & Rheumatism, 2001, 44: 2909-2921 2001.
Goodman & Gilman's The Pharmacological Basis of Therapeutics, 10th Edition, McGraw Hill, 1996 1996.
Aston et al., Computer-Aided Design (CAD) of Mn(II) Complexes: Superoxide Dismutase Mimetics with Catalytic Activity Exceeding the Native Enzyme, Inorg. Chem., 2001, 40: 1779-1789.
Suenderhauf et al., A Physiologically Based Pharmacokinetic Model of the Minipig: Data Compilation and Model Implementation, Pharm. Res., 2013, 30(1): 1-15 2013.
Cuzzocrea et al., Protective effects of M40401, a selective superoxide dismutase mimetic, on zymosan-induced nonseptic shock, Crit. Care Med., 2004, 21(1): 157-167 2004.
Cuzzocrea et al., Reduction in the development of Cerulein-induced acute pancreatitis by treatment with M40401, a new selective superoxide dismutase mimetic, Shock, 2004, 22(3): 254-261 2004.
Anderson, C., Phase 1 Trial of Superoxide Dismutase (SOD) Mimetic GC4419 to Reduce Chemoradiotherapy (CRT)-Induced Mucositis (OM) in Patients (pts) with Mouth or Oropharyngeal Carcinoma (OCC), Oral Mucositis Research Workshop, MASCC/ISOO Annual Meeting on Supportive Care in Cancer, Copenhagen, Denmark (Jun. 25, 2015) 2015.
Cotton et al., Advanced Inorganic Chemistry, Chapter 5, "Coordination Compounds", 2nd revised edn., Interscience Publishers, 1966, 139 1966.
Cotton et al., Advanced Inorganic Chemistry, Chapter 2, "Coordination Compounds", 2nd revised edn., Interscience Publishers, 1966, 35-36, 45-49 1966.
Wang et al., Evidence of d-phenylglycine as delivering tool for improving I-dopa absorption, J. Biomed. Sci., 2010, 17: 71-79 2010.
Wikipedia, Cefalexin, retrieved Nov. 2, 2016, from en.wikipedia.org/wiki/Cefalexin, 6 pages 2016.
Strickley, R. G., Solubilizing Excipience in Oral and Injectable Formulations, Pharmaceutical Research, 2004, 21 (2): 201-230 2004.
Hussan et al., A review on recent advances of enteric coating, Journal of Pharmacy, 2012, 2(6): 5-11 2012.
Patent Cooperation Treaty, International Search Report for PCT/US2016/046599, dated Nov. 17, 2016, 5 pages Nov. 17, 2016.

\* cited by examiner

| | | |
|---|---|---|
|  |  | Phenylacetate |
|  |  | Mandelate |
|  |  | Phenylglycine |
|  |  | Phenlglyoxylate |
|  |  | 2-Phenylpropionate |
| $R_1 = CH_3$ | $R_2 = R_3 = H$ | Propionate |
| $R_1 = CH_3$ | $R_2 = OH, R_3 = H$ | Lactate |

PENTAAZA MACROCYCLIC RING COMPLEXES POSSESSING ORAL BIOAVAILABILITY

The present disclosure generally relates to transition metal pentaaza 15-membered macrocyclic ring complexes which have improved properties, including significant oral bioavailability.

Transition metal pentaaza 15-membered macrocyclic ring complexes having the macrocyclic ring system corresponding to Formula A have been shown to be effective in a number of animal and cell models of human disease, as well as in treatment of conditions afflicting human patients.

FORMULA A

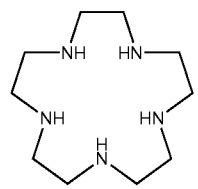

For example, in a rodent model of colitis, one such compound, GC4403, has been reported when administered by intraperitoneal (ip) injection to significantly reduce the injury to the colon of rats subjected to an experimental model of colitis (see Cuzzocrea et al., *Europ. J. Pharmacol.*, 432, 79-89 (2001)).

GC4403

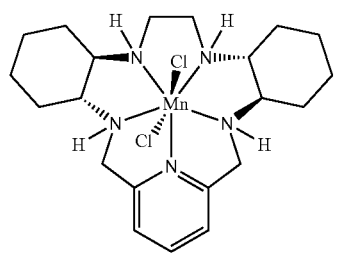

GC4403 administered ip has also been reported to attenuate the radiation damage arising both in a clinically relevant hamster model of acute, radiation-induced oral mucositis (Murphy et al., *Clin. Can. Res.*, 14(13), 4292 (2008)), and lethal total body irradiation of adult mice (Thompson et al., *Free Radical Res.*, 44(5), 529-40 (2010)). Similarly, another such compound, GC4419, administered ip has been shown to attenuate VEGFr inhibitor-induced pulmonary disease in a rat model (Tuder, et al. *Am. J. Respir. Cell Mol. Biol.*, 29, 88-97 (2003)), and to increase the anti-tumor activity of anti-metabolite and anti-mitotic agents in mouse cancer models (see, e.g., WO2009/143454). Additionally, another such compound, GC4401, administered ip has been shown to provide protective effects in animal models of septic shock (S. Cuzzocrea, et. al., *Crit. Care Med.*, 32(1), 157 (2004) and pancreatitis (S. Cuzzocrea, et. al., *Shock*, 22(3), 254-61 (2004)).

GC4419

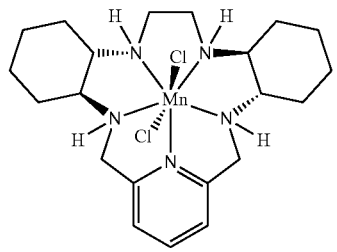

GC4401

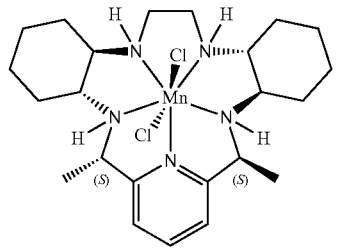

Certain of these compounds have also been shown to possess potent anti-inflammatory activity and prevent oxidative damage in vivo. For example, GC4403 administered ip has been reported to inhibit inflammation in a rat model of inflammation (Salvemini, et. al., *Science*, 286, 304 (1999)), and prevent joint disease in a rat model of collagen-induced arthritis (Salvemini et al., *Arthritis & Rheumatism*, 44(12), 2009-2021 (2001)). In addition, these compounds have been reported to possess analgesic activity and to reduce inflammation and edema in the rat-paw carrageenan hyperalgesia model, see, e.g., U.S. Pat. No. 6,180,620.

Compounds of this class have also been shown to be safe and effective in the prevention and treatment of disease in human subjects. For example, GC4419 administered by intravenous (iv) infusion has been shown to reduce oral mucositis in head-and-neck cancer patients undergoing chemoradiation therapy (Anderson, C., *Phase 1 Trial of Superoxide Dismutase (SOD) Mimetic GC4419 to Reduce Chemoradiotherapy (CRT)-Induced Mucositis (OM) in Patients (pts) with Mouth or Oropharyngeal Carcinoma (OCC)*, Oral Mucositis Research Workshop, MASCC/ISOO Annual Meeting on Supportive Care in Cancer, Copenhagen, Denmark (Jun. 25, 2015)).

In each of these compounds comprising the pentaaza 15-membered macrocyclic ring of Formula A, the five nitrogens contained in the macrocyclic ring each form a coordinate covalent bond with the manganese (or other transition metal coordinated by the macrocycle) at the center of the molecule. Additionally, manganese (or other appropriate transition metal coordinated with the macrocycle) forms coordinate covalent bonds with "axial ligands" in positions perpendicular to the roughly planar macrocycle. Such coordinate covalent bonds are characterized by an available "free" electron pair on a ligand forming a bond to a transition metal via donation and sharing of the electron pair thus forming a two-electron bond between the metal and the donor atom of the ligand (Cotton, F. A. & G. Wilkinson, *Advanced Inorganic Chemistry*, Chapter 5, "Coordination Compounds", 2$^{nd}$ revised edn., Interscience Publishers, p. 139 (1966); IUPAC Gold Book, online version http://goldbook.iupac.org/C01329.html). The coordinate covalent nature of the bonds between manganese (or other such appropriate transition metal) and the five macrocyclic ring nitrogens and between manganese (or other such transition metal) and each of the two chloro axial ligands is evidenced, for example, by the "single crystal" X-ray crystal structure of GC4403 (FIG. 11) and GC4419 (FIG. 12).

Coordination compounds contrast with ionic compounds, for example, salts, where in the solid state the forces between anions and cations are strictly coulombic electrostatic forces of attraction between ions of opposite charge. Thus, in salts, discrete cations and anions provide the force to maintain the solid state structure; e.g., such as the chloride ion and the sodium ion in a typical salt such as sodium chloride (Cotton, F. A. & G. Wilkinson, *Advanced Inorganic Chemistry*, Chapter 5, "The Nature of Ionic Substances", $2^{nd}$ revised edn., Interscience Publishers, pp. 35-36, 45-49 (1966).

Although pentaaza 15-membered macrocyclic ring complexes have been disclosed in the literature for a number of indications, the complexes disclosed to-date have limited oral availability (substantially less than 5% when dosed as an aqueous solution, with somewhat greater, though still insufficient, bioavailability when dosed in appropriate oil-based formulations; see, e.g., Table 1). In general, drug absorption from the gastrointestinal tract occurs via passive uptake so that absorption is favored when the drug is in a non-ionized (neutral) and lipophilic form. See, e.g., *Goodman & Gilman's: The Pharmacological Basis of Therapeutics*, Ninth Edition, p. 5-9 (1996). Without wishing to be limited to any particular theory, this is presently also believed to be the case for this class of compounds, as exemplified by GC4419, where the axial ligands are both chloro moieties forming a coordinate covalent bond to the manganese and a neutral complex results:

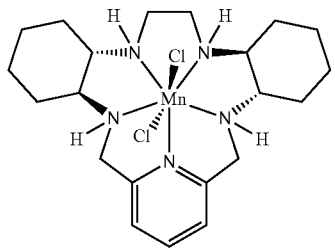

GC4419

It is also understood that good water solubility can aid in the rate of uptake of the drug, as well as the overall bioavailability (*Goodman & Gilman's: The Pharmacological Basis of Therapeutics*, Ninth Edition, p. 5 (1996)). GC4419 and its structural analogues are all relatively readily soluble in water, but may not, however, remain in the neutral non-ionized form in water. Rather, when dissolved in water, the coordinate covalent bonds are cleaved and an aquo axial ligand replaces one or more of the chloro axial ligands, resulting in monocationic or dicationic complexes, as illustrated in Scheme 1, with the cationic compounds expected to be less able to cross the intestinal barrier than the neutral complex.

Scheme 1

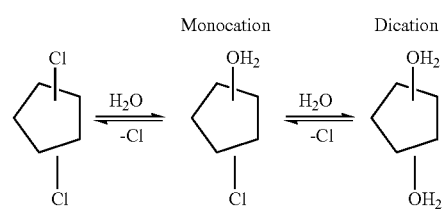

Among the various aspects of the present disclosure, therefore, is the provision of transition metal complexes of pentaaza macrocyclic ring ligands comprising the 15-membered macrocyclic ring of Formula A that can be administered to a subject via oral and other routes of administration, thereby achieving high systemic levels of drug including by oral dosing. In one presently preferred embodiment, the transition metal is manganese.

One aspect of the present disclosure is a transition metal complex comprising a transition metal coordinated by a macrocycle comprising the pentaaza 15-membered macrocyclic ring corresponding to Formula A and two axial ligands having the formula $-OC(O)X_1$ wherein
the macrocycle comprises the pentaaza 15-membered ring corresponding to Formula A and wherein Formula A may be further substituted, where

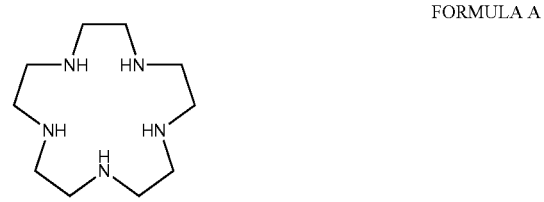 [SMILES: C1CNCCNCCNCCNCCN1]

FORMULA A each of the two axial ligands has the formula $-OC(O)X_1$ wherein
each $X_1$ is independently substituted or unsubstituted phenyl or $-C(-X_2)(-X_3)(-X_4)$;
each $X_2$ is independently substituted or unsubstituted phenyl, or substituted or unsubstituted alkyl;
each $X_3$ is independently hydrogen, hydroxyl, alkyl, amino, $-X_5C(O)R_{13}$ where $X_5$ is NH or O, and $R_{13}$ is $C_1$-$C_{18}$ alkyl, substituted or unsubstituted aryl or $C_1$-$C_{18}$ aralkyl, or $-OR_{14}$, where $R_{14}$ is $C_1$-$C_{18}$ alkyl, substituted or unsubstituted aryl or $C_1$-$C_{18}$ aralkyl, or together with $X_4$ is =O; and
each $X_4$ is independently hydrogen or together with $X_3$ is =O.

A further aspect of the present disclosure is a manganese complex comprising $Mn^{2+}$ or $Mn^{3+}$ coordinated by a macrocycle comprising the pentaaza 15-membered macrocyclic ring corresponding to Formula A and two axial ligands having the formula $-OC(O)X_1$ wherein
each $X_1$ is independently substituted or unsubstituted phenyl or $-C(-X_2)(-X_3)(-X_4)$;
each $X_2$ is independently substituted or unsubstituted phenyl or substituted or unsubstituted alkyl;
each $X_3$ is independently hydrogen, hydroxyl, alkyl, amino, $-X_5C(O)R_{13}$ where $X_5$ is NH or O, and $R_{13}$ is $C_1$-$C_{18}$ alkyl, substituted or unsubstituted aryl or $C_1$-$C_{18}$ aralkyl, or $-OR_{14}$, where $R_{14}$ is $C_1$-$C_{18}$ alkyl, substituted or unsubstituted aryl or $C_1$-$C_{18}$ aralkyl, or together with $X_4$ is =O; and each $X_4$ is independently hydrogen or together with $X_3$ is =O.

A further aspect of the present disclosure is a transition metal complex comprising a transition metal coordinated by the five ring nitrogen atoms of a macrocycle comprising the fused ring system of Formula B (which optionally may be further substituted as described elsewhere herein) and two axial ligands having the formula —OC(O)$X_1$ wherein Formula B has the following formula

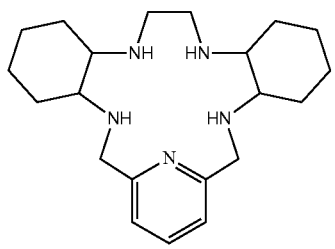

FORMULA B each $X_1$ is independently substituted or unsubstituted phenyl or —C(—$X_2$)(—$X_3$)(—$X_4$);

each $X_2$ is independently substituted or unsubstituted phenyl or substituted or unsubstituted alkyl;

each $X_3$ is independently hydrogen, hydroxyl, alkyl, amino, —$X_5$C(O)$R_{13}$ where $X_5$ is NH or O, and $R_{13}$ is $C_1$-$C_{18}$ alkyl, substituted or unsubstituted aryl or $C_1$-$C_{18}$ aralkyl, or —OR$_{14}$, where $R_{14}$ is $C_1$-$C_{18}$ alkyl, substituted or unsubstituted aryl or $C_1$-$C_{18}$ aralkyl, or together with $X_4$ is =O; and each $X_4$ is independently hydrogen or together with $X_3$ is =O.

A further aspect of the present disclosure is a transition metal complex comprising $Mn^{2+}$ or $Mn^{3+}$ coordinated by a macrocycle comprising the fused ring system of Formula B (which optionally may be further substituted) and two axial ligands having the formula —OC(O)$X_1$ wherein each $X_1$ is independently substituted or unsubstituted phenyl or —C(—$X_2$)(—$X_3$)(—$X_4$);

each $X_2$ is independently substituted or unsubstituted phenyl or substituted or unsubstituted alkyl;

each $X_3$ is independently hydrogen, hydroxyl, alkyl, amino, —$X_5$C(O)$R_{13}$ where $X_5$ is NH or O, and $R_{13}$ is $C_1$-$C_{18}$ alkyl, substituted or unsubstituted aryl or $C_1$-$C_{18}$ aralkyl, or —OR$_{14}$, where $R_{14}$ is $C_1$-$C_{18}$ alkyl, substituted or unsubstituted aryl or $C_1$-$C_{18}$ aralkyl, or together with $X_4$ is =O; and each $X_4$ is independently hydrogen or together with $X_3$ is =O.

A further aspect of the present disclosure is a transition metal complex corresponding to Formula (I):

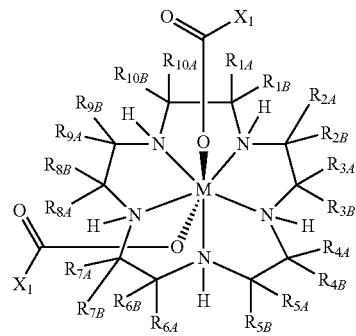

(I)

wherein

M is a transition metal (e.g., $Mn^{2+}$, $Mn^{3+}$, $Mn^{4+}$, $Mn^{6+}$, $Mn^{7+}$, $Fe^{2+}$, $Fe^{3+}$, $Fe^{4+}$, $Fe^{6+}$, $Ni^{2+}$, $Ni^{3+}$, $Cu^{1+}$, $Cu^{2+}$, $V^{2+}$, $V^{3+}$, $V^{4+}$, or $V^{5+}$);

$R_{1A}$, $R_{1B}$, $R_{2A}$, $R_{2B}$, $R_{3A}$, $R_{3B}$, $R_{4A}$, $R_{4B}$, $R_{5A}$, $R_{5B}$, $R_{6A}$, $R_{6B}$, $R_{7A}$, $R_{7B}$, $R_{8A}$, $R_{8B}$, $R_{9A}$, $R_{9B}$, $R_{10A}$, and $R_{10B}$ are independently:

(i) hydrogen;

(ii) a moiety independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, heterocyclyl, and aralkyl radicals and radicals attached to the α-carbon of amino acids (i.e., α-amino acids); or (iii) a moiety independently selected from the group consisting of —OR$_{11}$, —NR$_{11}$R$_{12}$, —COR$_{11}$, —CO$_2$R$_{11}$, —CONR$_{11}$R$_{12}$, —SR$_{11}$, —SOR$_{11}$, —SO$_2$R$_{11}$, —SO$_2$NR$_{11}$R$_{12}$, —N(OR$_{11}$)(R$_{12}$), —P(O)(OR$_{11}$)(OR$_{12}$), —P(O)(OR$_{11}$)(R$_{12}$), —OP(O)(OR$_{11}$)(OR$_{12}$), and substituents attached to the α-carbon of amino acids (i.e., α-amino acids), wherein $R_{11}$ and $R_{12}$ are independently hydrogen or alkyl;

(iv) a member of a substituted or unsubstituted, saturated, partially saturated, or unsaturated cycle or heterocycle containing 3 to 20 carbon ring atoms comprising (a) $R_{1A}$ or $R_{1B}$ and $R_{2A}$ or $R_{2B}$; $R_{3A}$ or $R_{3B}$ and $R_{4A}$ or $R_{4B}$; $R_{5A}$ or $R_{5B}$ and $R_{6A}$ or $R_{6B}$; $R_{7A}$ or $R_{7B}$ and $R_{8A}$ or $R_{8B}$; or $R_{9A}$ or $R_{9B}$ and $R_{10A}$ or $R_{10B}$, together with the carbon atoms to which they are respectively attached;

(b) $R_{10A}$ or $R_{10B}$ and $R_{1A}$ or $R_{1B}$; $R_{2A}$ or $R_{2B}$ and $R_{3A}$ or $R_{3B}$; $R_{4A}$ or $R_{4B}$ and $R_{5A}$ or $R_{5B}$; $R_{6A}$ or $R_{6B}$ and $R_{7A}$ or $R_{7B}$; or $R_{8A}$ or $R_{8B}$ and $R_{9A}$ or $R_{9B}$ together with the carbon atoms to which they are respectively attached; or (c) $R_{1A}$ and $R_{1B}$; $R_{2A}$ and $R_{2B}$; $R_{3A}$ and $R_{3B}$; $R_{4A}$ and $R_{4B}$; $R_{5A}$ and $R_{5B}$; $R_{6A}$ and $R_{6B}$; $R_{7A}$ and $R_{7B}$; $R_{8A}$ and $R_{8B}$; $R_{9A}$ and $R_{9B}$; or $R_{10A}$ and $R_{10B}$ together with the carbon atoms to which they are respectively attached; or (v) a combination of any of (i) through (iv) above;

each $X_1$ is independently substituted or unsubstituted phenyl or —C(—$X_2$)(—$X_3$)(—$X_4$);

each $X_2$ is independently substituted or unsubstituted phenyl or substituted or unsubstituted alkyl;

each $X_3$ is independently hydrogen, hydroxyl, alkyl, amino, —$X_5$C(O)$R_{13}$ where $X_5$ is NH or O, and $R_{13}$ is C$_1$-C$_{18}$ alkyl, substituted or unsubstituted aryl or C$_1$-C$_{18}$ aralkyl, or —OR$_{14}$, where R$_{14}$ is C$_1$-C$_{18}$ alkyl, substituted or unsubstituted aryl or C$_1$-C$_{18}$ aralkyl, or together with X$_4$ is =O;

each X$_4$ is independently hydrogen or together with X$_3$ is =O; and the bonds between the transition metal M and the macrocyclic nitrogen atoms and the bonds between the transition metal M and the oxygen atoms of the axial ligands —OC(O)X$_1$ are coordinate covalent bonds.

Another aspect of the present disclosure is a pentaaza macrocyclic ring complex of Formula (I) corresponding to Formulae (ID$_R$) or (ID$_S$):

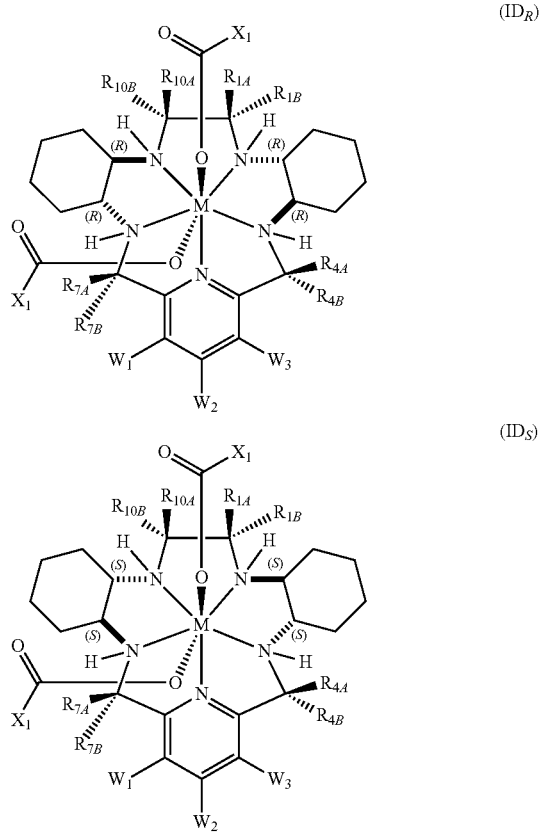

wherein
M is Mn$^{+2}$ or Mn$^{+3}$;
R$_{1A}$, R$_{1B}$, R$_2$, R$_3$, R$_{4A}$, R$_{4B}$, R$_5$, R$_6$, R$_{7A}$, R$_{7B}$, R$_8$, R$_9$, R$_{10A}$, and R$_{10B}$ are independently hydrogen, methyl, ethyl, or propyl;
W$_1$, W$_2$, and W$_3$ are independently halo or hydrogen;
each X$_1$ is independently substituted or unsubstituted phenyl or —C(—X$_2$)(—X$_3$)(—X$_4$);
each X$_2$ is independently substituted or unsubstituted phenyl, methyl, ethyl, or propyl;
each X$_3$ is independently hydrogen, hydroxyl, methyl, ethyl, or propyl, amino, —X$_5$C(O)R$_{13}$ where X$_5$ is NH or O, and R$_{13}$ is C$_1$-C$_{18}$ alkyl, substituted or unsubstituted aryl or C$_1$-C$_{18}$ aralkyl, or —OR$_{14}$, where R$_{14}$ is C$_1$-C$_{18}$ alkyl, substituted or unsubstituted aryl or C$_1$-C$_{18}$ aralkyl, or together with X$_4$ is =O;

each X$_4$ is independently hydrogen or together with X$_3$ is =O; and the bonds between the manganese and the macrocyclic nitrogen atoms and the bonds between the manganese and the oxygen atoms of the axial ligands —OC(O)X$_1$ are coordinate covalent bonds.

Another aspect of the disclosure is a pharmaceutical composition comprising any of the aforementioned pentaaza macrocyclic ring complexes and a pharmaceutically acceptable excipient suitable for administration.

Another aspect of the disclosure is a method for dosing a subject with a pentaaza macrocyclic ring complex, the method comprising administering a pharmaceutical composition comprising any of the aforementioned pentaaza macrocyclic ring complexes to a human subject.

Other objects and features will be in part apparent and in part pointed out hereinafter.

ABBREVIATIONS AND DEFINITIONS

Figure 1:
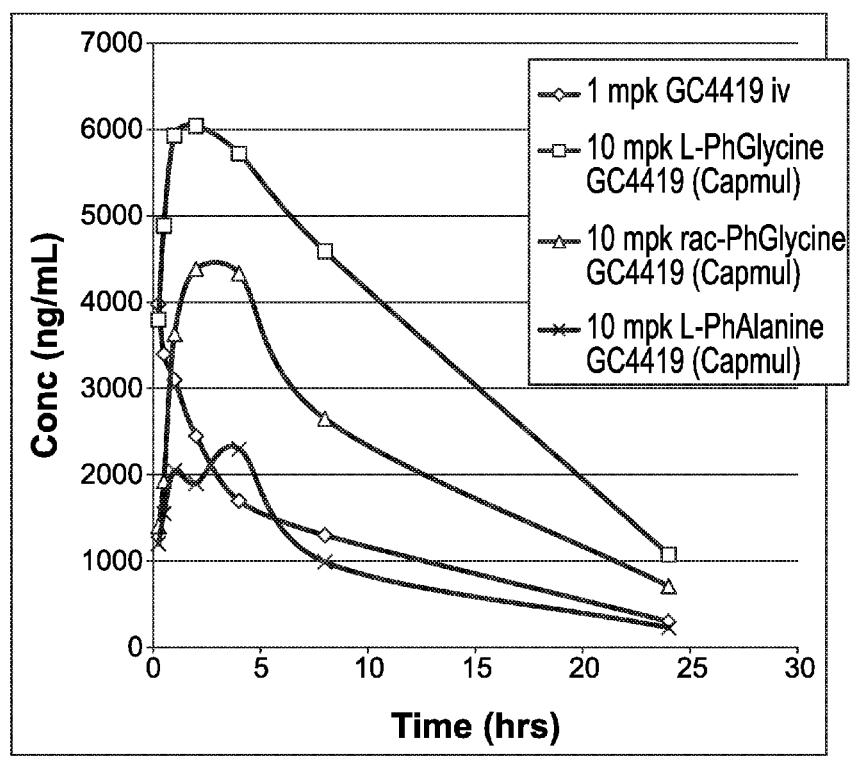
FIG. 1 is a series of profile plots of the plasma concentrations of the parent manganese pentaaza macrocyclic ring complex of GC4419 (independent of the composition of the axial ligands) in the plasma of the minipigs from blood samples at time points up to 24 hrs following administration of test article drugs (where all compounds displayed are derivatives of GC4419) by either intravenous (iv) or intraduodenal (id) delivery, with id test articles formulated in Capmul MCM, as described in the Examples.

The following definitions and methods are provided to better define the present invention and to guide those of ordinary skill in the art in the practice of the present invention. Unless otherwise noted, terms are to be understood according to conventional usage by those of ordinary skill in the relevant art.

"Acyl" means a —COR moiety where R is alkyl, haloalkyl, optionally substituted aryl, or optionally substituted heteroaryl as defined herein, e.g., acetyl, trifluoroacetyl, benzoyl, and the like.

"Acyloxy" means a —OCOR moiety where R is alkyl, haloalkyl, optionally substituted aryl, or optionally substituted heteroaryl as defined herein, e.g., acetyl, trifluoroacetyl, benzoyl, and the like.

"Alkoxy" means a —OR moiety where R is alkyl as defined above, e.g., methoxy, ethoxy, propoxy, or 2-propoxy, n-, iso-, or tert-butoxy, and the like.

"Alkyl" means a linear saturated monovalent hydrocarbon moiety such as of one to six carbon atoms, or a branched saturated monovalent hydrocarbon moiety, such as of three to six carbon atoms, e.g., $C_1$-$C_6$ alkyl groups such as methyl, ethyl, propyl, 2-propyl, butyl (including all isomeric forms), pentyl (including all isomeric forms), and the like.

Moreover, unless otherwise indicated, the term "alkyl" as used herein is intended to include both "unsubstituted alkyls" and "substituted alkyls," the latter of which refers to alkyl moieties having substituents replacing a hydrogen on one or more carbons of the hydrocarbon backbone. Indeed, unless otherwise indicated, all groups recited herein are intended to include both substituted and unsubstituted options.

The term "$C_{x-y}$" when used in conjunction with a chemical moiety, such as alkyl and aralkyl, is meant to include groups that contain from x to y carbons in the chain. For example, the term $C_{x-y}$ alkyl refers to substituted or unsubstituted saturated hydrocarbon groups, including straight chain alkyl and branched chain alkyl groups that contain from x to y carbon atoms in the chain.

"Alkylene" means a linear saturated divalent hydrocarbon moiety, such as of one to six carbon atoms, or a branched saturated divalent hydrocarbon moiety, such as of three to six carbon atoms, unless otherwise stated, e.g., methylene, ethylene, propylene, 1-methylpropylene, 2-methylpropylene, butylene, pentylene, and the like.

"Alkenyl" a linear unsaturated monovalent hydrocarbon moiety, such as of two to six carbon atoms, or a branched saturated monovalent hydrocarbon moiety, such as of three to six carbon atoms, e.g., ethenyl (vinyl), propenyl, 2-propenyl, butenyl (including all isomeric forms), pentenyl (including all isomeric forms), and the like.

"Alkaryl" means a monovalent moiety derived from an aryl moiety by replacing one or more hydrogen atoms with an alkyl group.

"Alkenylcycloalkenyl" means a monovalent moiety derived from an alkenyl moiety by replacing one or more hydrogen atoms with a cycloalkenyl group.

"Alkenylcycloalkyl" means a monovalent moiety derived from a cycloalkyl moiety by replacing one or more hydrogen atoms with an alkenyl group.

"Alkylcycloalkenyl" means a monovalent moiety derived from a cycloalkenyl moiety by replacing one or more hydrogen atoms with an alkyl group.

"Alkylcycloalkyl" means a monovalent moiety derived from a cycloalkyl moiety by replacing one or more hydrogen atoms with an alkyl group.

"Alkynyl" means a linear unsaturated monovalent hydrocarbon moiety, such of two to six carbon atoms, or a branched saturated monovalent hydrocarbon moiety, such as of three to six carbon atoms, e.g., ethynyl, propynyl, butynyl, isobutynyl, hexynyl, and the like.

"Alkoxy" means a monovalent moiety derived from an alkyl moiety by replacing one or more hydrogen atoms with a hydroxy group.

"Amino" means a —$NR^aR^b$ group where $R^a$ and $R^b$ are independently hydrogen, alkyl or aryl.

"Aralkyl" means a monovalent moiety derived from an alkyl moiety by replacing one or more hydrogen atoms with an aryl group.

"Aryl" means a monovalent monocyclic or bicyclic aromatic hydrocarbon moiety of 6 to 10 ring atoms e.g., phenyl or naphthyl.

"Cycle" means a carbocyclic saturated monovalent hydrocarbon moiety of three to ten carbon atoms.

"Cycloalkyl" means a cyclic saturated monovalent hydrocarbon moiety of three to ten carbon atoms, e.g., cyclopropyl, cyclobutyl, cyclopentyl, or cyclohexyl, and the like.

"Cycloalkylalkyl" means a monovalent moiety derived from an alkyl moiety by replacing one or more hydrogen atoms with a cycloalkyl group, e.g., cyclopropylmethyl, cyclobutylmethyl, cyclopentylethyl, or cyclohexylethyl, and the like.

"Cycloalkylcycloalkyl" means a monovalent moiety derived from a cycloalkyl moiety by replacing one or more hydrogen atoms with a cycloalkyl group.

"Cycloalkenyl" means a cyclic monounsaturated monovalent hydrocarbon moiety of three to ten carbon atoms, e.g., cyclopropenyl, cyclobutenyl, cyclopentenyl, or cyclohexenyl, and the like.

"Cycloalkenylalkyl" means a monovalent moiety derived from an alkyl moiety by replacing one or more hydrogen atoms with a cycloalkenyl group, e.g., cyclopropenylmethyl, cyclobutenylmethyl, cyclopentenylethyl, or cyclohexenylethyl, and the like.

"Enteric coating layer" comprises one or more enteric polymers and one more pharmaceutically acceptable excipients comprise but not limited to sustained release agents like ethyl acrylate-methacrylic acid copolymer, ethyl cellulose.

"Ether" means a monovalent moiety derived from an alkyl moiety by replacing one or more hydrogen atoms with an alkoxy group.

"Halo" means fluoro, chloro, bromo, or iodo, preferably fluoro or chloro.

"Heterocycle" or "heterocyclyl" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group is a saturated ring and is not fused to aryl or heteroaryl ring as stated above, it is also referred to herein as saturated monocyclic heterocyclyl.

"Heteroaryl" means a monovalent monocyclic or bicyclic aromatic moiety of 5 to 10 ring atoms where one or more, preferably one, two, or three, ring atoms are heteroatom selected from N, O, or S, the remaining ring atoms being carbon. Representative examples include, but are not limited to, pyrrolyl, pyrazolyl, thienyl, thiazolyl, imidazolyl, furanyl, indolyl, isoindolyl, oxazolyl, isoxazolyl, benzothiazolyl, benzoxazolyl, benzimidazolyl, quinolinyl, isoquinolinyl, pyridinyl, pyrimidinyl, pyrazinyl, pyridazinyl, triazolyl, tetrazolyl, and the like.

"Nitro" means —$NO_2$.

"Organosulfur" means a monovalent moiety a —SR group where R is hydrogen, alkyl or aryl.

"Substituted alkyl," "substituted cycle," "substituted phenyl," "substituted aryl," "substituted heterocycle," and "substituted nitrogen heterocycles" means an alkyl, cycle, aryl, phenyl, heterocycle or nitrogen-containing heterocycle, respectively, optionally substituted with one, two, or three substituents, such as those independently selected from alkyl, alkoxy, alkoxyalkyl, halo, hydroxy, hydroxyalkyl, or organosulfur.

"Thioether" means a monovalent moiety derived from an alkyl moiety by replacing one or more hydrogen atoms with an —SR group wherein R is alkyl.

As used herein, (i) the compound referred to herein and in the Figures as compound 401, 4401 or GC4401 is a reference to the same compound, (ii) the compound referred to herein and in the Figures as compound 403, 4403 or GC4403 is a reference to the same compound, (iii) the compound referred to herein and in the Figures as compound 419, 4419 or GC4419 is a reference to the same compound, and (iv) the compound referred to herein and in the Figures as compound 444, 4444 or GC4444 is a reference to the same compound.

DETAILED DESCRIPTION

Aspects of the present disclosure include novel transition metal complexes of pentaaza ring macrocycles also possessing axial ligands, that have the capacity, in circulation, to convert to the same species as the analogous bis-chloro axial ligand complexes convert to in circulation. The compounds or complexes described herein thus possess similar therapeutic efficacy as their bis-chloro analogs but are significantly more versatile with respect to routes of administration. Stated differently, the compounds of the disclosure possess enhanced oral bioavailability relative to their bis-chloro analogs and, in some embodiments, further possess other advantageous properties selected from one or more of improved intestinal permeability, solubility in aqueous and/or oil-based dosage formulations, ease of manufacture, and/or stability.

The present disclosure is directed, therefore, to 15-membered complexes of pentaaza ring macrocycles and Mn(II) (or other transition metal) wherein the non-macrocyclic ring ligands (that is, axial ligands) covalently bonded to the Manganese(II) (or other transition metal) are selected from a group of moieties that result in the complex having improved versatility with respect to route of administration, including oral administration, relative to, for example, the known bis-chloro complex. In certain embodiments, for example, the complexes described herein exhibit increased uptake across the intestinal wall, but remain capable of losing the axial ligand(s) to water exchange to yield similar species in circulation to those obtained with the bis-chloro complexes illustrated in Scheme 1 above. In these and/or other embodiments, for example, the complexes may also exhibit improved solubility in oil- or water-based (or other) solvents, as compared to the bis-chloro complexes.

In a first aspect, provided is a coordinated metal complex corresponding to Formula (I):

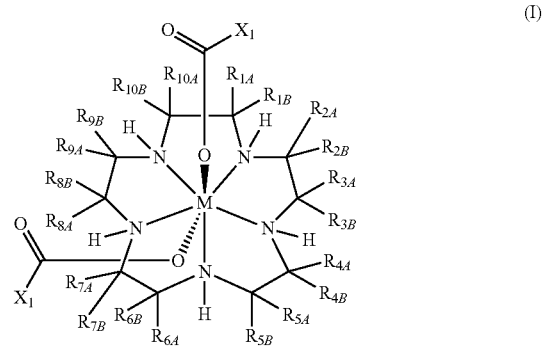

wherein

M is a transition metal (e.g., $Mn^{2+}$, $Mn^{3+}$, $Mn^{4+}$, $Mn^{6+}$, $Mn^{7+}$, $Fe^{2+}$, $Fe^{3+}$, $Fe^{4+}$, $Fe^{6+}$, $Ni^{2+}$, $Ni^{3+}$, $Cu^{1+}$, $Cu^{2+}$, $V^{2+}$, $V^{3+}$, $V^{4+}$, or $V^{5+}$);

$R_{1A}$, $R_{1B}$, $R_{2A}$, $R_{2B}$, $R_{3A}$, $R_{3B}$, $R_{4A}$, $R_{4B}$, $R_{5A}$, $R_{5B}$, $R_{6A}$, $R_{6B}$, $R_{7A}$, $R_{7B}$, $R_{8A}$, $R_{8B}$, $R_{9A}$, $R_{9B}$, $R_{10A}$, and $R_{10B}$ are independently:

(i) hydrogen;

(ii) a moiety independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, heterocyclyl, and aralkyl radicals and radicals attached to the α-carbon of amino acids (i.e., α-amino acids); or (iii) a moiety independently selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(=O)(OR_{11})(OR_{12})$, —$P(=O)(OR_{11})(R_{12})$, —$OP(=O)(OR_{11})(OR_{12})$, and substituents attached to the α-carbon of amino acids (i.e., α-amino acids), wherein $R_{11}$ and $R_{12}$ are independently hydrogen or alkyl;

(iv) a member of a substituted or unsubstituted, saturated, partially saturated, or unsaturated cycle or heterocycle containing 3 to 20 carbon ring atoms comprising (a) $R_{1A}$ or $R_{1B}$ and $R_{2A}$ or $R_{2B}$; $R_{3A}$ or $R_{3B}$ and $R_{4A}$ or $R_{4B}$; $R_{5A}$ or $R_{5B}$ and $R_{6A}$ or $R_{6B}$; $R_{7A}$ or $R_{7B}$ and $R_{8A}$ or $R_{8B}$; or $R_{9A}$ or $R_{9B}$ and $R_{10A}$ or $R_{10B}$ together with the carbon atoms to which they are respectively attached;

(b) $R_{10A}$ or $R_{10B}$ and $R_{1A}$ or $R_{1B}$; $R_{2A}$ or $R_{2B}$ and $R_{3A}$ or $R_{3B}$; $R_{4A}$ or $R_{4B}$ and $R_{5A}$ or $R_{5B}$; $R_{6A}$ or $R_{6B}$ and $R_{7A}$ or $R_{7B}$; or $R_{8A}$ or $R_{8B}$ and $R_{9A}$ or $R_{9B}$ together with the carbon atoms to which they are respectively attached; or (c) $R_{1A}$ and $R_{1B}$; $R_{2A}$ and $R_{2B}$; $R_{3A}$ and $R_{3B}$; $R_{4A}$ and $R_{4B}$; $R_{5A}$ and (c) $R_{1A}$ and $R_{1B}$; $R_{2A}$ and $R_{2B}$; $R_{3A}$ and $R_{3B}$; $R_{4A}$ $9A$ and $R_{9B}$; or $R_{10A}$ and $R_{10B}$ together with the carbon atoms to which they are respectively attached; or (v) a combination of any of (i) through (iv) above;

each $X_1$ is independently substituted or unsubstituted phenyl or —$C(-X_2)(-X_3)(-X_4)$;

each $X_2$ is independently substituted or unsubstituted phenyl or substituted or unsubstituted alkyl;

each $X_3$ is independently hydrogen, hydroxyl, alkyl, amino, —$X_5C(=O)R_{13}$ where $X_5$ is NH or O, and $R_{13}$ is $C_1$-$C_{18}$ alkyl, substituted or unsubstituted aryl or $C_1$-$C_{18}$ aralkyl, or —$OR_{14}$, where $R_{14}$ is $C_1$-$C_{18}$ alkyl, substituted or unsubstituted aryl or $C_1$-$C_{18}$ aralkyl, or together with $X_4$ is (=O);

each $X_4$ is independently hydrogen or together with $X_3$ is (=O); and the bonds between the transition metal M and the macrocyclic nitrogen atoms and the bonds between the transition metal M and the oxygen atoms of the axial ligands —$OC(=O)X_1$ are coordinate covalent bonds.

In a second aspect, this disclosure is directed to pharmaceutical compositions and unit dose formulations comprising a compound of Formula (I) (or any of the embodiments thereof described herein) and a pharmaceutically acceptable excipient. In one embodiment, the pharmaceutical composition is formulated for oral administration. In another embodiment, the pharmaceutical composition is formulated for parenteral administration. In another embodiment, the pharmaceutical composition is formulated for topical administration. Pharmaceutical compositions and unit dose formulations of this second aspect are discussed in further detail below.

Embodiments

Embodiment (IA)

In embodiment (IA), the pentaaza macrocyclic ring complex of Formula (I) corresponds to Formula (IA):

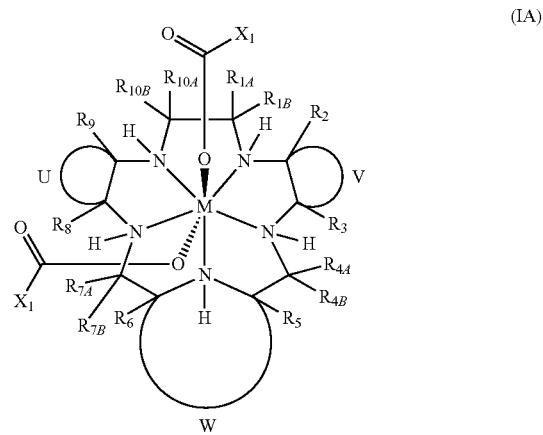

(IA)

wherein

M is a transition metal (e.g., $Mn^{2+}$, $Mn^{3+}$, $Mn^{4+}$, $Mn^{6+}$, $Mn^{7+}$, $Fe^{2+}$, $Fe^{3+}$, $Fe^{4+}$, $Fe^{6+}$, $Ni^{2+}$, $Ni^{3+}$, $Cu^{1+}$, $Cu^{2+}$, $V^{2+}$, $V^{3+}$, $V^{4+}$, or $V^{5+}$);

$R_{1A}$, $R_{1B}$, $R_2$, $R_3$, $R_{4A}$, $R_{4B}$, $R_5$, $R_6$, $R_{7A}$, $R_{7B}$, $R_8$, $R_9$, $R_{10A}$, and $R_{10B}$ are independently hydrogen, hydrocarbyl, substituted hydrocarbyl, heterocyclyl, an amino acid side chain moiety, or a moiety independently selected from the group consisting of —$OR_{11}$, —$NR_{11}R_{12}$, —$COR_{11}$, —$CO_2R_{11}$, —$C(=O)NR_{11}R_{12}$, —$SR_{11}$, —$SOR_{11}$, —$SO_2R_{11}$, —$SO_2NR_{11}R_{12}$, —$N(OR_{11})(R_{12})$, —$P(=O)(OR_{11})(OR_{12})$, —$P(=O)(OR_{11})(R_{12})$, and —$OP(=O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_5$ and $R_6$ attached to the carbon atoms which are both part of the heterocycle and the macrocycle are absent; wherein each $X_1$ is independently substituted or unsubstituted phenyl or —$C(-X_2)(-X_3)(-X_4)$;

each $X_2$ is independently substituted or unsubstituted phenyl or alkyl;

each $X_3$ is independently hydrogen, hydroxyl, alkyl, amino, —$X_5C(=O)R_{13}$ where $X_5$ is NH or O, and $R_{13}$ is $C_1$-$C_{18}$ alkyl, substituted or unsubstituted aryl or $C_1$-$C_{18}$ aralkyl, or —$OR_{14}$, where $R_{14}$ is $C_1$-$C_{18}$ alkyl, substituted or unsubstituted aryl or $C_1$-$C_{18}$ aralkyl, or together with $X_4$ is (=O);

each $X_4$ is independently hydrogen or together with $X_3$ is (=O); and the bonds between the transition metal M and the macrocyclic nitrogen atoms and the bonds between the transition metal M and the oxygen atoms of the axial ligands —OC(=O)$X_1$ are coordinate covalent bonds.

Within embodiment (IA), in one group of compounds, U and V, together with the adjacent carbon atoms of the macrocycle, form a fused substituted or unsubstituted, saturated, cycle or heterocycle having 6 ring atoms and $R_2$, $R_3$, $R_8$, and $R_9$ are hydrogen, and W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 6 ring atoms, provided that when W is a fused aromatic heterocycle the hydrogen attached to the nitrogen which is both part of the heterocycle and the macrocycle and $R_5$ and $R_6$ attached to the carbon atoms which are both part of the heterocycle and the macrocycle are absent.

Within embodiment (IA), and groups contained therein, in one group of compounds M is $Mn^{2+}$, $Mn^{3+}$, $Mn^{4+}$, $Mn^{6+}$, $Mn^{7+}$, $Fe^{2+}$, $Fe^{3+}$, $Fe^{4+}$, or $Fe^{6+}$.

Within embodiment (IA), and groups contained therein, in one group of compounds $X_1$ is phenyl. Within embodiment (IA), and groups contained therein, in one group of compounds $X_1$ is —C(—$X_2$)(—$X_3$)(—$X_4$) and each $X_2$, $X_3$, and $X_4$, in combination, corresponds to any of the combinations identified in the following table:

| Combination | $X_2$ | $X_3$ | $X_4$ |
|---|---|---|---|
| 1 | Ph | H | H |
| 2 | Ph | OH | H |
| 3 | Ph | $NH_2$ | H |
| 4 | Ph | =O ($X_3$ and $X_4$ in combination) | |
| 5 | Ph | $CH_3$ | H |
| 6 | $CH_3$ | H | H |
| 7 | $CH_3$ | OH | H |
| 8 | $CH_3$ | $NH_2$ | H |
| 9 | $CH_3$ | =O ($X_3$ and $X_4$ in combination) | |

Furthermore, within embodiment (IA), and groups contained therein, in one group of compounds $X_1$ is C(—$X_2$)(—$X_3$)(—$X_4$), and $X_3$ is —$X_5C(=O)R_{13}$, such that the combinations of $X_2$, $X_3$ and $X_4$ include any of the combinations identified in the following table:

| Combination | $X_2$ | $X_3$ | $X_4$ |
|---|---|---|---|
| 1 | Ph | $NHC(=O)R_{13}$ | H |
| 2 | Ph | $OC(=O)R_{13}$ | H |
| 3 | $CH_3$ | $NHC(=O)R_{13}$ | H |
| 4 | $CH_3$ | $OC(=O)R_{13}$ | H | where $R_{13}$ is $C_1$-$C_{18}$ alkyl, substituted or unsubstituted aryl or $C_1$-$C_{18}$ aralkyl, or —$OR_{14}$, where $R_{14}$ is $C_1$-$C_{18}$ alkyl, substituted or unsubstituted aryl or $C_1$-$C_{18}$ aralkyl.

Embodiment (IB)

In embodiment (IB), the pentaaza macrocyclic ring complex of Formula (I) corresponds to Formula (IB):

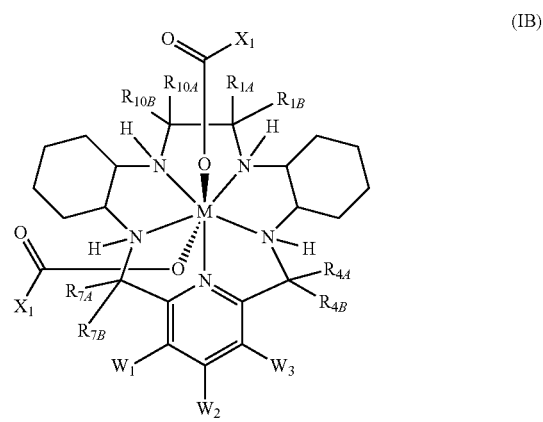

(IB)

wherein

M is $Fe^{+2}$, $Fe^{+3}$, $Mn^{+2}$, or $Mn^{+3}$;

$R_{1A}$, $R_{1B}$, $R_2$, $R_3$, $R_{4A}$, $R_{4B}$, $R_5$, $R_6$, $R_{7A}$, $R_{7B}$, $R_8$, $R_9$, $R_{10A}$, and $R_{10B}$ are as defined in connection with embodiment (IA) above;

$W_1$, $W_2$, and $W_3$ are independently halo, hydrogen, substituted or unsubstituted alkyl, alkenyl, alkynyl, aryl, aralkyl, alkaryl, acyl, acyloxy, alkoxy, an ether, a thioether, or nitro;

each $X_1$ is independently substituted or unsubstituted phenyl or —C(—$X_2$)(—$X_3$)(—$X_4$);

each $X_2$ is independently substituted or unsubstituted phenyl, methyl, ethyl, or propyl;

each $X_3$ is independently hydrogen, hydroxyl, methyl, ethyl, propyl, amino, —$X_5C(=O)R_{13}$ where $X_5$ is NH or O, and $R_{13}$ is $C_1$-$C_{18}$ alkyl, substituted or unsubstituted aryl or $C_1$-$C_{18}$ aralkyl, or —$OR_{14}$, where $R_{14}$ is $C_1$-$C_{18}$ alkyl, substituted or unsubstituted aryl or $C_1$-$C_{18}$ aralkyl, or together with $X_4$ is (=O);

each $X_4$ is independently hydrogen or together with $X_3$ is (=O); and the bonds between the transition metal M and the macrocyclic nitrogen atoms and the bonds between the transition metal M and the oxygen atoms of the axial ligands —OC(=O)$X_1$ are coordinate covalent bonds.

Within embodiment (IB), when one or more of $W_1$, $W_2$, and $W_3$ are substituted alkyl, alkenyl, alkynyl, aryl, aralkyl, or alkaryl, these substituents may contain 1 to 20 carbon atoms (preferably 1 to 6 carbon atoms) and may be linear, branched, or cyclic, with one or more hydrogen atoms of the substituted moieties replaced with a different substituent such as, for example, —OH, —OR, —C(=O)OH, —C(=O)$NH_2$, —$NH_2$, —NHR, —NRR, —SH, —SR, —$SO_2$R, —$SO_2$H, —SOR, heterocyclo, and/or halo (including F, Cl, Br and I), among others, wherein each occurrence of R may be substituted or unsubstituted alkyl, substituted or unsubstituted aryl, or substituted or unsubstituted aralkyl.

Within embodiment (IB), and groups contained therein in one group of compounds M is $Mn^{+2}$ or $Mn^{+3}$. Within embodiment (IB), and groups contained therein in another group of compounds M is $Fe^{+2}$ or $Fe^{+3}$.

Within embodiment (IB), and groups contained therein, in one group of compounds $X_1$ is phenyl. Within embodiment (IB), and groups contained therein, in one group of compounds $X_1$ is —C(—$X_2$)(—$X_3$)(—$X_4$) and each $X_2$, $X_3$, and $X_4$, in combination, corresponds to any of the combinations identified in the following table:

| Combination | $X_2$ | $X_3$ | $X_4$ |
|---|---|---|---|
| 1 | Ph | H | H |
| 2 | Ph | OH | H |
| 3 | Ph | $NH_2$ | H |
| 4 | Ph | =O ($X_3$ and $X_4$ in combination) | |
| 5 | Ph | $CH_3$ | H |
| 6 | $CH_3$ | H | H |
| 7 | $CH_3$ | OH | H |
| 8 | $CH_3$ | $NH_2$ | H |
| 9 | $CH_3$ | =O ($X_3$ and $X_4$ in combination) | |

Furthermore, within embodiment (IB), and groups contained therein, in one group of compounds $X_1$ is C(—$X_2$)(—$X_3$)(—$X_4$), and $X_3$ is —$X_5$C(O)$R_{13}$, such that the combinations of $X_2$, $X_3$ and $X_4$ include any of the combinations identified in the following table:

| Combination | $X_2$ | $X_3$ | $X_4$ |
|---|---|---|---|
| 1 | Ph | NHC(=O)$R_{13}$ | H |
| 2 | Ph | OC(=O)$R_{13}$ | H |
| 3 | $CH_3$ | NHC(=O)$R_{13}$ | H |
| 4 | $CH_3$ | OC(=O)$R_{13}$ | H | where $R_{13}$ is $C_1$-$C_{18}$ alkyl, substituted or unsubstituted aryl or $C_1$-$C_{18}$ aralkyl, or —$OR_{14}$, where $R_{14}$ is $C_1$-$C_{18}$ alkyl, substituted or unsubstituted aryl or $C_1$-$C_{18}$ aralkyl.

Embodiment (IC)

In embodiment (IC), the pentaaza macrocyclic ring complex of Formula (I) corresponds to Formulae ($IC_R$) or ($IC_S$):

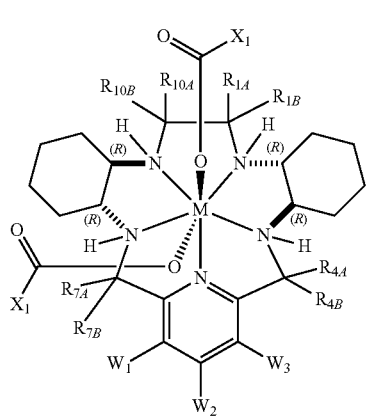

($IC_R$)

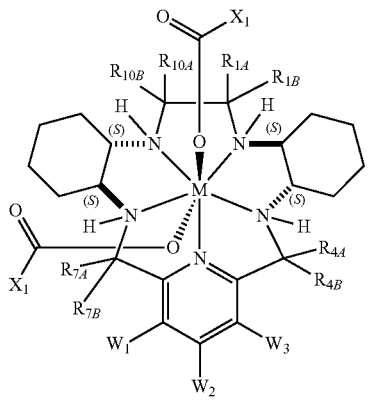

($IC_S$)

wherein
M is $Fe^{+2}$, $Fe^{+3}$, $Mn^{+2}$, or $Mn^{+3}$;
$R_{1A}$, $R_{1B}$, $R_2$, $R_3$, $R_{4A}$, $R_{4B}$, $R_5$, $R_6$, $R_{7A}$, $R_{7B}$, $R_8$, $R_9$, $R_{10A}$, and $R_{10B}$ are independently hydrogen or substituted or unsubstituted alkyl;
$W_1$, $W_2$, and $W_3$ are independently halo or hydrogen;
each $X_1$ is independently substituted or unsubstituted phenyl or —C(—$X_2$)(—$X_3$)(—$X_4$);
each $X_2$ is independently substituted or unsubstituted phenyl, methyl, ethyl, or propyl;
each $X_3$ is independently hydrogen, hydroxyl, methyl, ethyl, propyl, amino, —$X_5$C(=O)$R_{13}$ where $X_5$ is NH or O, and $R_{13}$ is alkyl, substituted or unsubstituted aryl or $C_1$-$C_{18}$ aralkyl, or —$OR_{14}$, where $R_{14}$ is $C_1$-$C_{18}$ alkyl, substituted or unsubstituted aryl or $C_1$-$C_{18}$ aralkyl, or together with $X_4$ is (=O);
each $X_4$ is independently hydrogen or together with $X_3$ is (=O); and
the bonds between the transition metal M and the macrocyclic nitrogen atoms and the bonds between the transition metal M and the oxygen atoms of the axial ligands —OC(O)$X_1$ are coordinate covalent bonds.

Within embodiment (IC), in one group of compounds M is $Mn^{2+}$. Within embodiment (IC), in another group of compounds M is $Mn^{3+}$.

Within embodiment (IC), and groups contained therein, in one group of compounds $X_1$ is phenyl. Within embodiment (IC), and groups contained therein, in one group of compounds $X_1$ is —C(—$X_2$)(—$X_3$)(—$X_4$) and each $X_2$, $X_3$, and $X_4$, in combination, corresponds to any of the combinations identified in the following table:

| Combination | $X_2$ | $X_3$ | $X_4$ |
|---|---|---|---|
| 1 | Ph | H | H |
| 2 | Ph | OH | H |
| 3 | Ph | $NH_2$ | H |
| 4 | Ph | =O ($X_3$ and $X_4$ in combination) | |
| 5 | Ph | $CH_3$ | H |
| 6 | $CH_3$ | H | H |
| 7 | $CH_3$ | OH | H |
| 8 | $CH_3$ | $NH_2$ | H |
| 9 | $CH_3$ | =O ($X_3$ and $X_4$ in combination) | |

Furthermore, within embodiment (IC), and groups contained therein, in one group of compounds $X_1$ is C(—$X_2$)

($-X_3$)($-X_4$), and $X_3$ is $-X_5C(O)R_{13}$, such that the combinations of $X_2$, $X_3$ and $X_4$ include any of the combinations identified in the following table:

| Combination | $X_2$ | $X_3$ | $X_4$ |
|---|---|---|---|
| 1 | Ph | NHC(=O)$R_{13}$ | H |
| 2 | Ph | OC(=O)$R_{13}$ | H |
| 3 | $CH_3$ | NHC(=O)$R_{13}$ | H |
| 4 | $CH_3$ | OC(=O)$R_{13}$ | H | where $R_{13}$ is $C_1$-$C_{18}$ alkyl, substituted or unsubstituted aryl or $C_1$-$C_{18}$ aralkyl, or $-OR_{14}$, where $R_{14}$ is $C_1$-$C_{18}$ alkyl, substituted or unsubstituted aryl or $C_1$-$C_{18}$ aralkyl.

Embodiment (ID)

In embodiment (ID), the pentaaza macrocyclic ring complex of Formula (I) corresponds to Formulae ($ID_R$) or ($ID_S$):

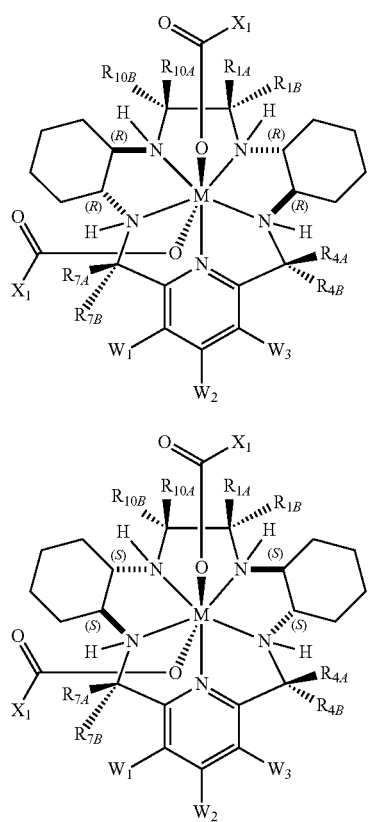

wherein

M is $Mn^{+2}$ or $Mn^{+3}$;

$R_{1A}$, $R_{1B}$, $R_2$, $R_3$, $R_{4A}$, $R_{4B}$, $R_5$, $R_6$, $R_{7A}$, $R_{7B}$, $R_8$, $R_9$, $R_{10A}$, and $R_{10B}$ are independently hydrogen, methyl, ethyl, or propyl;

$W_1$, $W_2$, and $W_3$ are independently halo or hydrogen;

each $X_1$ is independently substituted or unsubstituted phenyl or $-C(-X_2)(-X_3)(-X_4)$;

each $X_2$ is independently substituted or unsubstituted phenyl, methyl, ethyl, or propyl;

each $X_3$ is independently hydrogen, hydroxyl, methyl, ethyl, propyl, amino, $-X_5C(=O)R_{13}$ where $X_5$ is NH or O, and $R_{13}$ is $C_1$-$C_{18}$ alkyl, substituted or unsubstituted aryl or $C_1$-$C_{18}$ aralkyl, or $-OR_{14}$, where $R_{14}$ is $C_1$-$C_{18}$ alkyl, substituted or unsubstituted aryl or $C_1$-$C_{18}$ aralkyl, or together with $X_4$ is (=O);

each $X_4$ is independently hydrogen or together with $X_3$ is (=O); and the bonds between the transition metal M ($Mn^{+2}$ or $Mn^{+3}$) and the macrocyclic nitrogen atoms and the bonds between the transition metal M and the oxygen atoms of the axial ligands $-OC(=O)X_1$ are coordinate covalent bonds.

Within embodiment (ID), in one group of compounds M is $Mn^{2+}$. Within embodiment (ID), in another group of compounds M is $Mn^{3+}$.

Within embodiment (ID), and groups contained therein, in one group of compounds $R_{1A}$, $R_{1B}$, $R_{4A}$, $R_{4B}$, $R_{7A}$, $R_{7B}$, $R_{10A}$, and $R_{10B}$ are each hydrogen. Within embodiment (ID), and groups contained therein, in one group of compounds $R_{1B}$, $R_{4A}$, $R_{4B}$, $R_{7A}$, $R_{7B}$, $R_{10A}$, and $R_{10B}$ are each hydrogen and $R_{1A}$ is methyl. Within embodiment (ID), and groups contained therein, in one group of compounds $R_{1A}$, $R_{4A}$, $R_{4B}$, $R_{7A}$, $R_{7B}$, $R_{10A}$, and $R_{10B}$ are each hydrogen and $R_{1B}$ is methyl. Within embodiment (ID), and groups contained therein, in one group of compounds $R_{1A}$, $R_{1B}$, $R_{4B}$, $R_{7A}$, $R_{10A}$, and $R_{10B}$ are each hydrogen and $R_{4A}$ and $R_{7B}$ are each methyl. Within embodiment (ID), and groups contained therein, in one group of compounds $R_{1A}$, $R_{1B}$, $R_{4A}$, $R_{7B}$, $R_{10A}$, and $R_{10B}$ are each hydrogen and $R_{4B}$ and $R_{7A}$ are each methyl.

Within embodiment (ID), and groups contained therein, in one group of compounds $X_1$ is phenyl. Within embodiment (ID), and groups contained therein, in one group of compounds $X_1$ is $-C(-X_2)(-X_3)(-X_4)$ and each $X_2$, $X_3$, and $X_4$, in combination, corresponds to any of the combinations identified in the following table:

| Combination | $X_2$ | $X_3$ | $X_4$ |
|---|---|---|---|
| 1 | Ph | H | H |
| 2 | Ph | OH | H |
| 3 | Ph | $NH_2$ | H |
| 4 | Ph | =O ($X_3$ and $X_4$ in combination) | |
| 5 | Ph | $CH_3$ | H |
| 6 | $CH_3$ | H | H |
| 7 | $CH_3$ | OH | H |
| 8 | $CH_3$ | $NH_2$ | H |
| 9 | $CH_3$ | =O ($X_3$ and $X_4$ in combination) | |

Furthermore, within embodiment (ID), and groups contained therein, in one group of compounds $X_1$ is C($-X_2$)($-X_3$)($-X_4$), and $X_3$ is $-X_5C(O)R_{13}$, such that the combinations of $X_2$, $X_3$ and $X_4$ include any of the combinations identified in the following table:

| Combination | $X_2$ | $X_3$ | $X_4$ |
|---|---|---|---|
| 1 | Ph | NHC(=O)$R_{13}$ | H |
| 2 | Ph | OC(=O)$R_{13}$ | H |
| 3 | $CH_3$ | NHC(=O)$R_{13}$ | H |
| 4 | $CH_3$ | OC(=O)$R_{13}$ | H | where $R_{13}$ is $C_1$-$C_{18}$ alkyl, substituted or unsubstituted aryl or $C_1$-$C_{18}$ aralkyl, or $-OR_{14}$, where $R_{14}$ is $C_1$-$C_{18}$ alkyl, substituted or unsubstituted aryl or $C_1$-$C_{18}$ aralkyl.

Embodiment (IE)

In embodiment (IE), the pentaaza macrocyclic ring complex of Formula (I) corresponds to Formulae ($IE_{R1}$), ($IE_{S1}$), ($IE_{R2}$), ($IE_{S2}$), ($IE_{R3}$), or ($IE_{S3}$):

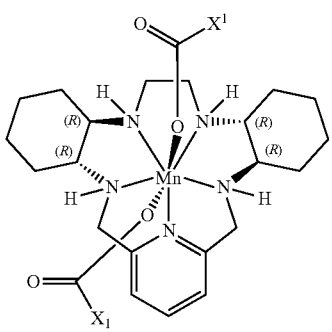
(IE_R1)

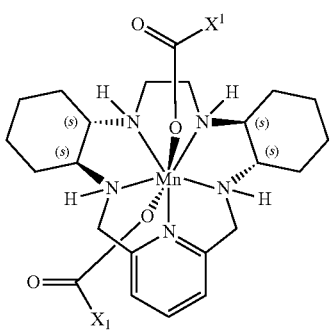
(IE_R2)

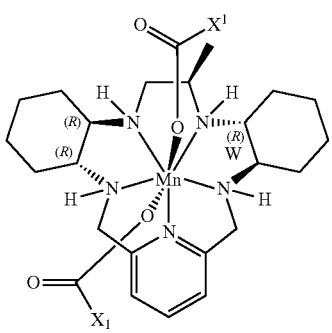
(IE_S2)

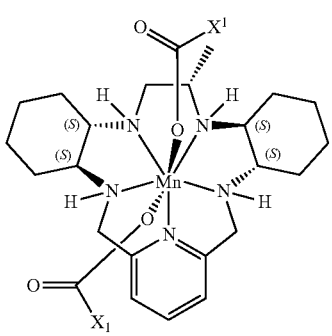

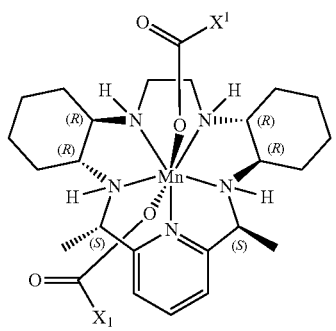
(IE_R3)

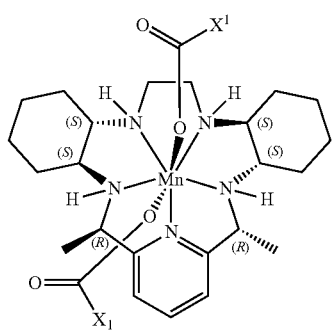
(IE_S1)

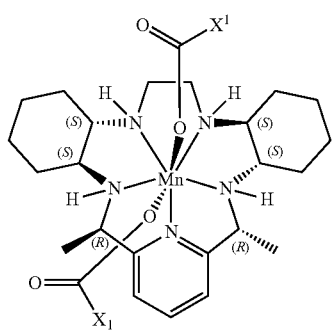
(IE_S3)

wherein

Mn is $Mn^{+2}$ or $Mn^{+3}$;

each $X_1$ is independently substituted or unsubstituted phenyl or —C(—$X_2$)(—$X_3$)(—$X_4$);

each $X_2$ is independently hydrogen, hydroxyl, methyl, ethyl, propyl, amino, —$X_5$C(=O)$R_{13}$ where $X_5$ is NH or O, and $R_{13}$ is $C_1$-$C_{18}$ alkyl, substituted or unsubstituted aryl or $C_1$-$C_{18}$ aralkyl, or —O$R_{14}$, where $R_{14}$ is $C_1$-$C_{18}$ alkyl, substituted or unsubstituted aryl or $C_1$-$C_{18}$ aralkyl, or together with $X_4$ is (=O);

each $X_4$ is independently hydrogen or together with $X_3$ is (=O); and the bonds between the manganese and the macrocyclic nitrogen atoms and the bonds between the manganese and the oxygen atoms of the axial ligands —OC(=O)$X_1$ are coordinate covalent bonds.

Within embodiment (IE), and groups contained therein, in one group of compounds $X_1$ is phenyl. Within embodiment (IE), and groups contained therein, in one group of compounds $X_1$ is —C(—$X_2$)(—$X_3$)(—$X_4$) and each $X_2$, $X_3$, and $X_4$, in combination, corresponds to any of the combinations identified in the following table:

| Combination | $X_2$ | $X_3$ | $X_4$ |
|---|---|---|---|
| 1 | Ph | H | H |
| 2 | Ph | OH | H |
| 3 | Ph | $NH_2$ | H |
| 4 | Ph | =O ($X_3$ and $X_4$ in combination) | |
| 5 | Ph | $CH_3$ | H |
| 6 | $CH_3$ | H | H |
| 7 | $CH_3$ | OH | H |
| 8 | $CH_3$ | $NH_2$ | H |
| 9 | $CH_3$ | =O ($X_3$ and $X_4$ in combination) | |

Furthermore, within embodiment (IE), and groups contained therein, in one group of compounds $X_1$ is —C(—$X_2$)(—$X_3$)(—$X_4$), and $X_3$ is —$X_5$C(O)$R_{13}$, such that the combinations of $X_2$, $X_3$ and $X_4$ include any of the combinations identified in the following table:

| Combination | $X_2$ | $X_3$ | $X_4$ |
|---|---|---|---|
| 1 | Ph | NHC(=O)$R_{13}$ | H |
| 2 | Ph | OC(=O)$R_{13}$ | H |
| 3 | $CH_3$ | NHC(=O)$R_{13}$ | H |
| 4 | $CH_3$ | OC(=O)$R_{13}$ | H | where $R_{13}$ is $C_1$-$C_{18}$ alkyl, substituted or unsubstituted aryl or $C_1$-$C_{18}$ aralkyl, or —O$R_{14}$, where $R_{14}$ is $C_1$-$C_{18}$ alkyl, substituted or unsubstituted aryl or $C_1$-$C_{18}$ aralkyl.

Unit Dose Formulations and Pharmaceutical Compositions

As noted above, a second aspect of the present disclosure relates to the unit dose formulations and pharmaceutical compositions comprising the compounds described herein, typically together with a pharmaceutically acceptable carrier or excipient, and optionally in combination with another pharmaceutically active compound or compounds. The pharmaceutical compositions include the pentaaza macrocyclic ring complex corresponding to Formula (I) (or any of the embodiments thereof or other compounds described herein, such as any of the compounds set forth in Table I of the Examples section), typically formulated as a pharmaceutical dosage form, optionally in combination with a pharmaceutically acceptable carrier, additive or excipient. In one embodiment, for example, the pharmaceutical composition comprises the compound of Formula (I) (or any of the embodiments thereof or other compounds described herein, such as any of the compounds set forth in Table I of the Examples section) and a pharmaceutically acceptable carrier or excipient. Unit dose formulations and pharmaceutical compositions according to the present disclosure may be used, for example, in the treatment of various cardiovascular disorders, cerebrovascular disorders, dermatological disorders, fibrotic disorders, gastrointestinal disorders, immunological disorders, inflammatory disorders, metabolic disorders, neurological disorders, ophthalmic disorders, pulmonary disorders, infectious diseases, tissue damage, and combinations thereof. Particular diseases and conditions include fibrosis, inflammatory diseases and conditions (including, for example, inflammatory bowel disease, rheumatoid arthritis, asthma, COPD, pancreatitis, and the like), dermatitis, psoriasis, and the like, as well as for protecting tissue against damage resulting from a cancer treatment or other exposure to radiation, as discussed in further detail below.

Formulations containing the compounds may take the form of solid, semi-solid, lyophilized powder, or liquid dosage forms such as, for instance, aerosols, capsules, creams, emulsions, foams, gels/jellies, injectables, lotions, ointments, pastes, powders, soaps, solutions, sprays, suppositories, suspensions, sustained-release formulations, tablets, tinctures, transdermal patches, and the like, preferably in unit dosage forms suitable for simple administration of precise dosages. If formulated as a fixed dose, such pharmaceutical compositions or formulation products preferably employ the compounds within certain dosage ranges. Depending on the intended mode of administration, therefore, in some embodiments the compositions can be in solid, semi-solid or liquid dosage form, such as, for example, injectables, tablets, pills, time-release capsules, elixirs, tinctures, emulsions, syrups, liquids, suspensions, or the like, sometimes in unit dosages and consistent with conventional pharmaceutical practices. Likewise, in some embodiments, they can also be administered via intravenous (both bolus and infusion), intraperitoneal, subcutaneous, topical, or intramuscular routes, or other routes described herein, all using forms well known to those skilled in the pharmaceutical arts.

One particular embodiment of the present disclosure is directed to a unit dose formulation comprising the compound corresponding to Formula (I) (or any of the embodiments thereof or other compounds described herein, such as any of the compounds set forth in Table I of the Examples section) in an oral dosage form as described herein. Another particular embodiment of the present disclosure is directed to a unit dose formulation comprising the compound corresponding to Formula (I) (or any of the embodiments thereof or other compounds described herein, such as any of the compounds set forth in Table I of the Examples section) in a parenteral dosage form as described herein.

For both oral and non-oral dosage formulations, the above-described compounds (or any of the embodiments thereof or other compounds described herein, such as any of the compounds set forth in Table I of the Examples section) may be dispersed in a pharmaceutically acceptable carrier prior to administration to the mammal. The carrier, also known in the art as an excipient, vehicle, auxiliary, adjuvant, or diluent, is typically a substance which is pharmaceutically inert, confers a suitable consistency or form to the composition, and does not diminish the efficacy of the compound. The carrier is generally considered to be "pharmaceutically or pharmacologically acceptable" if it does not produce an unacceptably adverse, allergic or other untoward reaction when administered to a mammal, especially a human.

The selection of a pharmaceutically acceptable carrier will also, in part, be a function of the route of administration. In general, the compositions of the described herein can be formulated for any route of administration so long as the blood circulation system is available via that route and in accordance with conventional routes of administration of the component (e.g., the compound). For example, suitable routes of administration include, but are not limited to, oral, parenteral (e.g., intravenous, intraarterial, subcutaneous, intramuscular, intraorbital, intracapsular, intraspinal, intraperitoneal, or intrasternal), topical (nasal, transdermal, buccal, ophthalmic), intravesical, intrathecal, enteral, pulmonary, intralymphatic, intracavital, vaginal, rectal, transurethral, intradermal, intraocular, aural, intramammary, orthotopic, intratracheal, intralesional, percutaneous, endoscopical, transmucosal, sublingual and intestinal administration. In one particularly preferred embodiment, the compound (or a pharmaceutical composition or unit dose formulation including the compound) (e.g., those corresponding to Formula (I) (or any of the embodiments thereof or other compounds described herein, such as any of the compounds and/or formulations set forth in Table I of the Examples section) is formulated for oral administration.

Pharmaceutically acceptable carriers for use in combination with the compounds and compositions of the present disclosure are well known to those of ordinary skill in the art and are selected based upon a number of factors: the particular compound(s) and agent(s) used, and its/their concentration, stability and intended bioavailability; safety; the subject, its age, size and general condition; and the route of administration.

Suitable components (e.g., carriers and/or excipients) used in formulating solid or semi-solid dosage forms such as tablets, gelatin capsules, or gels/suspensions may include, for example, diluents (such as water, glycerides, or mixtures thereof, corn oil, olive oil, sunflower oil, safflower oil, lactose, dextrose, sucrose, mannitol, sorbitol, cellulose, sodium, saccharin, glucose and/or glycine); lubricants (such as silica, talcum, its magnesium or calcium salt, sodium oleate, sodium stearate, magnesium stearate, sodium benzoate, sodium acetate, sodium chloride and/or polyethylene glycol); binders (such as magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone); disintegrants (such as starches, agar, methyl cellulose, bentonite, xanthan gum, or effervescent mixtures; absorbents, colorants, flavorants, and/or sweeteners; and combinations thereof. Methods of preparing such solid and semi-solid dosage forms using the active pharmaceutical ingredient and other components are well known in the art. For example, compositions in liquid, semi-solid or paste form can be filled into hard gelatin or soft gelatin capsules using appropriate filling machines. Alternatively, the composition can also be extruded, sprayed, granulated or coated onto a substrate to become a powder, granule or bead that can be further encapsulated or tableted with or without the addition of appropriate solidifying or binding agents. This approach also allows for the creation of a "fused mixture," a "solid solution" or a "eutectic mixture." These and other methods for making oral formulations can be found, for example, in "Remington: The Science and Practice of Pharmacy," 20$^{th}$ ed. Ed. A. R. Gennaro, 2000, Lippincott Williams & Wilkins.

Suitable components (e.g., carriers and/or excipients) used in formulating liquid dosage forms, for example, include nonaqueous, pharmaceutically-acceptable polar solvents such as oils, alcohols, amides, esters, ethers, ketones, hydrocarbons and mixtures thereof, as well as water, saline solutions (e.g., U.S.P. and isotonic sodium chloride solutions), dextrose solutions (e.g., D5W), electrolyte solutions, or any other aqueous, pharmaceutically acceptable liquid. In certain preferred embodiments, the pharmaceutical composition is in the form of an aqueous solution comprising the compound corresponding to Formula (I) (or any of the embodiments thereof or other compounds described herein, such as any of the compounds and/or formulations set forth in Table I of the Examples section) and saline (e.g., normal saline, that is, a sterile solution of 0.9% w/v of NaCl in water). In these and other embodiments, for example, the saline is preferably a physiologically buffered saline solution (i.e., buffered saline). The buffering agent may provide suitable buffering capacity around pH 7-8.5, or around pH 7.8, or within the range of pH 7.3-8. The buffering agent is preferably chemically inert and physiologically and pharmaceutically acceptable. Exemplary buffers include phosphate-based buffers, carbonate-based buffers, tris-based buffers, amino acid-based buffers (e.g., arginine, lysine, and other natural amino acids), and citrate-based buffers. Carbonate buffers (such as sodium or calcium carbonate or bicarbonate buffers) may be particularly useful in some embodiments due to their ready supply, strong buffering capacity, and compatibility. One particularly preferred buffering agent is sodium bicarbonate. In one preferred embodiment, for example, the pharmaceutically acceptable carrier comprises a buffered saline solution; more preferably in this embodiment, the buffered saline solution is a bicarbonate-buffered saline solution.

In one particular embodiment, the unit dose formulation for oral administration including the compound (e.g., those corresponding to Formula (I) (or any of the embodiments thereof or other compounds described herein, such as any of the compounds and/or formulations set forth in Table I of the Examples section) further comprises at least one of a lipophilic surfactant and an oil.

Certain suitable lipophilic surfactants and/or oils include mono-, di- and/or tri-glycerides of fatty acids, such as Imwitor 988 (glyceryl mono-/di-caprylate), Imwitor 742 (glyceryl mono-di-caprylate/caprate), Imwitor 308 (glyceryl mono-caprylate), Imwitor 191 (glyceryl mono-stearate), Softigen 701 (glyceryl mono-/di-ricinoleate), Capmul MCM (glyceryl caprylate/caprate), Capmul MCM(L) (liquid form of Capmul MCM), Capmul GMO (glyceryl mono-oleate), Capmul GDL (glyceryl dilaurate), Maisine (glyceryl mono-linoleate), Peceol (glyceryl mono-oleate), Myverol 18-92 (distilled monoglycerides from sunflower oil) and Myverol 18-06 (distilled monoglycerides from hydrogenated soybean oil), Precirol ATO 5 (glyceryl palmitostearate), Gelucire 39/01 (semi-synthetic glycerides, i.e., C12-18 mono-, di- and tri-glycerides) and Miglyol 812 N (a mixture of caprylic/capric acid triglycerides); acetic, succinic, lactic, citric and/or tartaric esters of mono- and/or di-glycerides of fatty acids, for example, Myvacet 9-45 (distilled acetylated monoglycerides), Miglyol 829 (caprylic/capric diglyceryl succinate), Myverol SMG (mono/di-succinylated monoglycerides), Imwitor 370 (glyceryl stearate citrate), Imwitor 375 (glyceryl monostearate/citrate/lactate) and Crodatem T22 (diacetyl tartaric esters of monoglycerides); propylene glycol mono- and/or di-esters of fatty acids, for example, Lauroglycol (propylene glycol monolaurate), Mirpyl (propylene glycol monomyristate), Captex 200 (propylene glycol dicaprylate/dicaprate), Miglyol 840 (propylene glycol dicaprylate/dicaprate) and Neobee M-20 (propylene glycol dicaprylate/dicaprate); polyglycerol esters of fatty acids such as Plurol oleique (polyglyceryl oleate), Caprol ET (polyglyceryl mixed fatty acids) and Drewpol 10.10.10 (polyglyceryl oleate); castor oil ethoxylates of low ethoxylate content (HLB<10) such as Etocas 5 (5 moles of ethylene oxide reacted with 1 mole of castor oil) and Sandoxylate 5 (5 moles of ethylene oxide reacted with 1 mole of castor oil; acid and ester ethoxylates formed by reacting ethylene oxide with fatty acids or glycerol esters of fatty acids (HLB<10) such as Crodet 04 (polyoxyethylene (4) lauric acid), Cithrol 2MS (polyoxyethylene (2) stearic acid), Marlosol 183 (polyoxyethylene (3) stearic acid) and Marlowet G 12DO (glyceryl 12 EO dioleate); sorbitan esters of fatty acids, for example, Span 20 (sorbitan monolaurate), Crill 1 (sorbitan monolaurate) and Crill 4 (sorbitan mono-oleate); transesterification products of natural or hydrogenated vegetable oil triglyceride and a polyalkylene polyol (HLB<10), e.g., Labrafil M1944CS (polyoxyethylated apricot kernel oil), Labrafil M2125CS (polyoxyethylated corn oil) and Gelucire 37/06 (polyoxyethylated hydrogenated coconut); alcohol ethyoxylates (HLB<10), e.g., Volpo N3 (polyoxyethylated (3) oleyl ether), Brij 93 (polyoxyethylated (2) oleyl ether), Marlowet LA4 (polyoxyethylated (4) lauryl ether); and pluronics, for example, Polyoxyethylene-polyoxypropylene co-polymers and block co-polymers (HLB<10) e.g., Synperonic PE L42 (HLB=8) and Synperonic PE L61 (HLB=3).

In another particular embodiment, the unit dose formulation for oral administration including the compound (e.g., those corresponding to Formula (I) (or any of the embodiments thereof or other compounds described herein, such as any of the compounds and/or formulations set forth in Table I of the Examples section) further comprises a digestible oil (i.e., an oil that is capable of undergoing de-esterification or hydrolysis in the presence of pancreatic lipase in vivo under normal physiological conditions). Digestible oils may be glycerol triesters of medium chain ($C_7$-$C_{13}$) or long chain ($C_{14}$-$C_{22}$) fatty acids with low molecular weight (up to $C_6$) mono-, di- or polyhydric alcohols. Suitable examples of digestible oils include, for example, vegetable oils (e.g., soybean oil, safflower seed oil, corn oil, olive oil, castor oil, cottonseed oil, arachis oil, sunflower seed oil, coconut oil, palm oil, rapeseed oil, black currant oil, evening primrose oil, grape seed oil, wheat germ oil, sesame oil, avocado oil, almond, borage, peppermint and apricot kernel oils) and animal oils (e.g., fish liver oil, shark oil and mink oil). In certain embodiments, the digestible oil is a vegetable oil, for example, soybean oil, safflower seed oil, corn oil, olive oil, castor oil, cottonseed oil, arachis oil, sunflower seed oil, coconut oil, palm oil, rapeseed oil, evening primrose oil, grape seed oil, wheat germ oil, sesame oil, avocado oil, almond oil, borage oil, peppermint oil, apricot kernel oil, and combinations thereof.

Where injectable pharmaceutical formulations are employed, they are preferably sterile. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use. The compositions can be provided, prepared, stored, or transported in any container suitable for maintaining sterility. The container can incorporate means for dispensing an aqueous composition such as, for example, a pierceable or removable seal. The compositions can be dispensed, for example, by extraction with a syringe or by pouring the composition directly into a device (e.g., a syringe, intravenous (IV) bag, or machine) for administration to a patient. Other means for providing, preparing, storing, transporting, and dispensing sterile pharmaceutical compositions are known to those skilled in the art.

Other pharmaceutically acceptable carriers and excpieints for use in the pharmaceutical compositions and dosage forms described herein are well known to those of ordinary skill in the art, and are identified in The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.) (Marcel Dekker, Inc., New York, N.Y., 1995), The Pharmacological Basis of Therapeutics, (Goodman & Gilman, McGraw Hill Publishing), Pharmaceutical Dosage Forms, (H. Lieberman et al., eds.) (Marcel Dekker, Inc., New York, N.Y., 1980), Remington's Pharmaceutical Sciences (A. Gennaro, ed., 19th ed.) (Mack Publishing, Easton, Pa., 1995), The United States Pharmacopeia 24, The National Formulary 19, (National Publishing, Philadelphia, Pa., 2000), and A. J. Spiegel et al., Use of Nonaqueous Solvents in Parenteral Products, Journal of Pharmaceutical Sciences, Vol. 52, No. 10, pp. 917-927 (1963).

In certain embodiments, the pharmaceutical composition administered to the subject in accordance with the methods described herein consists essentially of the compound corresponding to Formula (I) (or any of the embodiments thereof or other compounds described herein, such as any of the compounds set forth in Table I of the Examples section) and a pharmaceutically acceptable carrier. In other embodiments, the pharmaceutical composition comprises the compound, a pharmaceutically acceptable carrier, and one or more additional pharmaceutically active agents or compounds. In these embodiments, the pharmaceutical compositions described herein are products that result from the mixing or combining of more than one active ingredient and include both fixed and non-fixed combinations of the active ingredients. Fixed combinations are those in which the active ingredients, e.g., the compound and another pharmaceutically active agent or compound described herein, are both administered to a patient simultaneously in the form of a single entity or dosage. Non-fixed combinations are those in which the active ingredients, e.g., the compound and another pharmaceutically active agent or compound, are administered to a subject as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

It is contemplated that co-formulations of the compound (e.g., those corresponding to Formula (I) (or any of the embodiments thereof or other compounds described herein, such as any of the compounds set forth in Table I of the Examples section) and one or more additional pharmaceutically active agents or compounds may employ conventional formulation techniques for these components individually, or alternative formulation routes, subject to compatibility and efficacy of the various components, in combination.

In one embodiment, a compound and/or formulation of the present disclosure (including any of the compounds described herein, such as any of the compounds and/or formulations as set forth in Table I of the Examples section) is formulated for oral administration and the formulation comprises an enteric release layer or composition. For example, the oral dosage form may be an enteric coated tablet, multi-particulate or multilayered tablet or capsule; a gelatin, a soft gelatin or equivalent thereof; a vinyl or a polyvinyl acetate phthalate or equivalent thereof; an ACRYL-EZE™, SURETERIC™, NUTRATERIC II®, PHTHALAVIN® (Colorcon, Inc. Harleysville, Pa.); a hydroxypropylmethylcellulose (HPMC), a high viscosity grade HPMC, or an ultra-high viscosity grade HPMC; a polyvinylpyrrolidone (PVP) or a PVP-K90; a cellulose, a microcrystalline cellulose (MCC), a methylcellulose, a hydroxy methylcellulose, a hydroxy propyl methylcellulose (HPMC), or an ethyl cellulose; a copolymer of ethyl acrylate, a poly(meth)acrylate, e.g. a methacrylic acid copolymer B, a methyl methacrylate and/or a methacrylic acid ester with quaternary ammonium groups; EUDRAGIT® RL PO™; EUDRAGIT® RL 100™ (Evonik Industries AG, Essen, Germany).

In one alternative embodiment, a compound and/or formulation of the present disclosure (including any of the compounds described herein, such as any of the compounds and/or formulations set forth in Table I of the Examples section) is formulated for oral administration and the formulation comprises a coating or otherwise comprises cellulose acetate phthalate, hydroxypropyl methylcellulose phthalate, polyvinyl acetate phthalate, hydroxypropyl methylcellulose acetate succinate, cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride, ethyl methyacrylate-methylmethacrylate-chlorotrimethylammonium ethyl acrylate copolymer, natural resins, zein, shellac, copal collophorium or an acrylic copolymer, or any combination or mixture thereof.

In alternative embodiments, a compound and/or formulation of the present disclosure (including any of the compounds described herein, such as any of the compounds and/or formulations set forth in Table I of the Examples section) is formulated for oral administration and comprises a sustained-release coating, and optionally the sustained-release coating comprises a wax mixed with a glyceryl monostearate, a stearic acid, a palmitic acid, a glyceryl monopalmitate, a cetyl alcohol, a shellac, a zein, an ethylcellulose, an acrylic resin, a cellulose acetate or a silicone elastomer or any combination or mixture thereof.

Methods and Indications

As noted above, in a third aspect the compounds described in connection with Formula (I) (or any of the embodiments thereof or other compounds described herein, such as any of the compounds and/or formulations set forth in Table I of the Examples section) can be used for treating tissue damage and/or a range of diseases and conditions. Treating diseases and conditions (including damaged tissue) as described herein may generally involve not only inhibiting the disease in a patient that is experiencing or displaying the pathology or symptomatology of the disease or condition (i.e., arresting further development of the pathology and/or symptomatology), but also ameliorating the disease or condition in a patient that is experiencing or displaying the pathology or symptomatology of the disease or condition (i.e., reversing the pathology and/or symptomatology). Treating a human patient for a disease or condition as described herein, e.g., tissue damage resulting from the administration of radiation therapy or chemotherapy, or exposure to radiation, also amounts to the inhibition or prophylaxis of such damage in a patient that is not necessarily experiencing or displaying the pathology or symptomatology of the disease or condition.

The methods of the present disclosure may advantageously be used to treat (e.g., inhibit, ameliorate, or mitigate) a variety of diseases or conditions in a variety of subjects (i.e., patients). The subject may be, for example, a mammal such as bovine, avian, canine, equine, feline, ovine, porcine, or primate (including humans and non-human primates). A subject may also include mammals of importance due to being endangered, or economic importance, such as animals raised on farms for consumption by humans, or animals of social importance to humans such as animals kept as pets or in zoos. Examples of such animals include but are not limited to: cats, dogs, swine, ruminants or ungulates such as cattle, oxen, sheep, giraffes, deer, goats, bison, camels or horses. In one embodiment, the subject is bovine, avian, canine, equine, feline, ovine, porcine, or non-human primate. In one preferred embodiment, the subject is a human patient.

Treatment of Tissue Damage

In accordance with one embodiment of the third aspect of the present disclosure, methods are described herein for treating tissue damage resulting from a cancer treatment (e.g., radiation therapy or chemotherapy) delivered to a subject in need thereof. In accordance with another embodiment, methods are described herein for treating a human patient for tissue damage resulting from exposure to radiation. Thus, in various embodiments for example, the exposure to radiation in various embodiments may be an accidental radiation exposure, an unintentional radiation exposure, or an intentional radiation exposure. As noted above, treatment of tissue damage as described herein may include both inhibition (i.e., prophylaxis) and amelioration of any tissue damage that may result from an occurrence or activity. In general, the methods involve administering to the subject a therapeutically effective amount of a compound described herein (e.g., those corresponding to Formula (I) (or any of the embodiments thereof or other compounds described herein, such as any of the compounds and/or formulations set forth in Table I of the Examples section).

Treatment of tissue damage resulting from a cancer treatment or other radiation exposure in accordance with the methods described herein involves the administration of a therapeutically effective amount of the compound described herein (e.g., those corresponding to Formula (I) (or any of the embodiments thereof or other compounds described herein, such as any of the compounds and/or formulations set forth in Table I of the Examples section). In general, a range of therapeutically effective amounts may be used, depending, for example, on the compound selected and its safety and efficacy, the type, location, and severity of the tissue damage, among other factors.

In general, the temporal aspects of the administration of the compound (e.g., those corresponding to Formula (I) (or any of the embodiments thereof or other compounds described herein, such as any of the compounds and/or formulations set forth in Table I of the Examples section) may depend for example, on the particular compound, radiation therapy, or chemotherapy that is selected, or the type, nature, and/or duration of the radiation exposure. Other considerations may include the disease or disorder being treated and the severity of the disease or disorder; activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors. For example, the compound may be administered in various embodiments before, during, and/or after the administration of the cancer therapy (e.g., radiation therapy or chemotherapy). By way of another example, the compound may be administered in various embodiments before, during, and/or after an exposure to radiation.

If desired, the effective dose can be divided into multiple doses for purposes of administration; consequently, single dose compositions may contain such amounts or submultiples thereof to make up the dose.

In one embodiment, for example, the compound (e.g., those corresponding to Formula (I) (or any of the embodiments thereof or other compounds described herein, such as any of the compounds and/or formulations set forth in Table I of the Examples section) is administered to the patient prior to or simultaneous with the cancer therapy. In another embodiment, for example, the compound (e.g., those corresponding to Formula (I) (or any of the embodiments thereof or other compounds described herein, such as any of the compounds and/or formulations set forth in Table I of the Examples section) is administered to the patient prior to, but not after, the cancer therapy. In yet another embodiment, the compound is administered to the patient at least 15 minutes, 30 minutes, 45 minutes, 60 minutes, 90 minutes, 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, prior to the cancer therapy. In still other embodiments, for example, the compound (e.g., those corresponding to Formula (I) (or any of the embodiments thereof or other compounds described herein, such as any of the compounds and/or formulations set forth in Table I of the Examples section) is administered to the patient after the cancer therapy; thus, for example, the compound may be administered up to 15 minutes, 30 minutes, 45 minutes, 60 minutes, 90 minutes, or 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, after the cancer treatment.

In another embodiment, for example, the compound (e.g., those corresponding to Formula (I) (or any of the embodiments thereof or other compounds described herein, such as any of the compounds and/or formulations set forth in Table I of the Examples section) is administered to the patient prior to or simultaneous with the radiation exposure. In another embodiment, for example, the compound (e.g., those corresponding to Formula (I) (or any of the embodiments thereof or other compounds described herein, such as any of the compounds and/or formulations set forth in Table I of the Examples section) is administered to the patient prior to, but not after, the radiation exposure. In yet another embodiment, the compound (e.g., those corresponding to Formula (I) (or any of the embodiments thereof or other compounds described herein, such as any of the compounds and/or formulations set forth in Table I of the Examples section) is administered to the patient at least 15 minutes, 30 minutes, 45 minutes, 60 minutes, 90 minutes, 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, prior to the radiation exposure. In still other embodiments, for example, the compound (e.g., those corresponding to Formula (I) (or any of the embodiments thereof or other compounds described herein, such as any of the compounds and/or formulations set forth in Table I of the Examples section) is administered to the patient after the radiation exposure; thus, for example, the compound may be administered up to 15 minutes, 30 minutes, 45 minutes, 60 minutes, 90 minutes, or 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, after the radiation exposure.

In one embodiment, for example, the cancer treatment comprises the administration of radiation therapy; for example, an intentional exposure to radiation. In accordance with this embodiment, the method provides a safe and effective method of treating radiation damage and inhibiting or ameliorating radiation-related cancers or radiation-related tissue damage in a patient in need thereof by administering to the patient a therapeutically effective amount of the compound described herein (e.g., those corresponding to Formula (I) (or any of the embodiments thereof or other compounds described herein, such as any of the compounds and/or formulations set forth in Table I of the Examples section).

In another embodiment, the exposure to radiation is an accidental or unintentional exposure. For example, the radiation exposure may result from a wide variety of commercial and non-commercial activities including, but not limited to activities in industries such as utility and power, oil/gas petrochemical, chemical/plastics, automatic ventilation control (cooking, smoking, etc.), heavy industrial manufacturing, environmental toxicology and remediation, biomedicine, cosmetic/perfume, pharmaceutical, transportation, emergency response and law enforcement, military or terrorist activities, and detection (e.g., hazardous leaks or spills). In one embodiment, for example, the exposure to radiation may result from the excavation and/or clean-up of radioactive material from air, groundwater, surface water, sediment and/or soil.

In various embodiments, the source of radiation may be electromagnetic, including visible or ultraviolet light, or nuclear, including alpha, beta, gamma, or cosmic radiation. The types of damage may include, but is not limited to, various forms of dermatological or mucosal damage, such as oral mucositis, esophagitis, and the like, as well as internal cell loss, fibrosis, cyst formation, neuropathies and various types of benign and malignant tumors.

Treatment of Diseases and Conditions

In accordance with another embodiment of the third aspect of the present disclosure, methods are described herein for treating a range of diseases and conditions modulated by superoxide in a subject in need thereof. As noted above, treatment of diseases and conditions as described herein may include both inhibition (i.e., prophylaxis) and amelioration of such disease or condition. In general, the methods involve administering to the subject a therapeutically effective amount of the compound described herein (e.g., those corresponding to Formula (I) (or any of the embodiments thereof or other compounds described herein, such as any of the compounds and/or formulations set forth in Table I of the Examples section).

In general, the temporal aspects of the administration of the compound may depend for example, on the particular compound, or the disease or condition being treated. Other considerations may include the severity of the disease or condition; activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors.

If desired, the effective dose can be divided into multiple doses for purposes of administration; consequently, single dose compositions may contain such amounts or submultiples thereof to make up the dose.

Routes of Administration

In general, the compounds described herein (or pharmaceutical compositions including the compounds) (e.g., those corresponding to Formula (I) (or any of the embodiments thereof or other compounds described herein, such as any of the compounds and/or formulations set forth in Table I of the Examples section)) can be administered to subjects (e.g., humans and other mammals) are adapted for oral administration; surprisingly, the compounds of the present disclosure are significantly more bioavailable when administered orally than other analogs, for example their bis-chloro analogs. Advantageously, therefore, the compounds of the present disclosure provide a wider range of routes of administration, including but not limited to, oral, parenteral (e.g., intravenous, intraarterial, subcutaneous, intramuscular, intraorbital, intracapsular, intraspinal, intraperitoneal, or intrasternal), topical (nasal, transdermal, buccal, ophthalmic), intravesical, intrathecal, enteral, pulmonary, intralymphatic, intracavital, vaginal, rectal, transurethral, intradermal, intraocular, aural, intramammary, orthotopic, intratracheal, intralesional, percutaneous, endoscopical, transmucosal, sublingual and intestinal administration. In one embodiment, the compound is introduced to the patient via oral administration. In another embodiment, the compound is introduced to the patient via injection, including by intravenous, subcutaneous, intramuscular, intraperitoneal, intra-arterial, and intradermal injection. Additionally or alternatively, the compounds described herein (or pharmaceutical compositions including the compounds) described herein can be administered to subjects topically (as by patches (e.g., transdermal patches), powders, lotions, ointments or drops applied to the skin), buccally, or inhaled, as an oral or nasal spray. The compounds described herein (or pharmaceutical compositions including the compounds) can also be administered to humans and other mammals intrarectally or intravaginally. In one embodiment, the compound (or a pharmaceutical composition or unit dose formulation including the compound) is administered to the subject orally. In another embodiment, the compound (or a pharmaceutical composition or unit dose formulation including the compound) is administered to the subject parenterally. It will generally be understood that parental administration refers to modes of administration which include intravenous, intramuscular, intraperitoneal, subcutaneous and intraarticular.

In some embodiments, oral administration is a preferred method of administration of the present compounds (e.g., those corresponding to Formula (I) (or any of the embodiments thereof or other compounds described herein, such as any of the compounds and/or formulations set forth in Table I of the Examples section)).

Additional Pharmaceutically Active Agents

As noted above, the above-described methods and pharmaceutical compositions including the compound may additionally include the administration of one or more pharmaceutically active agents or components. While the compounds described herein can be administered as the sole active pharmaceutical agent, they can also be used in combination with one or more compounds of the invention or other agents. When administered as a combination, the therapeutic agents can be formulated as separate compositions that are administered at the same time or sequentially at different times (e.g., one or several hours or days later), or the therapeutic agents can be given as a single composition. Thus, the disclosure is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Kits/Articles of Manufacture

For use in the therapeutic applications described herein, kits and articles of manufacture are also described. Such kits can include a carrier, package, or container that is compartmentalized to receive one or more containers such as vials, tubes, and the like, each of the container(s) including one of the separate elements to be used in a method described herein (such as, for example, the compounds corresponding to Formula (I) (or any of the embodiments thereof described herein), pharmaceutically acceptable carrier, or additional pharmaceutically active agent or compound, whether alone or in combination). Suitable containers include, for example, bottles, vials, syringes, and test tubes. The containers can be formed from a variety of materials such as glass or plastic.

Compositions containing one or more compounds provided herein (for example, the compounds corresponding to Formula (I) (or any of the embodiments thereof or other compounds described herein, such as any of the compounds and/or formulations set forth in Table I of the Examples section) formulated in a compatible pharmaceutical carrier can also be prepared, placed in an appropriate container, and labeled for treatment of an indicated condition.

In accordance with one embodiment, the article of manufacture comprises packaging material and contained within said packaging material is a an oral formulation for treating a disease or condition or for protecting tissue against damage resulting from exposure to a cancer treatment in a patient in need thereof, comprising the compounds corresponding to Formula (I) (or any of the embodiments thereof or other compounds described herein, such as any of the compounds and/or formulations set forth in Table I of the Examples section). In accordance with this embodiment, the parenteral formulation comprises a unit dose formulation as described herein, and the packaging material comprises a label or package insert with instructions for oral administering the dose to the patient. For example, the oral formulation may be in tablet, pill, capsule, or gel or suspension form and contained in a suitable vial or container.

In accordance with another embodiment, the article of manufacture comprises packaging material and contained within said packaging material is a parenteral formulation for treating a disease or condition or for protecting tissue against damage resulting from exposure to a cancer treatment in a patient in need thereof, comprising the compounds corresponding to Formula (I) (or any of the embodiments thereof or other compounds described herein, such as any of the compounds and/or formulations set forth in Table I of the Examples section). In accordance with this embodiment, the parenteral formulation comprises a unit dose formulation as described herein, and the packaging material comprises a label or package insert with instructions for parenterally administering the dose to the patient. For example, the parenteral formulation may be in solution form and contained in a suitable vial or container.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Introduction

Compounds were screened for oral bioavailability by injecting the formulated prodrugs directly into the duodenum (intraduodenal or id administration) of the minipig test subjects, thus bypassing the acidic environment of the stomach and thereby eliminating potentially misleading oral bioavailability results that could arise from alteration of the test article drug in the acid environment of the stomach.

The Gottingen minipig was selected as the test model species for assessing oral bioavailability since 1) it is well known that minipigs (and swine in general) mimic the physiology and pharmacology of the human intestine, particularly regarding drug absorption[1] and 2) previous studies in Gottingen minipig using GC4403 (the enantiomer of GC4419) demonstrated oral bioavailability consistent with the clinical experience in human studies.

The studies were conducted at Xenometrics LLC (Stillwell, Kans.) and the Id bioavailability was determined using various axial ligand derivative complexes of GC4419, GC4444, GC4403 and GC4401. In each case the parent compounds (GC4419, GC4403, GC4444, and GC4401) with their chloro axial ligands were administered by the intravenous (iv) route as a reference for calculating 100% bioavailability as measured by the $AUC_{0->24\,h}$ (area under the curve from 0 to 24 h (ng-hr/mL)). Calculation of the % oral bioavailability of a formulation of a compound administered id requires calculation of $AUC_{0->24\,h}$ via this route in comparison to that via the iv route. The following formula is then used to calculate the % oral bioavailability via intestinal absorption of the test article drug complex:

$$\% \text{ Oral Bioavailability} = AUC_{0->24\,h}(\text{id}) \times (1/\text{dose(mg/kg)}) \div AUC_{0->24\,hr}(\text{iv})^*$$

*Where the iv dose is 1 mg of test article drug per kilogram body weight of the mini-pig, and the dose administered id is 10 mg of test article drug per kg body weight of the mini-pig.

All Xenometrics facilities are fully accredited by the Association for Assessment & Accreditation of Laboratory Animals (AAALAC). All experiments and animal care were conducted within the strict guidelines established and enforced by Xenometric's Institutional Animal Care & Use Committees.

Methods

Male Gottingen minipigs (4-5 mo old, 9-12 kg weight) were purchased from Marshall BioResources and housed at Xenometrics. After at least 14 days for acclimatization, each animal had an intraduodenal (id) cannula implanted via abdominal surgery using adequate anesthesia. The distal end was exteriorized with a reusable accessible hub (see surgical details below). During a recovery period of at least 2 weeks the minipigs were handled daily to acclimate them to the test procedures, i.e., id dosing and blood collections. For each experiment, each minipig received a test article drug dissolved or suspended in an excipient vehicle. The minipigs did not require restraint for dosing. All dosing experiments were conducted in fasted animals. Food was withdrawn from the minipigs 16 hours before dosing. The minipigs had ad libitum access to water. Dosed minipigs were allowed access to food 6 hour after dosing. The test article was administered at a dose of 10 mg/kg parent drug in 0.1 m L/kg vehicle (e.g., 1.5 mL in 15 kg minipig) as a bolus injection (~1 minute) via the id cannula. The actual amount of total test article drug administered varied with the formula weight of the prodrug. An equal volume of excipient vehicle was used to flush the cannula after the test article was administered. Approximately 6 hours later, corn oil was used to flush the cannula. After approximately 24 hours post-dose, the catheter was flushed with sterile saline solution and capped. At the following time-points 0.25, 0.5, 1, 2, 4, 8, 24 and 48 hour post-injection, 2 mL blood samples were collected by cranial vena cava puncture (4 mL Sodium heparin Vacutainer, 20 g 1.5" needle) after the skin surface was wiped with ethanol. The minipig was placed in a sling in a recumbent position without anesthesia for the collection of blood samples. The minipigs were never used more than once per 7 days for experimentation. The blood samples were kept on ice until processed for plasma. Blood samples were centrifuged at 1200×g for ten minutes at 4° C. and plasma samples were transferred to 96 well plate tubes, capped and stored at −20° C. until shipment on dry ice to the analytical laboratory used for measuring the concentration of drug in the plasma. The concentration of the parent manganese pentaaza macrocylic ring complex (independent of the composition of the axial ligands) was measured in plasma using a validated HPLC/MS/MS method that is linear between 50 ng/mL and 20,000 ng/mL.

Xenometrics Surgical Procedure for Ported Duodenal Catheters in the Swine: Surgical Preparation of Test System.

Animal Preparation

The pigs are fasted overnight prior to surgery and are pre-medicated and induced according to the accompanying schedule of medications and dosages chart. An endotracheal tube is inserted and general anesthesia maintained with isoflurane delivered in oxygen via a precision vaporizer and re-breathing anesthetic circuit. LRS (Lactate-Ringers Solution) at approximately 100 mL per hour is given via a peripheral catheter during surgery. The surgery is performed in a designated surgical suite and aseptic techniques are followed throughout the surgical procedures.

Access Port (VAP) Placement

An area over the right dorsal thorax is shaved and prepped with chlorhexidine scrub and solution.

A midline laparotomy is performed with the duodenum being isolated and cannulated according to the description listed below and exteriorized at a site along the dorsal thorax. The exteriorized cannula is then attached to an individual access port (VAP) and implanted subcutaneously using an appropriate non-absorbable suture. The port incision is closed appropriately insuring the removal of dead space and the skin closed with absorbable suture. The peritoneum and muscle layer of the laparotomy will be apposed with an appropriately sized absorbable suture in an interrupted pattern. The subcutaneous tissues will be apposed with absorbable suture. The skin is closed with absorbable subcuticular suture.

Duodenal Cannulation with Vascular Access Port (VAP)

An area over the ventral abdomen is shaved and prepped with chlorhexidine scrub and solution.

A burp valve catheter with a 5 mm Dacron disk attached 1 cm from the tip (Access Technologies, Chicago Ill.) is utilized to cannulate the duodenum. The burp valve cannula is flushed prior to implantation to insure that the burp valve is free and working appropriately. The duodenum is located and the site for cannulation isolated (i.e., 5-8 cm distal to the cranial duodenal flexure). At this site, a 4-0 Prolene purse string suture is placed on the mucosal surface and the intestine perforated with an 18 g needle in the center of the purse string suture. The needle is then removed and replaced with a 16 g stub adapter to further dilate the existing insertion site. The stub adapter is then removed and the burp valve tip placed into the intestinal defect until the Dacron disc is flush with the mucosal surface. The tip is anchored by closing the purse string and tying into place. The disc is anchored into place utilizing 7-8 interrupted 4-0 Prolene sutures to the mucosal surface. A small loop is formed and the catheter body (approximately 5-6 cm from the disk) is anchored to the mucosa utilizing the Weitzel tunnel technique.

Note: The Weitzel Tunnel Technique is accomplished by placing the catheter body along the intestine with the distal aspect facing toward the cranial duodenal flexure. 4-6 individual 5-0 Prolene sutures are placed approximately 0.5 cm apart to form the "tunnel." This tunnel is formed by attaching each of the sutures to the mucosa surface beside the cannula and then attaching the free end to the mucosal surface on the other side of the cannula insuring that the suture rest on TOP of the cannula. When the individual sutures are tied they pull the mucosa over the cannula forming the "tunnel."

After completing the Weitzel Tunnel technique a small (2-3 mm) incision is made in the peritoneum approximately 1 cm below the ribs on the right side of the animal and the catheter is exteriorized to the port site by use of a trocar. An incision is made on the dorsal lateral aspect of the right thorax and a pocket formed to accept the port. The cannula is then moved to the pocket by trocar and attached to the port. The port is then anchored to the underlying musculature with an appropriately sized non-absorbable monofilament suture and the muscle, fascia, and skin closed in an appropriate manner. The port is flushed with saline. The abdomen is closed with an appropriate absorbable monofilament suture in an interrupted pattern. The fascia is closed separately with an appropriate absorbable suture in an appropriate pattern. The skin is closed in an appropriate manner with an appropriate suture or staples. During anesthetic recovery animals are monitored for a return to normal physiologic function.

Incisions sites are examined daily for 14 days minimum. Antibiotics are administered as needed. Animals are not jacketed for a minimum of 14 days post operatively.

System Maintenance

The ports are accessed using aseptic technique. Hair over the port is clipped as needed. At least 3 alternating scrubs of chlorhexidine scrub and solution are applied prior to accessing the port via a Huber pointed needle. The duodenal port is flushed with an appropriate flushing solution such as saline or sterile water after dosing.

Experimental

Preparation of Dosing Formulations

The oils used for preparing the dosing solutions were used as supplied from commercial sources. The Capmul MCM (NF) is a mixture of mono/diglycerides of caprylic/capric acids and was supplied by ABITEC Corporation, Janesville, Wis. The Miglyol 812 N is a mixture of caprylic/capric acid triglycerides and was supplied by Cremer Oleo Division, Eatontown, N.J. Labrafil M 2125 CS (NF) is chemically defined to be linoleoyl polyoxyl-6 glycerides NF and was supplied by Gattefosse, SAINT-PRIEST Cedex, France. Peceol is chemically defined to be the monoglyceride, glyceryl monooleate NF, and was supplied by Gattefosse, SAINT-PRIEST Cedex, France. Maisine 35-1 is chemically defined to be the monoglyceride glyceryl monolinoleate (NF) and was supplied by Gattefosse, SAINT-PRIEST Cedex, France. Labrasol (NF) is chemically defined to be caprylocaproyl polyoxyl-8 glycerides NF and was supplied by Gattefosse, SAINT-PRIEST Cedex, France. Labrafil M 1944 CS is chemically defined to be oleoyl polyoxyl-6 glycerides (NF), and is available from Gattefosse, SAINT-PRIEST Cedex, France. The dosing solutions were all prepared using a four place analytical balance by weighing all components of each formulation so that 10% by weight of each formulation contained the test article drug substance and 90% by weight of the oil used for that formulation.

Bioanalytical Method

The bioanalytical method which is used to quantitate the parent Mn(II) macrocyclic ring ligand structure in plasma utilizes HPLC with MS/MS detection and monitors the presence of the monocationic [monoformatoMn(pentaazamacrocycle)]+complex. All bioanalytical sample measurements were carried out at ABC Laboratories utilizing Galera's bioanalytical method validated at ABC as ABC Method Number 81201-MI-02, which is similar to the method described in U.S. Pat. No. 8,444,856 to Slomczynska et al., which is hereby incorporated by reference herein in its entirety.

Syntheses

All reagents used to synthesize compounds disclosed herein were purchased from Sigma-Aldrich and used without further purification unless otherwise indicated. All elemental analyses were performed and reported by Galbraith Laboratories, Inc. in Knoxville, Tenn.

The parent Mn(II) pentaaza macrocyclic ring dichloro complexes, such GC4419, GC4401, GC4444, and GC4403 (structures shown below) were synthesized using literature procedures. For GC4403 the chiral R,R-diaminocyclohexane is utilized as starting material,[2] whereas for GC4419, the mirror-image enantiomer of GC4403, the chiral S,S-diaminocyclohexane is utilized instead.[3,4] The remainder of the synthesis of GC4419 can be identical in all respects to the method published for GC4403.[2] The synthesis of the GC4401 complex was reported previously in reference 5.

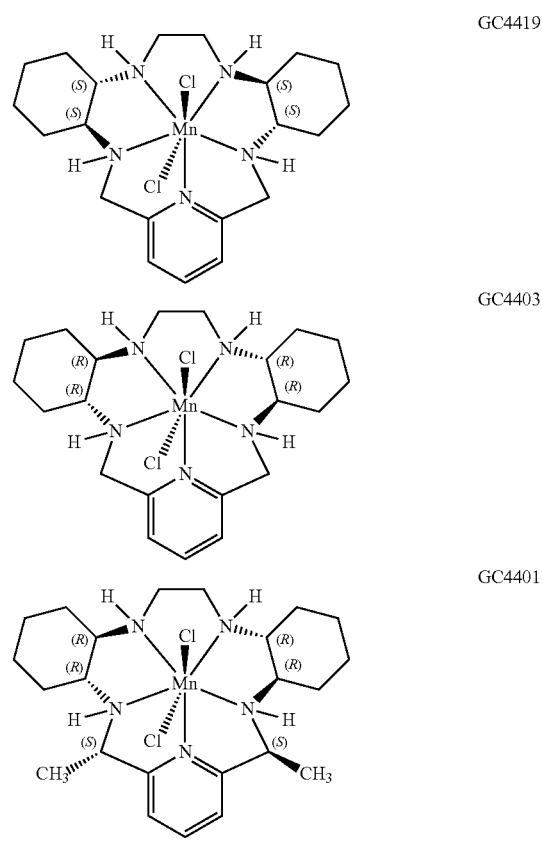

GC4419

GC4403

GC4401

GC4444

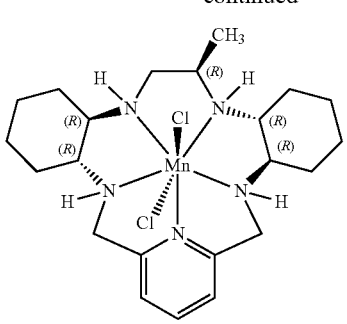

The synthesis of GC4444 which contains the additional 11-R-Methyl substituent generating a fifth chiral center on carbon (and is also derived from R,R-diaminocyclohexane) is made from the corresponding chiral tetraamine whose synthesis was published in reference 6 as Example 5C.

Syntheses of Axial Ligand Derivatives

The same parent Mn(II) pentaaza macrocyclic ring dichloro complexes (GC4419, GC4403, GC4444 and GC4401) were also used as the starting material precursors for the syntheses of other axial ligand bound derivatives using a generic synthesis scheme in which a large excess of a salt of an anion is used to displace the chloro ligand thereby generating the new compound.

Example 2

Synthesis of Manganese(II)bis-acetato[(4aS,13aS, 17aS,21aS)-1,2,3,4,4a,5,6,12,13,13a,14,15,16,17, 17a,18,19,20,21,21a-Eicosahydro-11,7-nitrilo-7H-dibenzo[b,h][1,4,7,10] tetraazacycloheptadecine-κN5,κN13,κN18,κN21,κN22]-, [bis-Acetato (GC4419)]. GC4701

GC4701

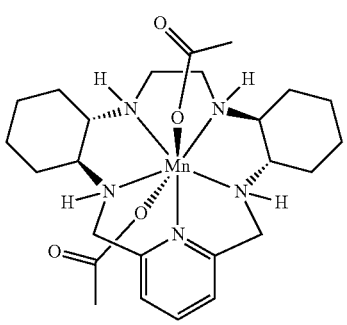

[Bis-Acetato(GC4419)]
$C_{25}H_{41}MnN_5O_4$
MW 530.57

Using a 500-mL Erlenmeyer, 100 mL of deionized ("DI") water was added to 5.3 g of GC4419; the mixture was stirred vigorously for 15-20 min, then sonicated for 5 min. The resulting light brownish suspension was filtered through a 10-20μ fritted funnel (ca. 0.3 g of solid material remained in the funnel). The resulting clear solution was added into a sodium acetate solution (ca. 429 mmol, 21 equiv in 100 mL DI water) as a stream in one portion. No solid separated and the yellowish solution was stirred for 5 additional min. The solution was transferred to a separatory funnel and extracted (3×50 mL) with dichloromethane. The organic layers were separated, combined, and transferred back into a separatory funnel. The dichloromethane solution was back-extracted (2×50 mL) with aqueous sodium acetate (32 g/100 mL). The dichloromethane layer was dried over $MgSO_4$ (ca. 10 g) for 30 min (w/stirring), filtered using a 10-20μ fritted funnel, and the solution taken to dryness using a rotavap. To the yellow oily solid resulting from taking the solution to dryness was added methanol (50 mL). This solution was then again taken to dryness on the rotovap to yield a light yellow foam/glass. This material was dried in vacuo at room temperature for two days.

The isolated yellowish brittle (4.11 g, 75% yield based on GC4419) was analyzed by HPLC and showed a purity of 99.7% and elemental analysis showed 0.98 wt. % residual chlorine. The elemental analysis is consistent with the expected bis-(acetato) structure $C_{25}H_{41}MnN_5O_4 \cdot 2H_2O$. Anal Cal'd: C, 53.00%; H, 8.01%; N, 12.36%; and Mn, 9.70%. Anal Found: C, 53.10%; H, 8.34%; Mn, 9.86%; N, 12.56%; and Cl (as total halogen content), 0.98 wt. %.

Example 3

Synthesis of Manganese(II)bis-octanoato[(4aS,13aS, 17aS,21aS)-1,2,3,4,4a,5,6,12,13,13a,14,15,16, 17,17a,18,19,20,21,21a-Eicosahydro-11,7-nitrilo-7H-dibenzo[b,h][1,4,7,10] tetraazacycloheptadecine-κN5, κN13, κN18, κN21, κN22]-, [bis-Octanoato (GC4419)]. GC4710

GC4710

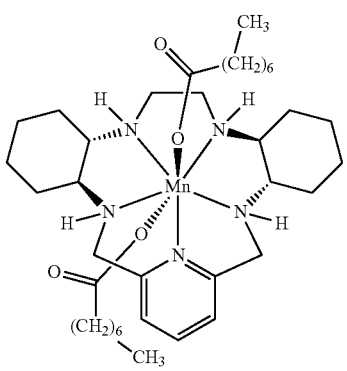

[Bis-Octanoato(GC4419)]
$C_{37}H_{65}MnN_5O_4$
MW 698.90

Using a 500-mL Erlenmeyer, 200 mL of DI water was added to 10.2 g of GC4419, stirred vigorously for 15-20 min, then sonicated for 5 min. The resulting tan suspension was filtered through a 45×20 mm bed of celite (pre-washed with DI water) on a 25-50μ fritted funnel. The resulting clear solution was added to 250 mL of a solution of sodium octanoate (75 g, ca. 450 mmol, 11 equiv) as a slow stream over 5 min. No solid separated and the tan solution was stirred for an additional 5 min. The solution was transferred to a separatory funnel and extracted (2×100 mL) with DCM. The organic layers were separated, combined, dried over $MgSO_4$ (10 g), filtered, and rendered dry under reduced pressure. MeOH (75 mL) was used to co-evaporate residual DCM to yield a light yellow-tan gum. This gum was dried in vacuo at 40° C. for 19 h. A yellowish solid was isolated in 73% yield (10.8 g) based on starting GC4419. This solid was submitted for elemental analysis (Galbraith Labs) and also analyzed by HPLC using the chromatography method described in reference 4.

HPLC showed a purity of 99.5% (0.14% monoamine GC4520). Elemental analysis is consistent with the structure as a hemihydrate $C_{25}H_{41}MnN_5O_4 \cdot 0.5\ H_2O$, FW 734.93 (anhyd). Anal Cal'd: C, 63.05%; H, 9.39%; N, 9.94%; and Mn, 7.79%. Anal Found: C, 63.21%; H, 9.80%; Mn, 7.97%; N, 9.63%; and Cl (as total halogen content), <150 ppm.

Example 4

Synthesis of Manganese(II)bis-pivaloato[(4aS,13aS,17aS,21aS)-1,2,3,4,4a,5,6,12,13,13a,14,15,16,17,17a,18,19,20,21,21a-Eicosahydro-11,7-nitrilo-7H-dibenzo[b,h][1,4,7,10] tetraazacycloheptadecine-κN5, κN13, κN18, κN21, κN22]-, [bis-Pivaloato (GC4419)]. GC4709

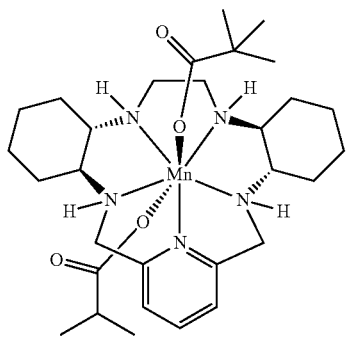

[Bis-Pivaloato(GC4419)]
$C_{31}H_{53}MnN_5O_4$
MW 614.73

The sodium pivaloate salt (6.4 g) was added to a 125 mL Erlenmeyer flask and dissolved (warmed to ca. 40° C.) in 50 mL of abs EtOH (solution was nearly colorless). Once the sodium pivaloate solution was cooled back to room temperature, a solution containing 5.3 g of GC4419, dissolved in 30 mL of abs EtOH (solution was tan in color), was added. Precipitation of NaCl was observed immediately upon mixing. The light, tan suspension was stirred for 1 h, at rt and under Ar, then placed in a refrigerator (2-8° C.) overnight. The resulting light, tan suspension was filtered using a tared 10-20μ fritted funnel (ca. 1.1 g of solid sodium chloride salt remained in the funnel) and the solvent stripped off the filtrate using a rotavap. The wet residue from the rotavap was further dried in vacuo for 15 min. IPA (100 mL) was added and the mixture swirled for one hour then placed in the refrigerator overnight. The next day, upon filtering, 1.28 g of white solid was isolated and discarded. The clear tan-yellow filtrate was rendered a wet solid using a rotavap.

Dichloromethane (100 mL) was added to the wet solid. The mixture turned into a gel-like suspension and was mixed with stirring for 1 h at 37° C. The suspension was filtered using a tared 10-20μ fritted funnel and 1.7 g of additional white solid was isolated and discarded. The filtrate's solvent was removed using a rotavap to yield a tan syrup. MeOH (75 mL) was added to the tan syrup and after solvent removal via a rotavap to yield a tan semisolid. This material was dried in vacuo for 72 h to afford GC4709 as a tan solid which was submitted for elemental analysis. HPLC showed a purity of 99.5%. Elemental analysis is consistent with the structure $C_{31}H_{53}MnN_5O_4 \cdot 0.5\ H_2O$, FW 614.73 (anhyd). Anal Cal'd: C, 59.69%; H, 8.73%; N, 11.23%; and Mn, 8.81%. Anal Found: C, 59.87%; H, 8.44%; Mn, 8.45%; N, 10.88%; and Cl (as total halogen content), ca. 0.08% (784 ppm).

Example 5

Synthesis of Manganese(II)bis-cyclohexanebutyrato [(4aS,13aS,17aS,21aS)-1,2,3,4,4a,5,6,12,13,13a,14,15,16,17,17a,18,19,20,21,21a-Eicosahydro-11,7-nitrilo-7H-dibenzo[b,h][1,4,7,10] tetraazacyclo-heptadecine-κN5, κN13, κN18, κN21, κN22]-, [bis-Cyclohexanebutyrato(GC4419)]. GC4707

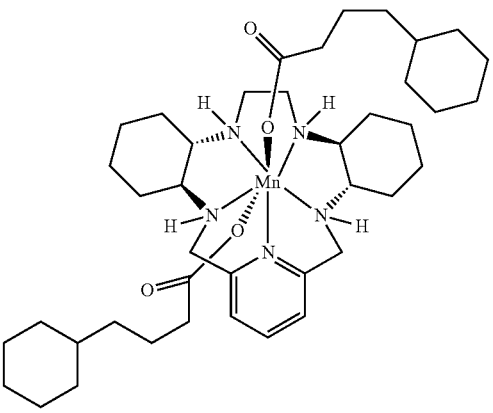

[Bis-Cyclohexanebutyratio(GC4419)]
$C_{41}H_{69}MnN_5O_4$
MW 750.97

Sodium cyclohexanebutyrate (5.77 g) was added to a 125 mL Erlenmeyer flask and then an attempt was made to dissolve it in 50 mL of abs EtOH over 15 min with stirring. The mixture turned gel-like and 50 mL of additional EtOH (abs), for 100 mL total, was added. This extra solvent did not afford a clear solution upon warming/sonicating (ca. 40° C.). MeOH (10 mL) was added and upon 15 min of stirring/sonicating a clear solution resulted. This solution was added in one portion to a solution containing 3.6 g of GC4419 dissolved in 15 mL of abs EtOH (solution was tan in color). A fine suspension resulted immediately. The suspension was stirred for 15 min and then placed in a freezer for 1 h. At this point the suspension was filtered using a 10-15μ fritted funnel and the clear tan filtrate evaporated to dryness on a rotavap. The resulting solid was dried in vacuo at room temperature overnight. The next morning, the tan solid was stirred in 100 mL of dichloromethane ("DCM") to dissolve the desired product while leaving the excess sodium cyclohexanebutyrate salt. This slurry was stirred for 3 h prior to filtration (using a 10-15μ fritted funnel and washed in-funnel using 2×30 mL DCM). The resulting yellow filtrate was evaporated using a rotavap and 100 mL of MeOH was then added. The resulting yellow solution was again evaporated using a rotavap and the residue left in vacuo at room temperature overnight. The next day, a tan solid was isolated. The material was broken down further and dried in vacuo overnight, and then ground using an agate mortar/pestle.

The isolated tan solid (5.4 g, 96% yield based on GC4419) was analyzed by HPLC and showed a purity of 99.6%. Elemental analysis was consistent with [bis-(Cyclohexanebutyrato)GC4419]: $C_{41}H_{69}MnN_5O_4$, FW 750.97 (anhyd). Anal Cal'd: C, 65.58%; H, 9.26%; N, 9.33%; and Mn, 7.32%. Anal Found: C, 65.29%; H, 8.83%; Mn, 6.95%; N, 9.42%; and Cl (as total halogen content) of 0.22 wt. %.

Example 6

Synthesis of Manganese(II)bis-dodecanoato[(4aS, 13aS,17aS,21aS)-1,2,3,4,4a,5,6,12,13, 13a,14,15,16, 17,17a,18,19,20,21,21a-Eicosahydro-11,7-nitrilo-7H-dibenzo[b,h][1,4,7,10] tetraazacycloheptadecine-κN5, κN13, κN18, κN21, κN22]-, [bis-Dodecanoato (GC4419)]. GC4708

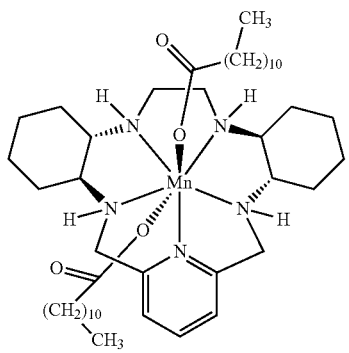

[Bis-Dodecanoato(GC4419)]
$C_{45}H_{81}MnN_5O_4$
MW 811.11

Sodium dodecanoate (6.17 g) was added to 300 mL of abs EtOH in a 500 mL Erlenmeyer flask. The resulting white suspension was stirred (300 rpm) while warming (ca. 50° C.) on a hot-plate. After 15 min the suspension actually thickened somewhat. An additional 100 mL of Abs. EtOH was added and the resultant slurry was sonicated for 10 min. 15 mL of DI water was then added (making it ca. 96% EtOH) with stirring and the mixture turned into a clear solution within a minute. To this solution, 3.6 g of GC4419 dissolved in 30 mL abs EtOH was added. The resulting solution was cloudy and light tan in color, and was stirred for 2 h and then placed on a rotavap. Approximately half of the solvent was removed, with a solid material coming out of solution as the volume decreased. At this point both solid and solvent were transferred to a 25-50μ filter funnel, along with a EtOH (50 mL) rinse of the flask, and filtered. The light tan filtrate was then placed again in the rotavap. Upon further evaporation, a light tan solid resulted, which was placed in vacuo at room temperature overnight. The next day, ca. 4.7 g of tan solid was isolated. DCM (100 mL) was added and the suspension stirred for 1 h, then filtered to afford a light yellow filtrate. Upon removal of the DCM using a rotavap, a light tan foam resulted which was further dried in vacuo at room temperature for 48 h.

The tan brittle solid (2.9 g, 44% yield) was analyzed by HPLC and showed a purity of 96.8%.

Example 7

Synthesis of Manganese(II)bis-phenylacetato[(4aS, 13aS,17aS,21aS)-1,2,3,4,4a,5,6,12,13,13a,14, 15,16, 17,17a,18,19,20,21,21a-Eicosahydro-11,7-nitrilo-7H-dibenzo[b,h][1,4,7,10] tetraazacycloheptadecine-κN5, κN13, κN18, κN21, κN22]-, [bis-Phenylacetato(GC4419)]. GC4718

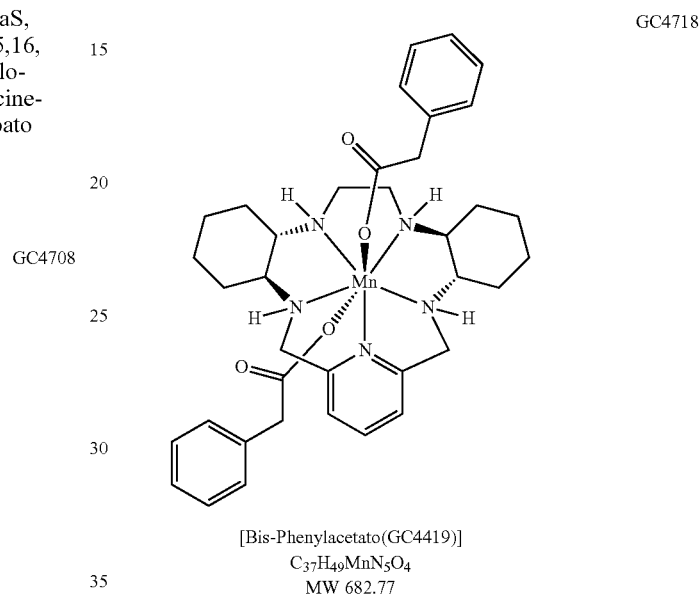

[Bis-Phenylacetato(GC4419)]
$C_{37}H_{49}MnN_5O_4$
MW 682.77

Phenylacetic acid (47.3 g) was partially dissolved in DI water (1 L), and titrated to pH 7.6 using solid NaOH, followed by drop-wise addition of 0.5 M solution of NaOH in water to bring the pH to about 8.5. The final volume of sodium phenylacetate solution was about 1 L. GC4419 was added as a solid (3.5 g) to 400 mL of the phenylacetate solution with stirring, whereupon some solids formed. DCM (50 mL) was added and the aqueous layer extracted. This extraction was repeated two additional times with all three dichloromethane extracts being pooled (ca. 150 mL) and back-extracted with the remaining phenylacetate solution (4×150 mL). The light yellow DCM solution was dried over $MgSO_4$ for 30 min (with stirring), filtered using a 10-20μ fritted funnel, and rendered dry in a rotavap. The resulting foam was dissolved in 50 mL of MeOH and rendered dry again to remove trace of DCM. The yellow foam residue was placed in vacuo at room temperature overnight. 4.57 g (93% yield) of the pale tan-yellow semi-crystalline solid was isolated, analyzed by HPLC and showed a purity of 99.6%. The elemental analysis is consistent with the expected bis-(phenylacetato) structure $C_{37}H_{49}MnN_5O_4$. Anal Cal'd: C, 65.09%; H, 7.23%; N, 10.26%; and Mn, 8.05%. Anal Found: C, 65.17%; H, 7.26%; Mn, 7.67%; N, 10.08%; and Cl (as total halogen content), 63 ppm.

Example 8

Synthesis of Manganese(II)bis-phenylglyoxaloto [(4aS,13aS,17aS,21aS)-1,2,3,4,4a,5,6,12,13,13a,14, 15,16,17,17a,18,19,20,21,21a-Eicosahydro-11,7-nitrilo-7H-dibenzo[b,h][1,4,7,10] tetraazacyclo-hepta-decine-κN5, κN13, κN18, κN21, κN22]-, [bis-Phenylglyoxylato(GC4419)]. GC4719

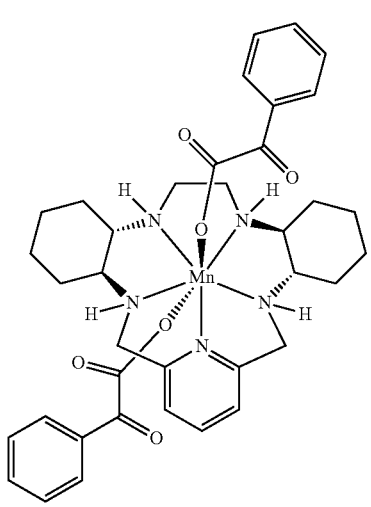

[Bis-Phenylglyoxylato(GC4419)]
$C_{37}H_{45}MnN_5O_6$
MW 710.73

Phenylglyoxylic acid (12.4 g) was added to 200 mL of DI water in a 500 mL Erlenmeyer flask. After stirring for 5 min, a clear, colorless solution resulted. This was treated with 3.2 g of NaOH as pellets and the mixture stirred vigorously. The pH was measured when all NaOH had dissolved. The pH was 3.61 and was adjusted to ~8.5-9 using 5 wt % aqueous NaOH.

A hazy solution of 5 g of GC4419 in 75 mL of DI water was filtered through a 10-20μ filter funnel and added in one portion to ca. one half of the pH-adjusted aqueous solution (ca. 110 mL) of sodium phenylglyoxylate. The precipitated white material was stirred for an additional 15 min before adding 100 mL of DCM. A yellow DCM layer resulted immediately. The layers were separated and the DCM layer was extracted with the second half of the sodium phenylglyoxylate solution. After shaking vigorously and allowing to settle for 10 min., the DCM layer was dried over $MgSO_4$, filtered and the solvent removed using a rotavap. MeOH (50 mL) was added to the rotavap flask and the yellow solution further evaporated to remove residual DCM. The resulting solid was dried in vacuo at 30° C. overnight.

The isolated light yellow semi-crystalline solid (7.1 g, 96% yield from GC4419) was analyzed by HPLC and showed a purity of 99.3%. Elemental analysis showed the following: C, 62.05%; H, 6.38%; Mn, 7.73%; and N, 9.85%. Anal Found: C, 62.50%; H, 6.29%; Mn, 7.73%; N, 9.85%; and Cl as total halogen content of 55 ppm.

Example 9

Synthesis of Manganese(II)bis-propionato[(4aS, 13aS,17aS,21aS)-1,2,3,4,4a,5,6,12,13,13a,14,15,16, 17,17a,18,19,20,21,21a-Eicosahydro-11,7-nitrilo-7H-dibenzo[b,h][1,4,7,10] tetraaza-cycloheptadecine-κN5, κN13, κN18, κN21, κN22]-, [bis-Propionato(GC4419)]. GC4711

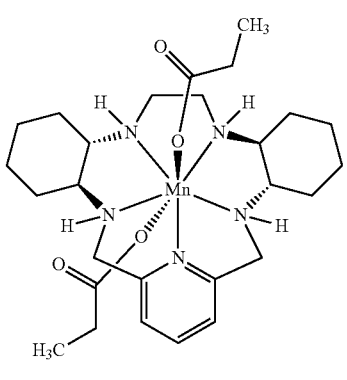

[Bis-Proplonato(GC4419)]
$C_{27}H_{45}MnN_5O_4$
MW 558.63

GC4419 (11.0 g) was added to a 500-mL Erlenmeyer flask containing 200 mL of DI water. The mixture was stirred vigorously for 15-20 min with warming to 40° C. for 10 min. The resulting light, brownish suspension was filtered using a 10-20μ fritted funnel to afford a clear, light tan solution. In a separate flask was prepared an aqueous solution of 80 g sodium propionate in 200 mL of DI water. In a 500-mL Erlenmeyer flask the GC4419 solution and 200 mL of the sodium propionate solution were combined. The resulting tan solution was stirred for 5 min. The light tan-yellow solution was transferred to a 1-L separatory funnel and extracted with DCM (3×75 mL). The three resulting DCM layers were combined, and transferred back into a separatory funnel and the resulting DCM solution was back-extracted with additional aqueous sodium propionate solution (3×70 mL). The DCM layer was dried over $MgSO_4$ for 15 min (w/stirring), filtered using a 20-50μ fritted funnel, and rendered dry (i.e., foam) using a rotavap. Methanol (100 mL) was added and the resulting solution dried using a rotavap to remove residual DCM to yield a light tan-yellow solid. This material was dried in vacuo at 30° C. for 20 h.

There was obtained 11.45 g of the isolated yellowish solid corresponding to 94% yield based on GC4419. HPLC analysis showed a purity of 99.6% and the elemental analysis showed only 873 ppm residual chloride expressed as total halogen content and consistent with the [bis-Propionato (GC4419)] structure. Anal Calc'd: C, 58.05%; H, 8.12%; Mn, 9.83%; and N, 12.54%. Anal Found: C, 57.64%; H, 8.05%; Mn, 9.91%; N, 12.51%; and Cl as total halogen content of 873 ppm.

Example 10

Synthesis of Manganese(II)bis-L-phenylglycinato [(4aS,13aS,17aS,21aS)-1,2,3,4,4a,5,6,12,13,13a,14,15,16,17,17a,18,19,20,21,21a-Eicosahydro-11,7-nitrilo-7H-dibenzo[b,h][1,4,7,10] tetraazacyclo-heptadecine-κN5, κN13, κN18, κN21, κN22]-, [bis-(L)-Phenylglycinato(GC4419)]. GC4702

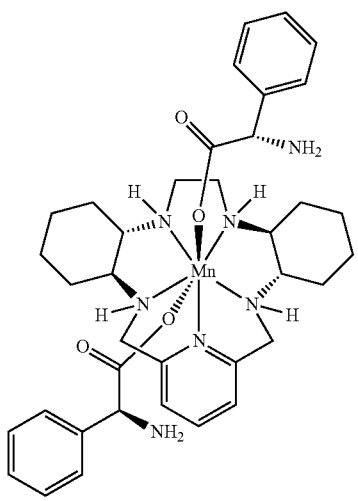

GC4702

[Bis-(L)-Phenylglycinato(GC4419)]
$C_{37}H_{51}MnN_7O_4$
MW 712.80

GC4419 (1.5 g) was added to a 250 mL Erlenmeyer flask containing 100 mL of DI water with stirring for 15 minutes. The resulting light, brownish suspension was filtered using a 20-50μ fritted funnel. To a second Erlenmeyer flask, in which 31.3 g of L-phenylglycine was dissolved in 400 mL of DI water, was added 8.3 g of NaOH as pellets and the mixture stirred vigorously. The pH was measured when all NaOH had dissolved. The pH was 2.30 and was adjusted using 5 wt. % aqueous NaOH (resulting pH=9.6). In a 250-mL Erlenmeyer flask the GC4419 solution and approximately one-half (200 mL) of the sodium L-phenylglycine solution, were combined. The resulting tan solution was stirred for 5 min. The light tan-yellow solution was transferred to a 1-L separatory funnel and extracted with DCM (3×50 mL). The three resulting DCM layers were combined, and transferred back into a separatory funnel. The resulting DCM solution was back-extracted with the remaining aqueous sodium L-phenylglycine solution (4×50 mL). The DCM layer was dried over MgSO₄ for 15 min (w/stirring), filtered using a 20-50μ fritted funnel, and dried using a rotavap. Methanol (50 mL) was added and the resulting solution dried using a rotavap to remove residual DCM to yield a light tan-yellow solid. This material was dried in vacuo at 30° C. for 20 h. 5.42 g of the isolated yellowish solid (74% yield) was obtained. Analysis by HPLC showed a purity of 99.5%. Elemental analysis showed 188 ppm of residual chloride. The elemental analysis was consistent with the expected GC4702 structure as a 1.5 hydrate: $C_{37}H_{51}MnN_7O_4 \cdot 1.5$ H₂O, Anal Calc'd: C, 60.07%; H, 7.36%; Mn, 7.43%; and N, 13.25%. Anal Found: C, 60.20%; H, 7.11%; Mn, 7.72%; N, 13.30%; and Cl as total halogen content 188 ppm.

Example 11

Synthesis of Manganese(II)bis-racemic-phenylglycinato[(4aS,13aS,17aS,21aS)-1,2,3,4,4a,5,6,12,13,13a,14,15,16,17,17a,18,19,20,21,21a-Eicosahydro-11,7-nitrilo-7H-dibenzo[b,h][1,4,7,10] tetraazacycloheptadecine-κN5, κN13, κN18, κN21, κN22]-, [bis-(rac)-Phenylglycinato(GC4419)]. GC4720

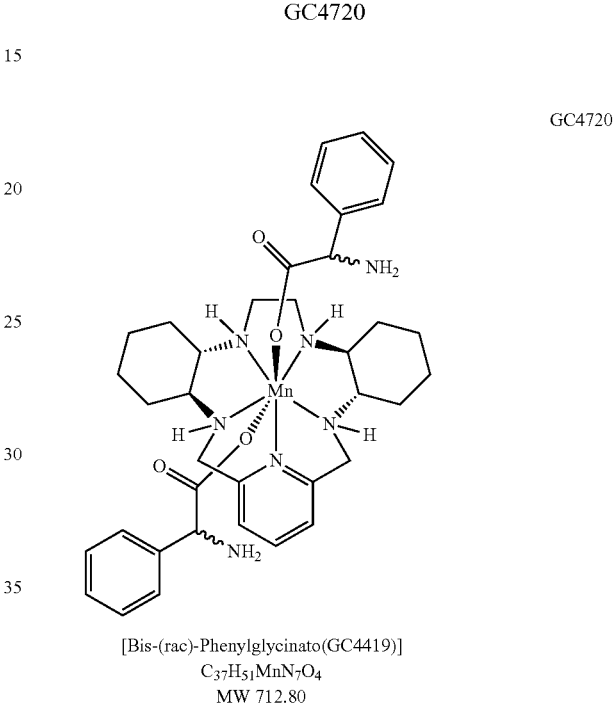

GC4720

[Bis-(rac)-Phenylglycinato(GC4419)]
$C_{37}H_{51}MnN_7O_4$
MW 712.80

GC4419 (10.0 g) was added to 250 mL of DI water in a 500 mL Erlenmeyer flask with vigorous stirring for 15-20 min. The resulting light, brownish suspension was filtered through a 20-50μ fritted funnel. To a second Erlenmeyer flask containing 62.7 g of rac-phenylglycine in 350 mL of DI water, was added 16.6 g of NaOH (two ca. equal portions as pellets) and the mixture stirred vigorously. The pH was measured when all NaOH had dissolved and a clear solution had been obtained. The pH was measured as 12.3, and was adjusted to 9 by adding small portions of racemic-phenylglycine powder. The GC4419 solution and half (~200 mL) of the sodium racemic-phenylglycinate solution (ca. 105 mmol) were combined in a 500 mL Erlenmeyer flask. The resulting light brown solution was stirred for 5 min. The solution was transferred to a 1-L separatory funnel, and extracted with 150 mL of DCM. The organic layer was separated and back-extracted with the remaining aqueous sodium racemic-phenylglycinate (2×100 mL). The DCM layer was dried over MgSO₄ for 15 min (w/stirring), filtered using a 20-50μ fritted funnel, and rendered dry using a rotavap. Methanol (75 mL) was added and the resulting solution dried using a rotavap to remove residual DCM to yield a light tan-yellow solid. This material was dried in vacuo at 30° C. for 20 h. The isolated yellowish material (5.42 g, 74% yield) was analyzed by HPLC showing 99.5% purity. The elemental analysis is consistent with the expected GC4720 structure $C_{37}H_{51}MnN_7O_4 \cdot 2H_2O$. Anal Cal'd: C, 62.35%; H, 7.21%; N, 13.76%; and Mn, 7.71%. Anal Found: C, 56.89%; H, 7.02%; Mn, 7.68%; N, 13.76%; and Cl (as total halogen content), 0.20%.

Example 12

Synthesis of Manganese(II)bis-L-phenylalaninato [(4aS,13aS,17aS,21aS)-1,2,3,4,4a,5,6,12,13,13a,14, 15,16,17,17a,18,19,20,21,21a-Eicosahydro-11,7-nitrilo-7H-dibenzo[b,h][1,4,7,10] tetraazacycloheptadecine-κN5, κN13, κN18, κN21, κN22]-, [Bis-(L)-Phenylalaninato(GC4419)]. GC4704

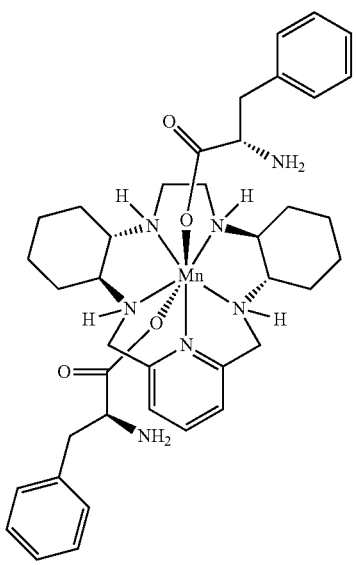

[Bis-(L)-Phenylalaninato(GC4419)]
$C_{39}H_{55}MnN_7O_4$
MW 740.85

GC4419 (10.0. g) was added to 200 mL of DI water in a 500 mL Erlenmeyer flask with vigorous stirring. The resulting light, brownish suspension was filtered using a 20-50μ fritted funnel. Separately, (L)-phenylalanine (68.39 g) was added to 200 mL of DI water in a 500-mL Erlenmeyer flask. The phenylalanine suspension was treated with solid NaOH (16.6 g) as pellets, and the mixture stirred vigorously. The pH was measured when all NaOH had dissolved. The pH was 11.1 and was adjusted down to pH=10.24 by addition of L-phenylalanine. The GC4419 solution and half (ca. 100 mL) of the sodium L-phenylalanine solution were combined in a 500 mL Erlenmeyer flask with stirring. The resulting tan solution was stirred for 5 min after having added 100 mL of DCM. The light tan-yellow biphasic solution was transferred to a 1-L separatory funnel, the organic layer removed and the aqueous layer extracted with an additional 50 mL of DCM. The organic layers were combined, and transferred back into the separatory funnel. The resulting DCM solution was back-extracted with the remaining aqueous sodium propionate solution (2×ca. 50 mL). The DCM layer was dried over $MgSO_4$ for 15 min (w/stirring), filtered using a 20-50μ fritted funnel, and rendered dry (i.e., foam) using a rotavap. Methanol (50 mL) was added and the resulting solution dried using a rotavap to remove residual DCM to yield a light tan-yellow solid. This material was dried in vacuo at 30° C. for 40 h.

The isolated tan-yellow amorphous powder (4.1 g, 55% yield) was analyzed via HPLC and shown to have a purity of 99.6%. Elemental analysis was consistent with the expected structure of the GC4704 complex as a trihydrate, $C_{39}H_{55}MnN_7O_4 \cdot 3H_2O$, showing the following results: C, 59.19%; H, 7.22%; Mn, 6.52%; N, 12.09%; and Cl, 0.20%.

Example 13

Synthesis of Manganese(II)bis-racemic-2-phenyl-propionato[(4aS,13aS,17aS,21aS)-1,2,3,4,4a,5,6,12, 13,13a,14,15,16,17,17a,18,19,20,21,21a-Eicosa-hydro-11,7-nitrilo-7H-dibenzo[b,h][1,4,7,10] tetraazacycloheptadecine-κN5, κN13, κN18, κN21, κN22]-, [bis-(rac)-2-Phenylpropionato(GC4419)]. GC4705

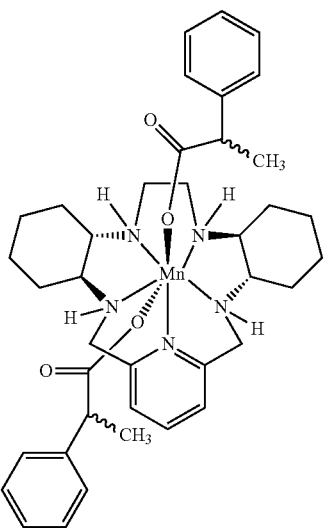

[Bis-(rac)-2-Phenylpropionato(GC4419)]
$C_{39}H_{53}MnN_5O_4$
MW 710.82

27.5 g of the racemic-2-phenylpropionic acid was added to a 500-mL Erlenmeyer containing 200 mL of DI water. After stirring for 5 min, a dispersion resulted. It was treated with solid NaOH (6.84 g) as pellets and the mixture stirred vigorously. The pH was measured when all NaOH had dissolved. Prior to NaOH addition the pH was 2.97 (dispersion) and subsequent to addition it was adjusted to pH ~9 using 5 wt. % aqueous NaOH resulting in a slightly turbid solution. A faintly hazy solution of 10 g of GC4419 in 350 mL of DI water was prepared by stirring vigorously. A 100-mL portion of the pH-adjusted aqueous solution of the 2-phenylpropionate solution was added as a slow stream over one min. An off-white semisolid precipitated, and the entire mixture was stirred with DCM (100 mL) for 15 min. After this period, the two phase solution was transferred into a 500-mL separatory funnel. DCM (10 mL) was used to rinse the Erlenmeyer flask and added to the funnel. The organic layer was separated and the top aqueous layer extracted with an additional dichloromethane (50 mL). The tan colored dichloromethane solutions were combined in the separatory funnel and were extracted with the second half of aqueous sodium rac-phenylpropionate solution (2×50 mL). After shaking vigorously and settling for 10 min each time, the DCM layer was dried over $MgSO_4$ (20 g) filtered and the solvent removed. Methanol (75 mL) was added and the resulting solution dried using a rotavap to remove residual DCM. The resulting gummy material was dried in vacuo at 35° C. overnight.

The isolated faint beige solid (14.6 g, 95% yield) was analyzed by HPLC, and showed a purity of 99.7%. Elemental analysis is consistent with that expected for GC4705, $C_{39}H_{53}MnN_5O_4$: C, 65.74%; H, 7.54%; Mn, 7.57%; N, 9.76%; and Cl, 60 ppm.

Example 14

Synthesis of Manganese(II)bis-racemic-phenylglycinato[2S, 21S-Dimethyl(4aR,13aR,17aR,21aR)-1,2,3,4,4a,5,6,12,13,13a,14,15,16,17,17a,18,19,20,21,21a-Eicosahydro-11,7-nitrilo-7H-dibenzo[b,h][1,4,7,10]tetraazacycloheptadecine-κN5, κN13, κN18, κN21, κN22]-, [bis-(rac)-Phenylglycinato(GC4401)]. GC4715

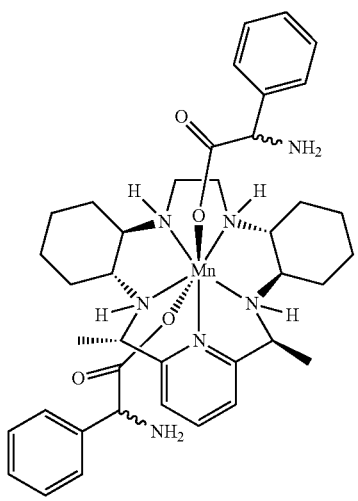

[Bis-(rac)-Phenylglycinato(GC4401)]
$C_{39}H_{55}MnN_7O_4$
MW 740.85

GC4401 (5 g, 9.78 mmol) was added to 50 mL of DI water in a 125 mL Erlenmeyer flask and stirred vigorously for 5 min to afford a very slightly turbid yellowish solution. This solution was then filtered and the filtrate solution retained. Using a second Erlenmeyer flask, the racemic-phenylglycine (30 g, 198.5 mmol) was added to 200 mL of DI water to afford a colorless solution. This solution was treated with 7.9 g of NaOH as pellets and the mixture stirred vigorously. The pH was measured after all the NaOH had dissolved and found to be 11.2. The slightly turbid solution was filtered (20-50μ). In a 250-mL Erlenmeyer flask, the GC4401 solution and half (100 mL) of the sodium phenylglycinate solution (ca. 105 mmol/10 equiv) were combined in one stream. No solid separated and the resultant yellow-tan solution was stirred for 15 additional min, then transferred to a 250-mL separatory funnel, and extracted with dichloromethane (50 mL, about 1-2 min shaking time). The organic layer was separated and transferred back onto the separatory funnel. This dichloromethane solution was back-extracted with the remaining aqueous sodium phenylglycinate (1-2 min shaking each time). The dichloromethane layer was dried over $MgSO_4$ for 15 min, filtered using a 20-50μ fritted funnel, and rendered dry (i.e., foam) using a rotavap. Methanol (50 mL) was then added to the yellow solid and the solution taken to dryness in order to co-evaporate residual dichloromethane yielding a light yellow solid. This material was dried in vacuo at 30° C. for 24 h. The isolated yellowish solid (6.5 g, 90% yield based on GC4401) was analyzed by HPLC and showed a purity of 99.5%. The elemental analysis is consistent with the expected GC4715 structure $C_{39}H_{55}MnN_7O_4.H_2O$. Anal Cal'd: C, 63.23%; H, 7.48%; N, 13.23%; and Mn, 7.42%. Anal Found: C, 60.68%; H, 7.31%; Mn, 7.06%; N, 12.68%; and chlorine (as total halogen content), 974 ppm.

Example 15

Synthesis of Manganese(II)bis-racemic-phenylglycinato[6R-Methyl(4aR,13aR,17aR,21aR)-1,2,3,4,4a,5,6,12,13,13a,14,15,16,17,17a,18,19,20,21,21a-Eicosahydro-11,7-nitrilo-7H-dibenzo[b,h][1,4,7,10]tetraazacycloheptadecine-κN5, κN13, κN18, κN21, κN22]-, [bis(rac) 2-Phenylglycinato(GC4444)]. GC4716

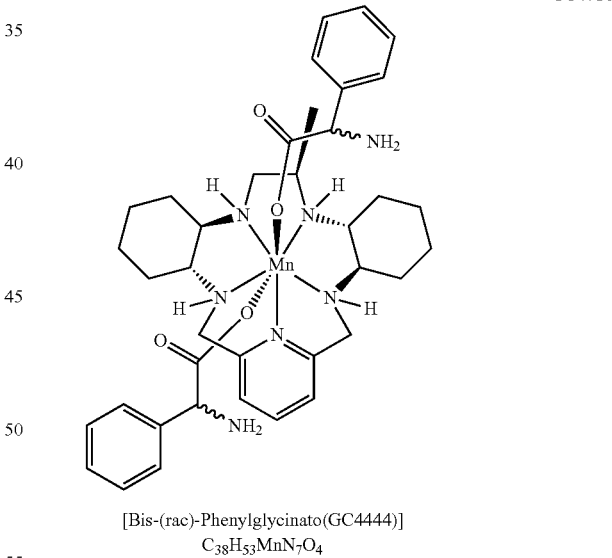

[Bis-(rac)-Phenylglycinato(GC4444)]
$C_{38}H_{53}MnN_7O_4$
MW 726.83

GC4444 (1 g, 2 mmol) was added 40 mL of DI water in a 125 mL Erlenmeyer flask and stirred vigorously for 5 min to afford a light yellow solution. In a second 250 mL Erlenmeyer flask, racemic-phenylglycine (6 g, 40 mmol) was added to 100 mL of DI water to afford a colorless solution. The solution was treated with NaOH pellets (1.6 g) and the mixture stirred vigorously. The pH was measured when all NaOH had dissolved and found to be 12.

In a 250-mL Erlenmeyer flask the GC4444 solution and half (50 mL) of the sodium phenylglycinate solution (ca. 20 mmol/10 equiv) were combined. The resultant yellow-tan solution was vigorously stirred with dichloromethane (50 mL) for 15 min, and then transferred to a 250-mL separatory funnel. The organic layer was separated and transferred back onto the separatory funnel. The dichloromethane solution was extracted with the remaining aqueous sodium phenylglycinate (1-2 min shaking each time). The dichloromethane layer was dried over MgSO₄ for 15 min, filtered using a 20-50μ fritted funnel, and taken to dryness on a rotary evaporator. Methanol (25 mL) was added to the residual oily solid to yield a faint tan-yellow solution which was taken to dryness on the rotary evaporator to yield a yellowish solid. This material was dried in vacuo at 35° C. for 24 h. The elemental analysis is consistent with the expected GC4716 structure $C_{38}H_{53}MnN_7O_4 \cdot H_2O$. Anal Cal'd: C, 62.80%; H, 7.35%; N, 13.49%. Anal Found: C, 61.14%; H, 7.44%; N, 13.08.

6.5 g of yellowish powder was isolated giving a yield of 90% based on starting GC4444. The material was analyzed by HPLC and gave purity of 99%.

Example 16

Synthesis of Manganese(II)bis-racemic-phenylglycinato[(4aR,13aR,17aR,21aR)-1,2,3,4,4a,5,6,12,13,13a,14,15,16,17,17a,18,19,20,21,21a-Eicosahydro-11,7-nitrilo-7H-dibenzo[b,h][1,4,7,10]tetraazacycloheptadecine-κN5, κN13, κN18, κN21, κN22]-, [bis-(rac)-2-Phenylglycinato(GC4403)]. GC4717

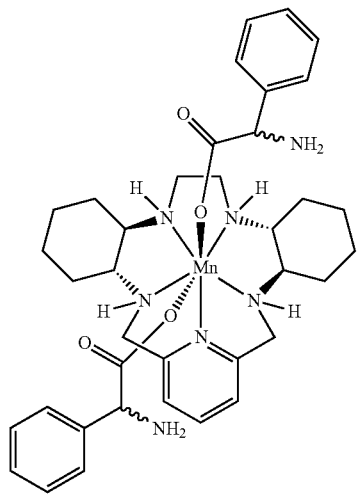

[Bis-(rac)-Phenylglycinato(GC4403)]
$C_{37}H_{51}MnN_7O_4$
MW 712.80

GC4403 (3 g, 6.2 mmol) was added to 75 mL of DI water in a 125 mL

Erlenmeyer flask and stirred vigorously for 15-20 min to yield a light orange solution. In a separate 250-mL Erlenmeyer flask, 18.76 g (124 mmol) of racemic-phenylglycine was added with vigorous stirring to 125 mL of DI water. To this solution was added solid 4.9 g of NaOH. Upon stirring vigorously for 10 min, a colorless solution resulted and the pH was measured to be 12. In a 500-mL Erlenmeyer flask the GC4403 solution and 75 mL of the sodium racemic-phenylglycinate solution were combined. The light brown solution was stirred for 5 additional min. The solution was transferred to a 250-mL separatory funnel, and extracted with dichloromethane (75 mL, about 1-2 min shaking). The organic layer was separated and back-extracted with the remaining aqueous sodium racemic-phenylglycinate. The dichloromethane layer was dried over MgSO₄ for 15 min, filtered using a 20-50μ fritted funnel, and rendered dry (i.e., gum) using a rotavap. Methanol (25 mL) was used to co-evaporate residual dichloromethane to yield a light orange solid. This material was dried in vacuo at 37° C. for 20 h. 5.42 g of yellowish solid material was isolated affording a yield of 100% based on GC4403. Analysis of this material by HPLC showed a purity of 99.5%. The elemental analysis is consistent with the expected GC4717 structure $C_{37}H_{51}MnN_7O_4 \cdot H_2O$. Anal Cal'd: C, 62.35%; H, 7.21%; N, 13.76%; and Mn, 7.71%. Anal Found: C, 60.72%; H, 7.26%; Mn, 7.44%; N, 13.34%; and chlorine (as total halogen content), 364 ppm.

Example 17

Synthesis of Manganese(II)bis-n-Butyrato[(4aS,13aS,17aS,21aS)-1,2,3,4,4a,5,6,12,13,13a,14,15,16,17,17a,18,19,20,21,21a-Eicosahydro-11,7-nitrilo-7H-dibenzo[b,h][1,4,7,10]tetraazacycloheptadecine-κN5, κN13, κN18, κN21, κN22]-, [bis-n-Butyrato (GC4419)]. GC4713

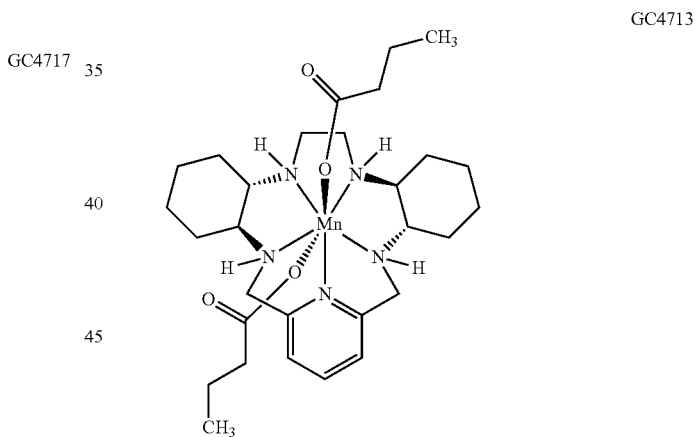

GC4419 (5.0 g, 10.34 mmol) was added to a 500-mL Erlenmeyer flask containing 100 mL of DI water. The mixture was stirred vigorously for 15-20 min, then sonicated/warmed (using heat gun) for 10 min to yield a tan, hazy solution which was then filtered to remove a trace amount of insolubles affording a clear solution. Separately, sodium butyrate (92 g, 0.835 mol) was dissolved in 200 mL of DI water in a 500 mL Erlenmeyer flask. To the flask containing GC4419 solution was added 100 mL of the sodium butyrate solution. The tan solution was stirred for 5 additional min and then transferred to a 500-mL separatory funnel and extracted with DCM (75 mL). The organic layer was transferred back into the separatory funnel and back-extracted with the remaining aqueous sodium butyrate (100 mL). The DCM layer was dried over MgSO₄ for 15 min (w/stirring), filtered using a 20-50μ fritted funnel, and rendered dry (i.e., foam) using a rotary evaporator. Methanol (50 mL) was used to dissolve the solid and then that solution taken to dryness on the rotary evaporator affording a light yellow oil. This material was further dried in vacuo at 30° C. for 48 h to afford a tan solid (4.5 g for a 76% yield based on starting GC4419). HPLC analysis showed a purity of 99.6 area %. The elemental analysis is consistent with the expected GC4713 structure $C_{29}H_{49}MnN_5O_4$. Anal Cal'd: C, 59.37%; H, 8.42%; N, 11.94%; and Mn, 9.36%. Anal Found: C, 59.32%; H, 8.55%; Mn, 8.80%; N, 11.94%; and chlorine (as total halogen content), 546 ppm.

Example 18

Synthesis of Manganese(II)bis-Benzoato[(4aS,13aS, 17aS,21aS)-1,2,3,4,4a,5,6,12,13,13a,14,15,16,17, 17a,18,19,20,21,21a-Eicosahydro-11,7-nitrilo-7H-dibenzo[b,h][1,4,7,10] tetraazacycloheptadecine-κN5, κN13, κN18, κN21, κN22]-, [bis-Benzoato (GC4419)]: GC4712

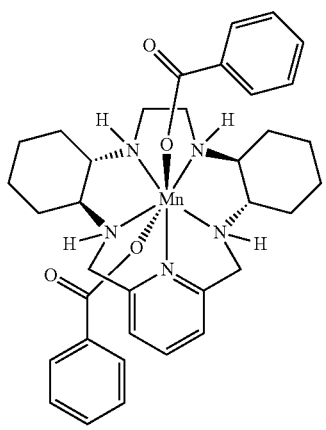

[Bis-Benzoato(GC4419)]
$C_{35}H_{45}MnN_5O_4$
MW 654.71

In a 500 mL Erlenmeyer flask containing 200 mL of DI water was added 10 g of GC4419 with vigorous stirring. The resulting clear, light tan solution was filtered to remove trace levels of insolubles and this solution was then added to 100 mL of an aqueous sodium benzoate (66 g) solution (ca. 458 mmol, 11 equiv) as a slow stream over 5 min. A gelatinous white solid separated towards the end of addition. Dichloromethane (100 mL) was added to the mixture with vigorous stirring dissolving all the solid material. The resulting two-phase mixture was then transferred to a separatory funnel. The organic layer was separated, dried over $MgSO_4$ (10 g), filtered, and rendered dry under reduced pressure on a rotary evaporator. Methanol was added to the flask containing the residual oily solid and that solution was also taken to dryness on the rotary evaporator to yield a pale yellow solid. This material was dried in vacuo at 30° C. for 40 h. and afforded 7.8 g (57% yield based on GC4419) of a light yellow-tan solid which was analyzed by HPLC and showed a purity of 99.6%. Elemental analysis was consistent with the expected GC4712 structure for $C_{35}H_{45}MnN_5O_4$.0.5 $H_2O$. Anal Calc'd: C, 63.34%; H, 6.99%; N, 10.55%; Mn, 8.28%. Anal Found: C, 63.07%; H, 7.38%; N, 10.54%; Mn, 8.16%; and trace Cl (211 ppm).

Example 19

Synthesis of Manganese(II)bis-L-Lactato[(4aS,13aS, 17aS,21aS)-1,2,3,4,4a,5,6,12,13,13a,14,15,16,17, 17a,18,19,20,21,21a-Eicosahydro-11,7-nitrilo-7H-dibenzo[b,h][1,4,7,10] tetraazacycloheptadecine-κN5, κN13, κN18, κN21, κN22]-, [bis-L-Lactato (GC4419)]: GC4714

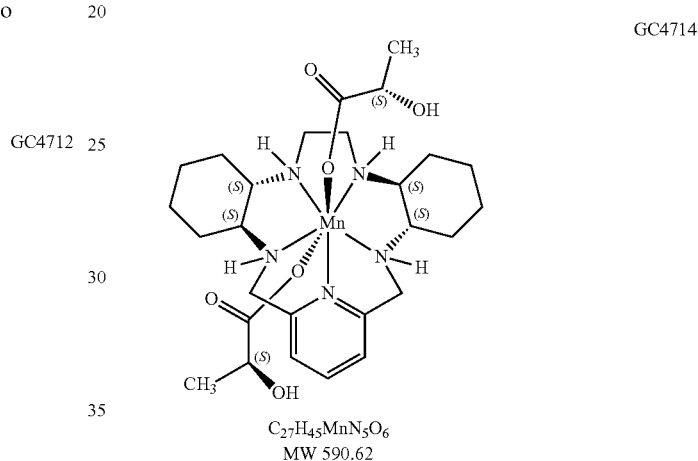

$C_{27}H_{45}MnN_5O_6$
MW 590.62

In a 500 mL Erlenmeyer flask containing 100 mL of DI water was added 5 g (10.34 mmol) of GC4419 with vigorous stirring. The resulting clear, light tan solution was filtered to remove trace levels of insolubles and to this solution was then added 125 mL of an aqueous sodium L-Lactate (23.4 g) solution as a slow stream over 5 min. The resulting tan solution was stirred for 5 additional min. and then transferred to a 500-mL separatory funnel and extracted with DCM (75 mL). The organic layer was transferred back onto the separatory funnel and back-extracted with the remaining aqueous sodium (L)-lactate (125 mL). The dichloromethane layer was dried over $MgSO_4$ for 15 min (w/stirring), filtered using a 20-50µ fritted funnel, and rendered dry (i.e., foam) using a rotavap. to remove the solvent. Methanol (50 mL) was then added to the flask and used to co-evaporate residual DCM to yield a tan syrup using the rotary evaporator. This material was further dried in vacuo at 30° C. for 48 h to yield a tan solid.

The isolated tan amorphous solid was analyzed by HPLC and showed a purity of 99.7%. Elemental analysis is consistent with the expected GC4714 structure $C_{27}H_{45}MnN_5O_6.H_2O$. Anal Calc'd: C, 53.28%; H, 7.78%; N, 11.51%; Mn, 9.03%. Anal Found: C, 53.12%; H, 7.77%; N, 11.91%; Mn, 9.06%; and Cl, (0.87%).

Example 20

Synthesis of Manganese(II)bis-rac-Mandelato[(4aS,13aS,17aS,21aS)-1,2,3,4,4a,5,6,12,13,13a,14,15,16,17,17a,18,19,20,21,21a-Eicosahydro-11,7-nitrilo-7H-dibenzo[b,h][1,4,7,10] tetraazacycloheptadecine-κN5, κN13, κN18, κN21, κN22]-, [bis-rac-Mandelato (GC4419)]: GC4706

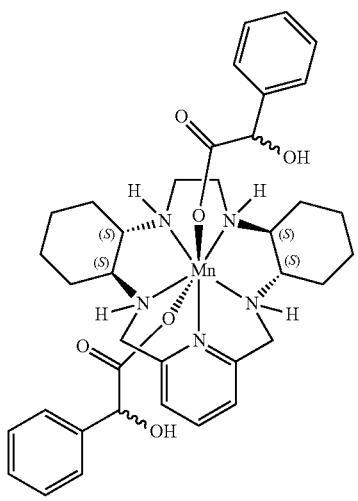

GC4706

Mol. Wt. 714.77

To a 500-mL Erlenmeyer was added 200 mL of DI water and 12.4 g of the rac-Mandelic acid. After stirring this mixture for 5 min, a clear, colorless solution resulted. It was treated with 3.2 g of NaOH as pellets and the mixture stirred vigorously. The pH was measured when all NaOH had dissolved. The pH was 3.61 and was adjusted to low alkaline using 5 wt % aqueous NaOH (resulting pH=9.67). A hazy solution of 5 g of GC4419 in 100 mL of DI water was filtered (20-50μ) and added in one portion to ½ of the pH-adjusted aqueous solution of the sodium salt. The precipitated white sticky material was stirred for an additional 5 min and placed in a refrigerator at 2-8° C. overnight. The next morning, the suspension was transferred into a 250-mL separatory funnel and 100 mL of dichloromethane was used to rinse the Erlenmeyer flask with the suspension and dichloromethane wash combined in the separatory funnel. The dichloromethane layer turned immediately light tan-yellow. The layers were separated and the dichloromethane layer extracted with the second half of aqueous sodium mandelate solution. After shaking vigorously and settling for 10 min. the dichloromethane layer was dried over MgSO$_4$ (10 g) filtered and the solvent removed. Methanol (50 mL) was added and the yellow solution evaporated to co-distill left over dichloromethane via the rotary evaporator. The resulting foam was dried in vacuo at 30° C. overnight. The isolated off-white powder (6.7 g, 91% yield) was analyzed by HPLC and showed a purity of 99.5%.

Elemental analysis is consistent with the expected GC4706 structure and showed the following results: C, 61.64%; H, 7.04%; Mn, 7.16%; N, 9.30%; and Cl, 66 ppm (0.0066%). Delta (Δ) values from a 1/3-hydrated species: C, 0.52%; H, 0.04%; Mn, 0.07%; N, 0.08%; and Cl 0%.

Example 21

Synthesis of Manganese(II)bis-L--valinato[(4aS,13aS,17aS,21aS)-1,2,3,4,4a,5,6,12,13,13a,14,15,16,17,17a,18,19,20,21,21a- Eicosahydro-11,7-nitrilo-7H-dibenzo[b,h][1,4,7,10] tetraazacyclo-heptadecine-κN5, κN13, κN18, κN21, κN22]-, .[bis-(L)-Valinato(GC4419)]: GC4746.

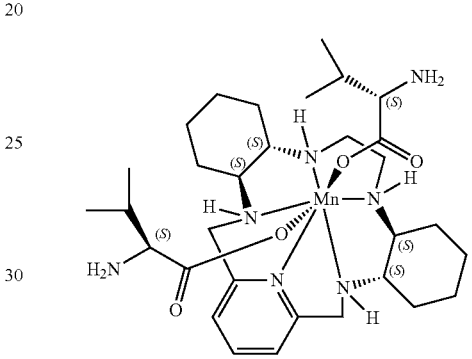

GC4746

$C_{31}H_{59}MnN_7O_4$
Mol. Wt. = 644.76

GC4419 (3.0 g, 6.2 mmol) was added to a 250-mL Erlenmeyer flask containing 100 mL of DI water. The mixture was stirred vigorously for 15-20 min to yield a light, brownish solution. In a separate flask was prepared an aqueous solution of 58.6 g L-(+)-valine (0.5 mol) and NaOH (20 g, 0.5 mol) in 200 mL of DI water. The pH of this solution was recorded as 11.7 In a 500-mL Erlenmeyer flask combined the GC4419 solution and half of the sodium valinate solution together. The resultant solution was stirred for 5 additional min and was transferred to a 0.5-L separatory funnel and extracted with 100 mL of dichloromethane. The organic layer was separated, transferred back into a separatory funnel and back-extracted with the remaining aqueous sodium valinate solution. The dichloromethane layer was separated and the solvent removed using a rotavap. Methanol (50 mL) was used to co-evaporate residual dichloromethane to yield a light brown solid. This material was dried in vacuo at 40° C. for 20 h.

There was obtained 3.4 g of the isolated light gray solid corresponding to 83% yield based on GC4419. HPLC analysis showed a purity of 99.6% and the elemental analysis showed 0.67% residual chloride expressed as total halogen content and consistent with the GC4746.0.5 H$_2$O structure. Anal Calc'd: C, 56.87%; H, 8.77%; Mn, 8.39%; and N, 14.97%. Anal Found: C, 57.22%; H, 8.70%; Mn, 7.88%; N, 14.12%; and Cl as total halogen content of 0.67%.

Example 22

Synthesis of Manganese(II)bis-propionato[6R-Methyl(4aR,13aR,17aR,21aR)-1,2,3,4,4a,5,6,12,13,13a,14,15,16,17,17a,18,19,20,21,21a-Eicosahydro-11,7-nitrilo-7H-dibenzo[b,h][1,4,7,10] tetraazacycloheptadecine-κN5, κN13, κN18, κN21, κN22]-, [bis-propionato(GC4444)]: GC4747

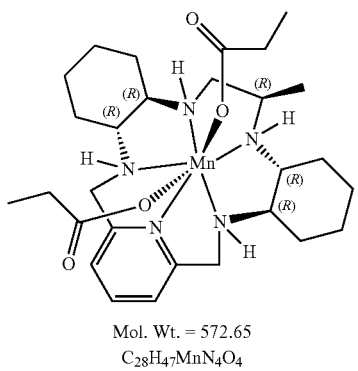

Mol. Wt. = 572.65
$C_{28}H_{47}MnN_4O_4$

GC4444 (1.6 g, 3.2 mmol) was added to a 125-mL Erlenmeyer flask containing 50 mL of DI water. The mixture was stirred vigorously for 15-20 min to yield a light yellow solution. In a separate flask was prepared an aqueous solution of 6.15 g sodium propionate in 100 mL of DI water. In a 250-mL Erlenmeyer flask combined the GC4444 and sodium propionate solutions. The resultant solution was stirred for 15 min and was transferred to a 0.25-L separatory funnel and extracted with 50 mL of dichloromethane. The organic layer was separated and the solvent removed using a rotavap. Methanol (25 mL) was used to co-evaporate residual dichloromethane to yield a light brown solid. This material was dried in vacuo at 40° C. for 24 h.

There was obtained 1.1 g of the isolated light tan solid corresponding to 60% yield based on GC4444. HPLC analysis showed a purity of 99.5% and the elemental analysis showed 1.44% residual chloride expressed as total halogen content and consistent with the GC4747.0.5 $H_2O$ structure. Anal Calc'd: C, 57.82%; H, 8.32%; Mn, 9.45%; and N, 12.04%. Anal Found: C, 58.19%; H, 8.50%; Mn, 9.39%; N, 12.36%; and Cl as total halogen content of 1.44%.

Example 23

Synthesis of Manganese(II)bis-propionato[(4aR,13aR,17aR,21aR)-1,2,3,4,4a,5,6,12,13,13a,14,15,16,17,17a,18,19,20,21,21a-Eicosahydro-11,7-nitrilo-7H-dibenzo[b,h][1,4,7,10] tetraazacycloheptadecine-κN5, κN13, κN18, κN21, κN22]-, [bis-propionato (GC4403)]: GC4748

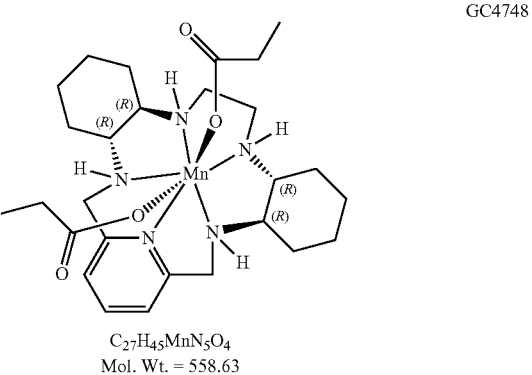

$C_{27}H_{45}MnN_5O_4$
Mol. Wt. = 558.63

GC4403 (3.0 g, 6.2 mmol) was added to a 250-mL Erlenmeyer flask containing 75 mL of DI water. The mixture was stirred vigorously for 15-20 min to yield a light, brownish solution. In a separate flask was prepared an aqueous solution of 23.8 g sodium propionate in 75 mL of DI water. In a 500-mL Erlenmeyer flask combined the GC4403 solution and 40 mL of the sodium propionate solution together. The resultant solution was stirred for 5 additional min and was transferred to a 0.5-L separatory funnel and extracted with 50 mL of dichloromethane. The organic layer was separated, transferred back into a separatory funnel and back-extracted with remaining aqueous sodium propionate (35 mL). The dichloromethane layer was separated and the solvent removed using a rotavap. Methanol (25 mL) was used to co-evaporate residual dichloromethane to yield a light brown solid. This material was dried in vacuo at 40° C. over the weekend.

There was obtained 2.7 g of the isolated light brown solid corresponding to 78% yield based on GC4403. HPLC analysis showed a purity of 97.3% (1.2% monoamine GC4520) and the elemental analysis showed 0.356% residual chloride expressed as total halogen content and consistent with the GC4748 structure. Anal Calc'd: C, 58.05%; H, 8.12%; Mn, 9.83%; and N, 12.54%. Anal Found: C, 58.00%; H, 8.45%; Mn, 9.57%; N, 12.53%; and Cl as total halogen content of 0.356%.

Example 24

Synthesis of Manganese(II)bis-pyruvato[(4aS,13aS,21aS)-1,2,3,4,4a,5,6,12,13,13a,14,15,16,17,17a,18,19,20,21,21a-Eicosahydro-11,7-nitrilo-7H-dbenzo[b,h][1,4,7,10] tetraazacycloheptadecine-κN5, κN13, κN18, κN21, κN22]-, [bis-pyruvato(GC4419)]: GC4749

Using a 500-mL Erlenmeyer, 150 mL of DI water was added to GC4419 (FW 483.38, 5 g, 10.34 mmol) and stirred vigorously for 15-20 min to dissolve. In a second Erlenmeyer, pyruvic acid (72.83 g, 0.827 mol) was added to 400 mL DI water. While stirring the suspension, NaOH was added (0.83 mol, 33.2 g) and stirring continued until a clear, colorless solution resulted. The pH of this solution was ca. 12. In a 500-mL Erlenmeyer flask, the GC4419 solution and half of the sodium pyruvate solution were combined. No solid separated and the tan mixture was stirred for 5 additional min. The light tan-yellow solution was transferred to a 1-L separatory funnel and extracted with DCM (100 mL, about 1-2 min shaking each time). The aqueous solution was colored light pink-purple. The DCM layer was back-extracted with the remaining aqueous sodium pyruvate. The DCM layer was dried over $MgSO_4$ for 15 min (w/stirring), filtered using a 20-50μ fritted funnel, and may then be rendered dry using a rotavap. MeOH (50 mL) may then be used to co-evaporate residual DCM to yield a solid. This material may be dried in vacuo at 30° C. for at least 20 h. The solid may be characterized by elemental analysis, MS and HPLC.

Example 25

Synthesis of Manganese(II)bis-L-alaninato[(4aS,13aS,17aS,21aS)-1,2,3,4,4a,5,6,12,13,13a,14,15,16,17,17a,18,19,20,21,21a-Eicosahydro-11,7-nitrilo-7H-dibenzo[b,h][1,4,7,10] tetraazacycloheptadecine-κN5, κN13, κN18, κN21, κN22]-, [bis-L-alaninato (GC4419)]: GC4750

Using a 500-mL Erlenmeyer, 150 mL of DI water was added to GC4419 (FW 483.38, 5 g, 10.34 mmol) and stirred vigorously for 15-20 min to dissolve. In a second Erlenmeyer, L-(+)-alanine (73.7 g, 0.827 mol) was added to 400 mL DI water. While stirring the suspension, NaOH (0.83 mol, 33.2 g) was added and stirring continued until a clear, colorless solution resulted. The pH of this solution was 12.1. In a 500-mL Erlenmeyer flask, the GC4419 solution and half of the sodium alaninate solution were combined. No solid separated and the tan mixture was stirred for 5 additional min. The light tan-yellow solution was transferred to a 1-L separatory funnel and extracted with DCM (100 mL, about 1-2 min shaking each time). The aqueous solution was colored light pink-purple. The DCM layer was back-extracted with the remaining aqueous sodium alaninate. The DCM layer was dried over $MgSO_4$ for 15 min (w/stirring), filtered using a 20-50μ fritted funnel, and may then be rendered dry using a rotavap. MeOH (50 mL) may be used to co-evaporate residual DCM to yield a solid. This material may be dried in vacuo at 30° C. for at least 20 h. The solid may be characterized by elemental analysis, MS and HPLC.

Results

In the Table I below are summarized bioavailability data from id dosing of minipigs of various pure single base oil formulations with various axial ligand derivatives of various Mn(II) pentaaza macrocyclic ring complexes. In each example, the concentration of test article drug compound was ten percent by weight of the total formulation.

TABLE I

| Compound Utilized (axial ligand) | Base Oil | Mini-Pig BioA |
| --- | --- | --- |
| GC4419 (Chloro) | Capmul MCM | 9% |
| GC4701 (Acetato of GC4419) | Capmul MCM | 15% |
| GC4702 (L-Phenylglycinato of GC4419) | Capmul MCM | 43% |
| GC4720 (rac-Phenylglycinato of GC4419) | Capmul MCM | 33% |
| GC4718 (Phenylacetato of GC4419) | Capmul MCM | 32% |
| GC4719 (Phenylglyoxylato of GC4419) | Capmul MCM | 25% |
| GC4704 (L-Phenylalaninato of GC4419) | Capmul MCM | 10% |
| GC4746 (L-Valinato of GC4419) | Capmul MCM | 13% |
| GC4705 (rac-2-Phenylpropionato of GC4419) | Capmul MCM | 23% |
| GC4706 (rac-Mandelato of GC4419) | Capmul MCM | 28% |
| GC4707 (Cyclohexanebutyrato of GC4419) | Capmul MCM | 9% |
| GC4711 (Propionato of GC4419) | Capmul MCM | 27% |
| GC4708 (Dodecanoato of GC4419) | Capmul MCM | 12% |
| GC4709 (Pivaloato of GC4419) | Capmul MCM | 17% |
| GC4710 (Octanoato of GC4419) | Capmul MCM | 13% |
| GC4712 (Benzoato of GC4419) | Capmul MCM | 24% |
| GC4714 (L-Lactato of GC4419) | Capmul MCM | 36% |
| GC4401 (Chloro) | Capmul MCM | 15% |
| GC4715 (rac-Phenylglycinato of GC4401) | Capmul MCM | 36% |
| GC4403 (Chloro) | Capmul MCM | 9% |
| GC4717 (rac-Phenylglycinato of GC4403) | Capmul MCM | 26% |
| GC4748 (Propionato of GC4403) | Labrafil M2125 CS | 22% |
| GC4444 (Chloro) | Capmul MCM | 14% |
| GC4716 (rac-Phenylglycinato of GC4444) | Capmul MCM | 34% |
| GC4747 (Propionato of GC4444) | Labrafil M2125 CS | 20% |
| GC4419 (Chloro) | Peceol | 9% |
| GC4701 (Acetato of GC4419) | Peceol | 11% |
| GC4702 (L-Phenylglycinato of GC4419) | Peceol | 29% |
| GC4705 (rac-2-phenylpropionato of GC4419) | Peceol | 24% |
| GC4719 (Phenylglyoxylato of GC4419) | Peceol | 28% |
| GC4711 (Propionato of GC4419) | Peceol | 29% |
| GC4712 (Benzoato of GC4419) | Peceol | 29% |
| GC4713 (Butyrato of GC4419) | Peceol | 18% |
| GC4419 (Chloro) | Miglyol 812N | 8% |
| GC4702 (L-Phenylglycinato of GC4419) | Miglyol 812N | 42% |
| GC4720 (rac-Phenylglycinato of GC4419) | Miglyol 812N | 32% |
| GC4419 (Chloro) | Maisine 35-1 | 8% |
| GC4701 (Acetato of GC4419) | Maisine 35-1 | 8% |
| GC4711 (Propionato of GC4419) | Maisine 35-1 | 29% |
| GC4718 (Phenylacetato of GC4419) | Maisine 35-1 | 28% |
| GC4719 (Phenylglyoxylato of GC4419) | Maisine 35-1 | 31% |

TABLE I-continued

| Compound Utilized (axial ligand) | Base Oil | Mini-Pig BioA |
|---|---|---|
| GC4710 (Octanoato of GC4419) | Maisine 35-1 | 8% |
| GC4712 (Benzoato of GC4419) | Maisine 35-1 | 18% |
| GC4419 (Chloro) | Labrafil M2125 CS | 7% |
| GC4701 (Acetato of GC4419) | Labrafil M2125 CS | 16% |
| GC4711 (Propionato of GC4419) | Labrafil M2125 CS | 44% |
| GC4710 (Octanoato of GC4419) | Labrafil M2125 CS | 21% |
| GC4713 (Butyrato of GC4419) | Labrafil M2125 CS | 21% |
| GC4709 (Pivaloato of GC4419) | Labrafil M2125 CS | 22% |
| GC4702 (L-Phenylglycinato of GC4419) | Labrafil M2125 CS | 25% |
| GC4711 (Propionato of GC4419) | Labrafil M1944 CS | 23% |

In the following examples are shown plots of the plasma concentrations of the parent Mn(II) pentaaza macrocyclic ring complex following either intraduodenal (id) or iv dosing of various test article derivatives versus time after dosing the test articles. These examples are selected from the examples listed in the Table I (above). In all examples the % BioAvailability is based on a comparison of the plasma levels of test article drug obtained from comparison of the concentration values obtained from id dosing using the same pigs as utilized for the iv dosing used to calculate a 100% bioavailability AUC value.

In FIG. 1 are shown the profile plots of the plasma concentrations of the parent manganese pentaaza macrocyclic ring complex of GC4419 (independent of the composition of the axial ligands) in the plasma of the minipigs from blood samples at time points up to 24 hrs following administration with test article drugs administered by either iv or id delivery. The blood level of GC4419 following iv administration as a 1 mg/kg body weight (mpk) dose is considered to be 100% bioavailable and the plasma concentration following iv administration of an aqueous formulation of GC4419 is also shown. In this example, the intraduodenal administration of a 10 mg/kg dose of 10% by weight formulations of 1) the bis-L-phenylglycine derivative of GC4419 (GC4702), 2) the bis-L-phenylalanine derivative of GC4419 (GC4704), and 3) the bis-racemic-phenylglycine derivative of GC4419 (GC4720) as their Capmul MCM formulations are compared to iv administration of a 1 mg/kg dose of GC4419 itself.

Figure 2:
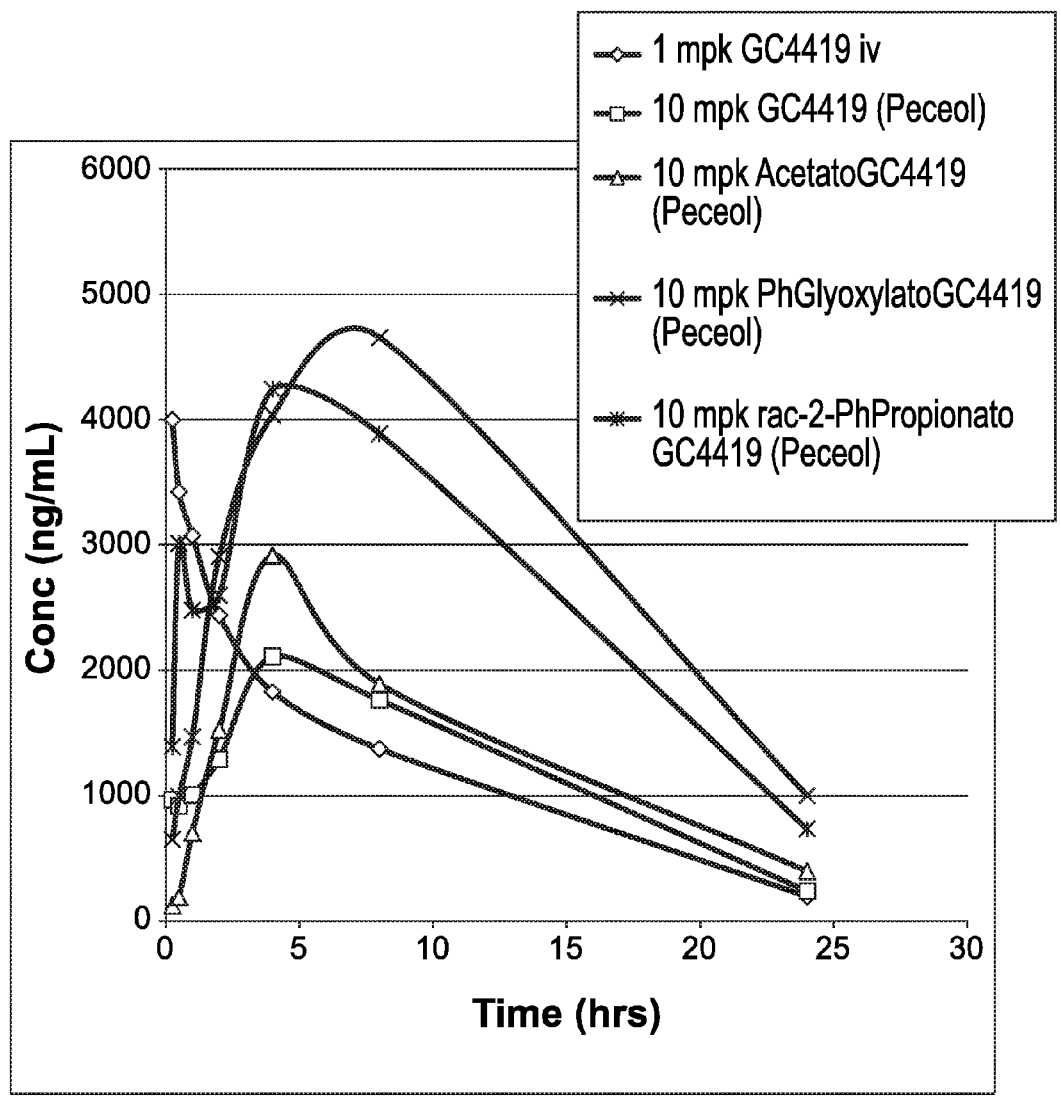
FIG. 2 is a series of profile plots of the plasma concentrations of the parent manganese pentaaza macrocyclic ring complex of GC4419 (independent of the composition of the axial ligands) in the plasma of the minipigs from blood samples at time points up to 24 hrs following administration of test article drugs (where all compounds displayed are derivatives of GC4419) by either iv or id delivery, with id test articles formulated in Peceol, as described in the Examples.

In FIG. 2 are shown the profile plots of the plasma concentrations of the parent manganese pentaaza macrocyclic ring complex of GC4419 (independent of the composition of the axial ligands) in the plasma of the minipigs from blood samples at time points up to 24 hrs following administration of test article drugs formulated in Peceol for id delivery. The blood level of parent drug (in this case GC4419) following iv administration as a 1 mg/kg body weight (mpk) dose is considered to be 100% bioavailable and the plasma concentration following iv administration of an aqueous formulation of GC4419 is also shown. In this example, the intraduodenal administration of a 10 mg/kg dose of 10% by weight formulations of 1) GC4419, 2) the bis-acetato derivative of GC4419 (GC4701), 3) the bis-phenylglyoxylato derivative of GC4419 (GC4719) and 4) the bis-racemic-2-phenylpropionato derivative of GC4419 (GC4705) as their Peceol formulations are compared to iv administration of GC4419 itself.

Figure 3:
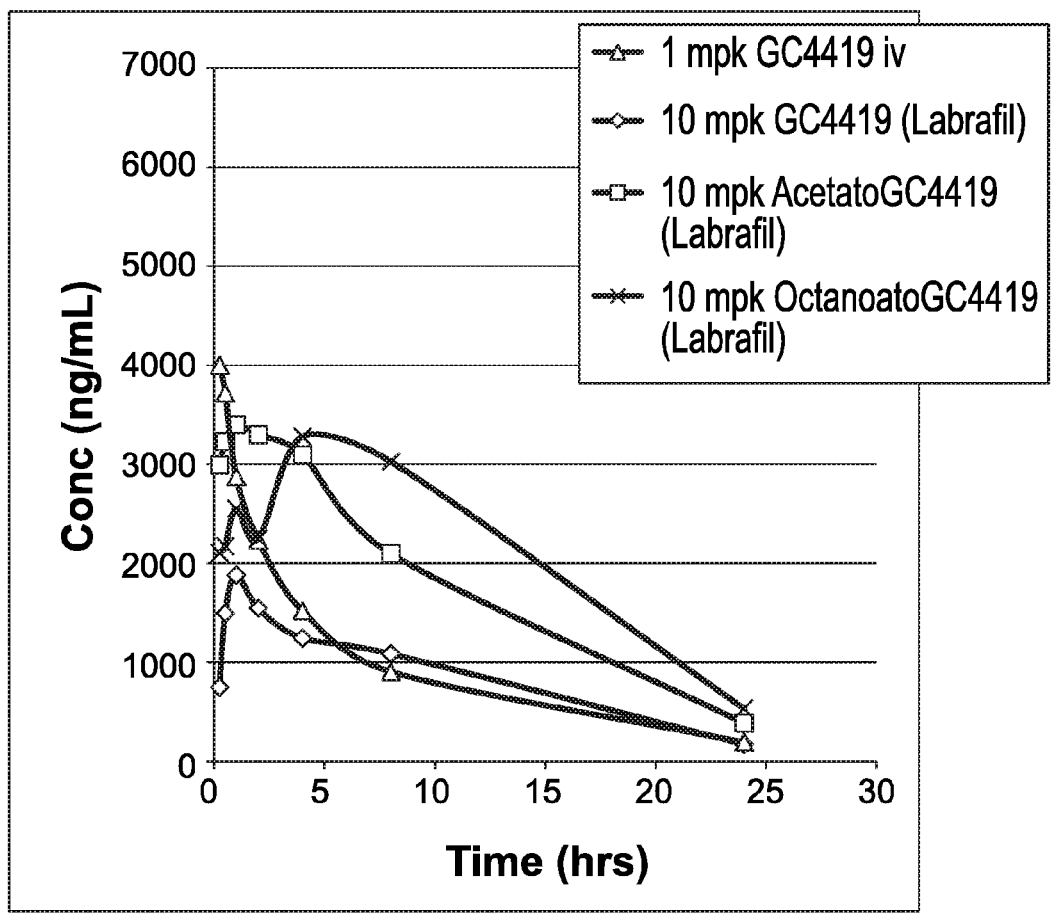
FIG. 3 is a series of profile plots of the plasma concentrations of the parent manganese pentaaza macrocyclic ring complex of GC4419 (independent of the composition of the axial ligands) in the plasma of the minipigs from blood samples at time points up to 24 hrs following administration of test article drugs (where all compounds displayed are derivatives of GC4419) by either iv or id delivery, with id test articles formulated in Labrafil M2125 CS, as described in the Examples.

In FIG. 3 are shown the profile plots of the plasma concentrations of the parent manganese pentaaza macrocyclic ring complex of GC4419 (independent of the composition of the axial ligands) in the plasma of the minipigs from blood samples at time points up to 24 hrs following administration of test article drugs formulated in Labrafil M2125 CS for id delivery. The blood level of parent drug (in this case GC4419) following iv administration as a 1 mg/kg body weight (mpk) dose is considered to be 100% bioavailable and the plasma concentration following iv administration of an aqueous formulation of GC4419 is also shown. In this figure, the intraduodenal administration of a 10 mg/kg dose of 10% by weight formulations of 1) GC4419, 2) the bis-acetato derivative of GC4419 (GC4701), and 3) the bis-octanoato derivative of GC4419 (GC4710) as their Labrafil M2125 CS formulations are compared to iv dosing of GC4419 itself in the same set of pigs.

Figure 4:
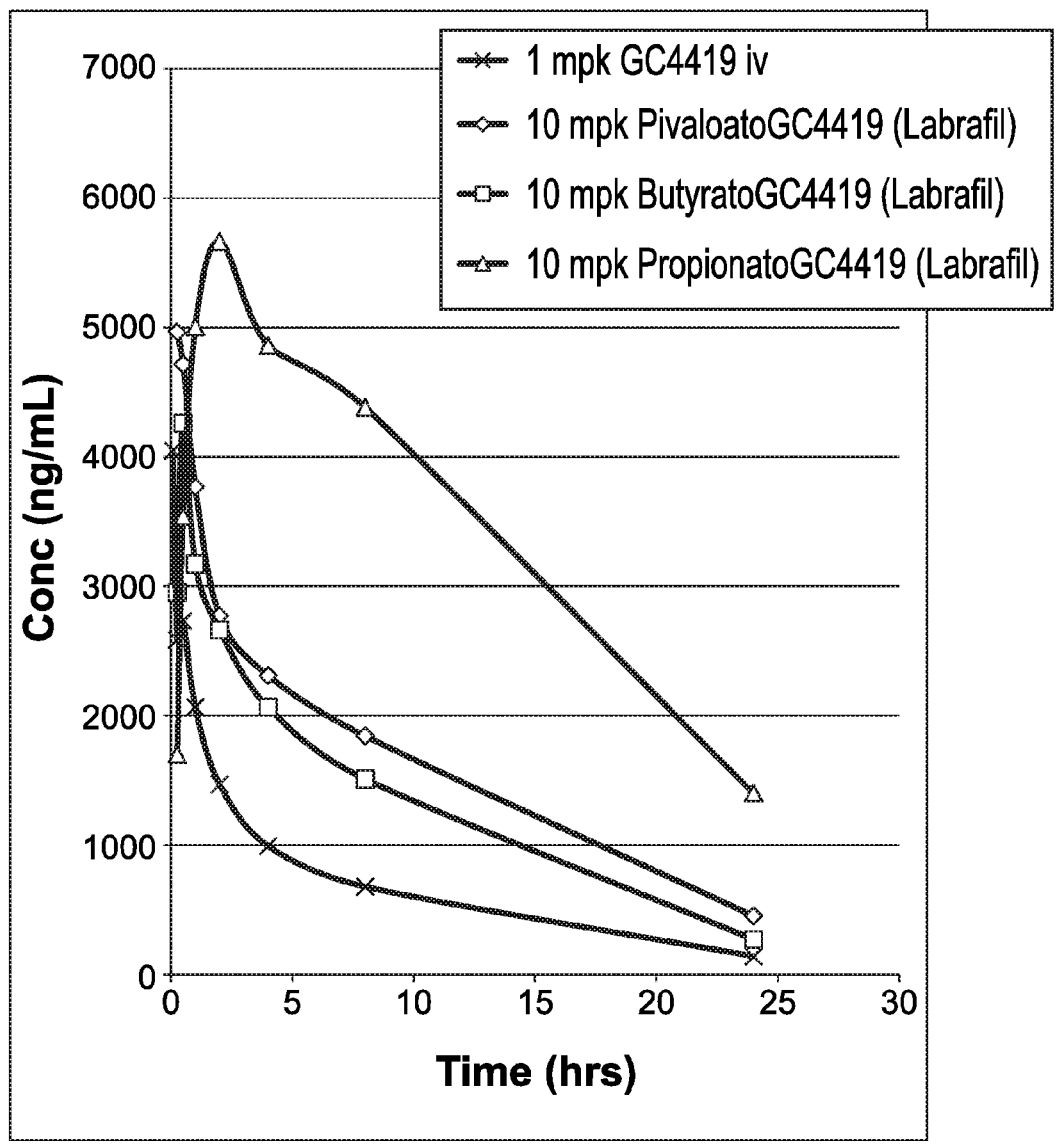
FIG. 4 is a series of profile plots of the plasma concentrations of the parent manganese pentaaza macrocyclic ring complex of GC4419 (independent of the composition of the axial ligands) in the plasma of the minipigs from blood samples at time points up to 24 hrs following administration of test article drugs (where all compounds displayed are derivatives of GC4419) by either iv or id delivery, with id test article formulated in Labrafil M2125 CS, as described in the Examples.

In FIG. 4 are shown the profile plots of the plasma concentrations of the parent manganese pentaaza macrocyclic ring complex of GC4419 (independent of the composition of the axial ligands) in the plasma of the minipigs from blood samples at time points up to 24 hrs following administration of test article drugs formulated in Labrafil M2125 CS for id delivery. The blood level of parent drug (in this case GC4419) following iv administration as a 1 mg/kg body weight (mpk) dose is considered to be 100% bioavailable and the plasma concentration following iv administration of an aqueous formulation of GC4419 is also shown. In this example, the intraduodenal administration of a 10 mg/kg dose of 10% by weight formulations of 1) the bis-pivaloato derivative of GC4419 (GC4709), 2) the bis-propionato derivative of GC4419 (GC4711), and 3) the bis-butyrato derivative of GC4419 (GC4713) as their Labrafil M2125 CS formulations are compared to iv administration of GC4419 itself in the same set of pigs.

Figure 5:
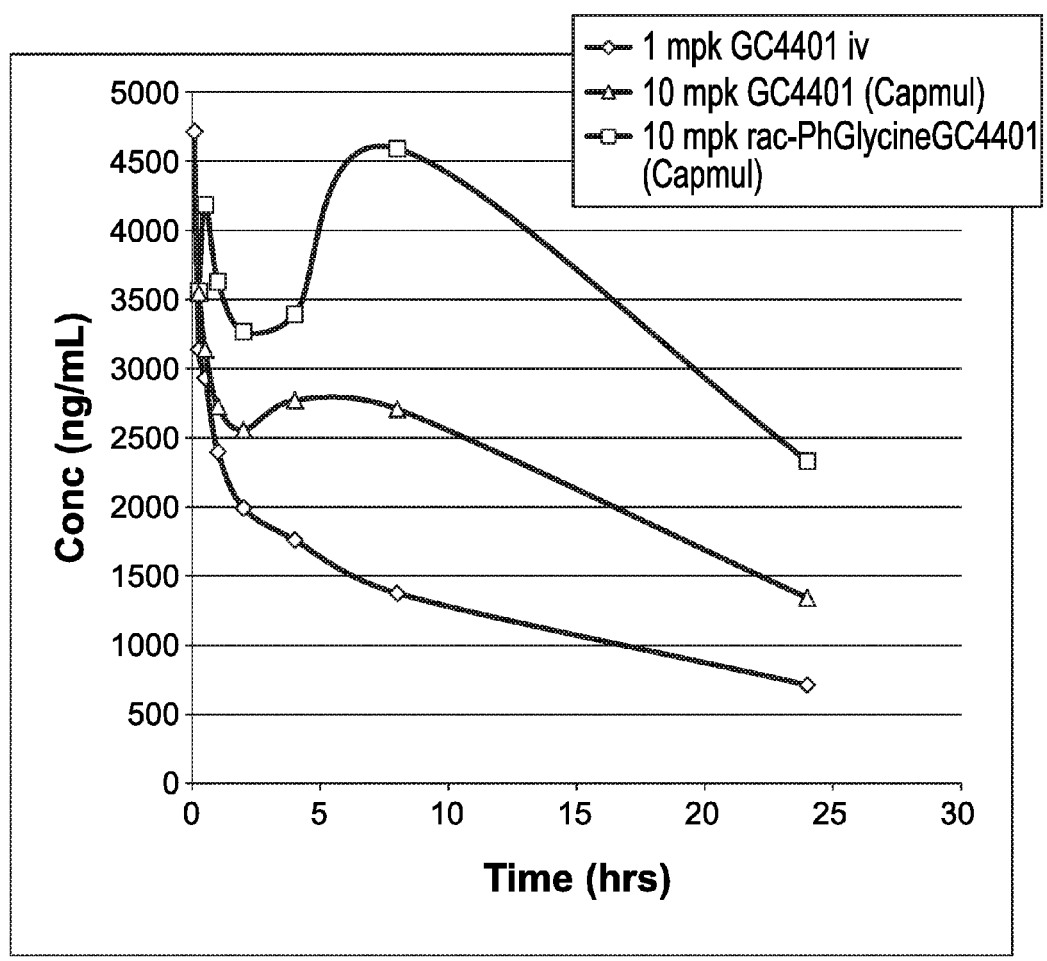
FIG. 5 is a series of profile plots of the plasma concentrations of the parent manganese pentaaza macrocyclic ring complex of GC4401 (independent of the composition of the axial ligands) in the plasma of the minipigs from blood samples at time points up to 24 hrs following administration of test article drugs (where all compounds displayed are derivatives of GC4401) by either iv or id delivery, with id test articles formulated in Capmul MCM, as described in the Examples.

In FIG. 5 are shown the profile plots of the plasma concentrations of the parent manganese pentaaza macrocyclic ring complex of GC4401 (independent of the composition of the axial ligands) in the plasma of the minipigs from blood samples at time points up to 24 hrs following administration of test article drugs formulated in Capmul MCM for id delivery. The blood level of parent drug (in this case GC4401) following iv administration as a 1 mg/kg body weight (mpk) dose is considered to be 100% bioavailable and the plasma concentration following iv administration of an aqueous formulation of GC4401 is also shown. In this example, the intraduodenal administration of a 10 mg/kg dose of 10% by weight formulations of 1) GC4401 and 2) the bis-racemic-phenylglycine derivative of GC4401 (GC4715) as their Capmul MCM formulations are compared to iv administration of GC4401 itself in the same set of pigs.

Figure 6:
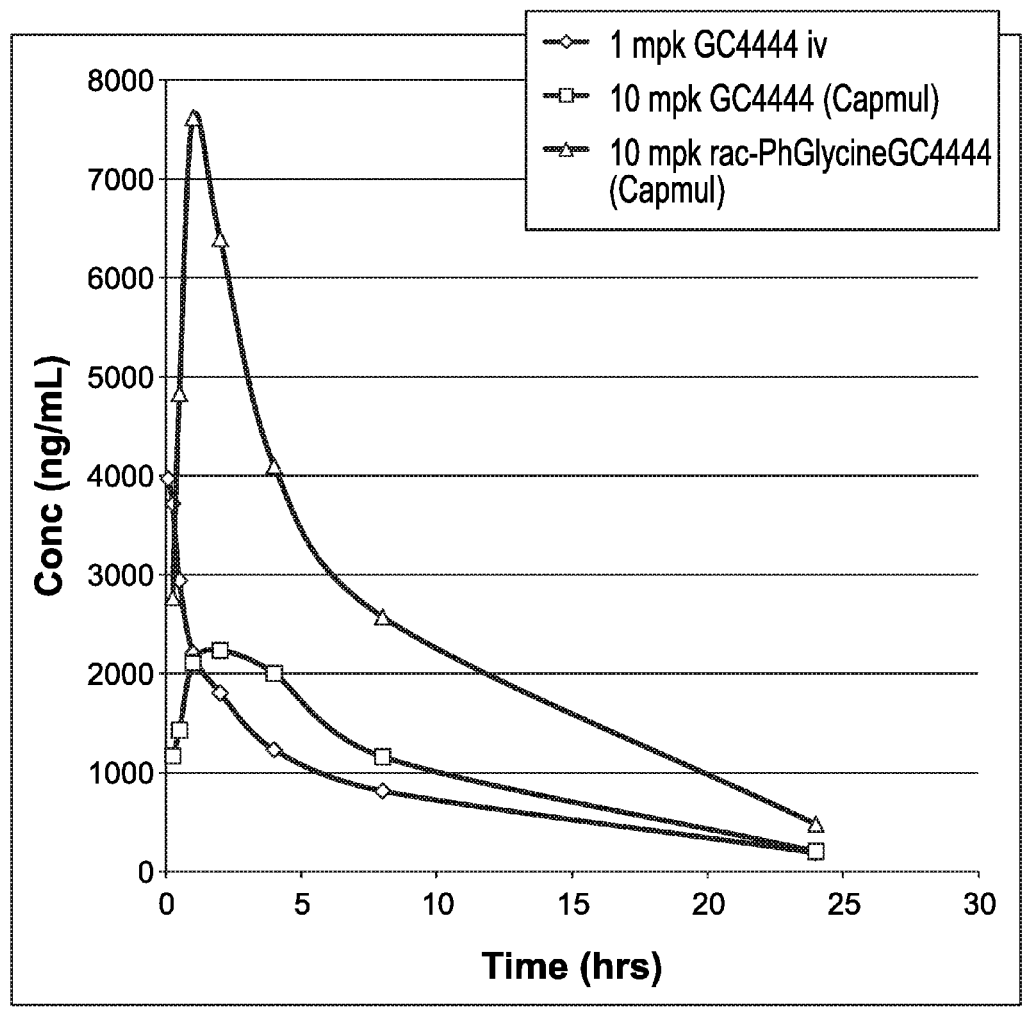
FIG. 6 is a series of profile plots of the plasma concentrations of the parent manganese pentaaza macrocyclic ring complex of GC4444 (independent of the composition of the axial ligands) in the plasma of the minipigs from blood samples at time points up to 24 hrs following administration of test article drugs (where are compounds displayed are derivatives of GC4444) by either iv or id delivery, with id test articles formulated in Capmul MCM, as described in the Examples.

In FIG. 6 are shown the profile plots of the plasma concentrations of the parent manganese pentaaza macrocyclic ring complex of GC4444 (independent of the composition of the axial ligands) in the plasma of the minipigs from blood samples at time points up to 24 hrs following administration of test article drugs formulated in Capmul MCM for id delivery. The blood level of parent drug (in this case GC4444) following iv administration as a 1 mg/kg body weight (mpk) dose is considered to be 100% bioavailable and the plasma concentration following iv administration of an aqueous formulation of GC4444 is also shown. In this example, the intraduodenal administration of a 10 mg/kg dose of 10% by weight formulations of 1) GC4444 and 2) the bis-racemic-phenylglycine derivative of GC4444 (GC4716) as their Capmul MCM formulations are compared to iv administration of GC4444 itself in the same set of pigs.

Figure 7:
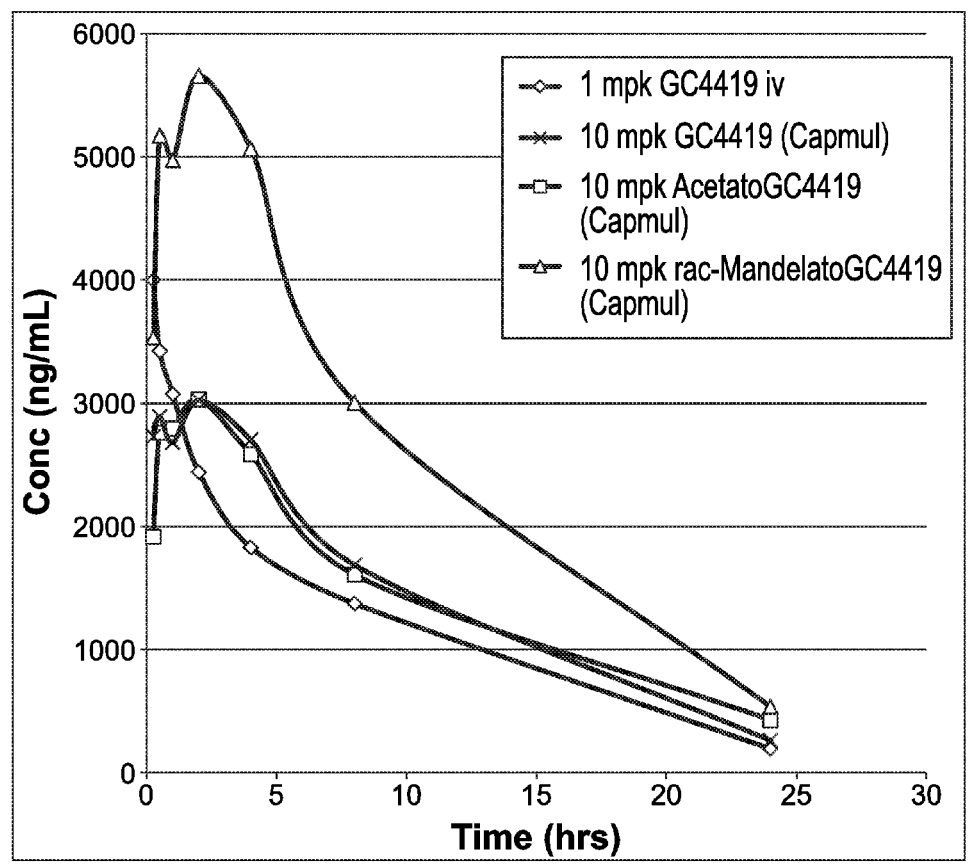
FIG. 7 is a series of profile plots of the plasma concentrations of the parent manganese pentaaza macrocyclic ring complex of GC4419 (independent of the composition of the axial ligands) in the plasma of the minipigs from blood samples at time points up to 24 hrs following administration of test article drugs (where all compounds displayed are derivatives of GC4419) by either iv or id delivery, with id test articles formulated in Capmul MCM, as described in the Examples.

In FIG. 7 are shown the profile plots of the plasma concentrations of the parent manganese pentaaza macrocyclic ring complex of GC4419 (independent of the composition of the axial ligands) in the plasma of the minipigs from blood samples at time points up to 24 hrs following administration of test article drugs formulated in Capmul MCM for id delivery. The blood level of parent drug (in this case GC4419) following iv administration as a 1 mg/kg body weight (mpk) dose is considered to be 100% bioavailable and the plasma concentration following iv administration of an aqueous formulation of GC4419 is also shown. In this example, the intraduodenal administration of a 10 mg/kg dose of 10% by weight formulations of 1) GC4419, 2) the bis-acetato derivative of GC4419 (GC4701), and 3) the bis-racemic-mandelato derivative of GC4419 (GC4706) as their Capmul MCM formulations are compared to iv administration of GC4419 itself in the same set of pigs.

Figure 8:
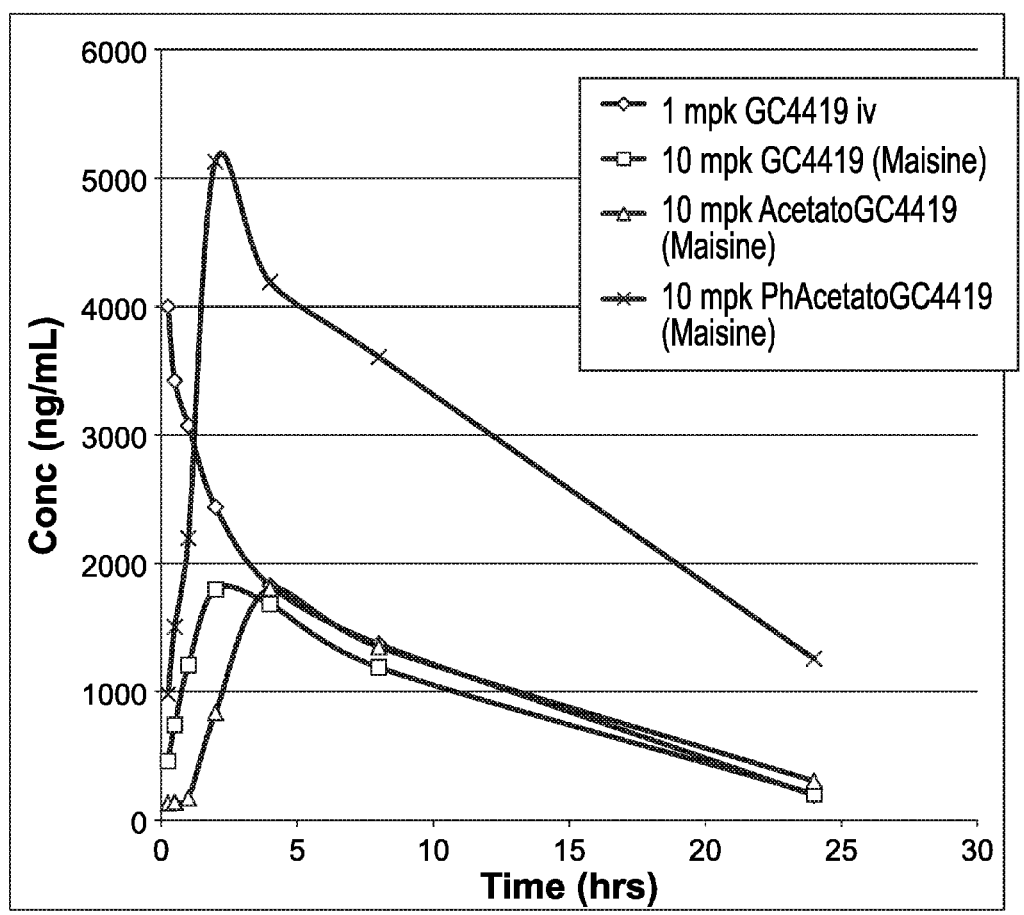
FIG. 8 is a series of profile plots of the plasma concentrations of the parent manganese pentaaza macrocyclic ring complex of GC4419 (independent of the composition of the axial ligands) in the plasma of the minipigs from blood samples at time points up to 24 hrs following administration of test article drugs (where all compounds displayed are derivatives of GC4419) by either iv or id delivery, with id test articles formulated in Maisine 35-1, as described in the Examples.

In FIG. 8 are shown the profile plots of the plasma concentrations of the parent manganese pentaza macrocyclic ring complex of GC4419 (independent of the composition of the axial ligands) in the plasma of the minipigs from blood samples at time points up to 24 hrs following administration of test article drugs formulated in Maisine 35-1 for id delivery. The blood level of parent drug (in this case GC4419) following iv administration as a 1 mg/kg body weight (mpk) dose is considered to be 100% bioavailable and the plasma concentration following iv administration of an aqueous formulation of GC4419 is also shown. In this example, the intraduodenal administration of a 10 mg/kg dose of 10% by weight formulations of 1) GC4419, 2) the bis-phenylacetato derivative of GC4419 (GC4718), and 3) the bis-acetato derivative of GC4419 (GC4701) as their Maisine 35-1 formulations are compared to iv administration of GC4419 itself in the same set of pigs.

Figure 9:
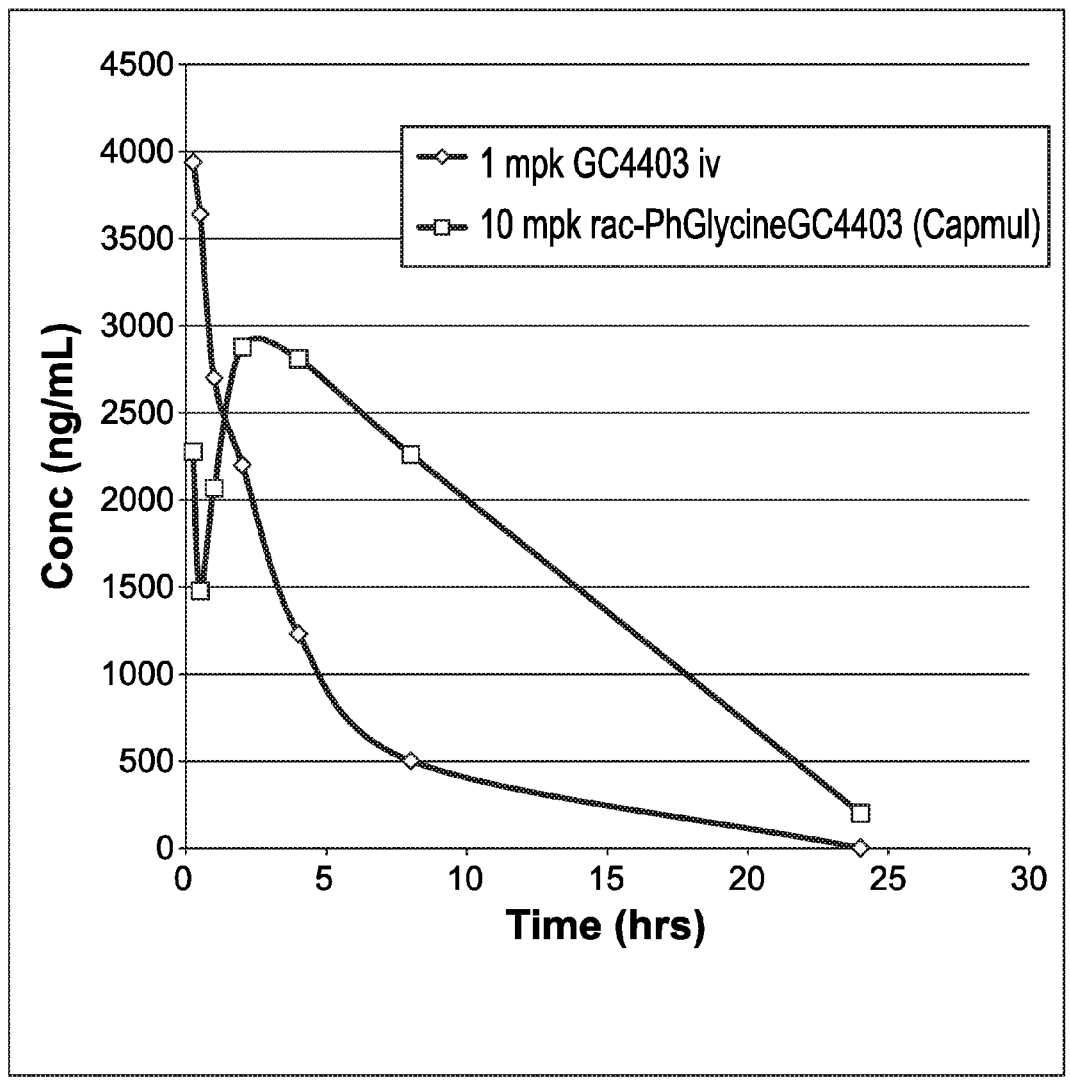
FIG. 9 is a series of profile plots of the plasma concentrations of the parent manganese pentaaza macrocyclic ring complex of GC4403 (independent of the composition of the axial ligands) in the plasma of the minipigs from blood samples at time points up to 24 hrs following administration of test article drugs (where all compounds displayed are derivatives of GC4403) by either iv or id delivery, with the id test article formulated in Capmul MCM, as described in the Examples.

In FIG. 9 are shown the profile plot of the plasma concentrations of the parent manganese pentaza macrocyclic ring complex of GC4403 (independent of the composition of the axial ligands) in the plasma of the minipigs from blood samples at time points up to 24 hrs following administration of the bis-racemic-phenylglycinato-GC4403 for id delivery. The blood level of parent drug (in this case GC4403) following iv administration as a 1 mg/kg body weight (mpk) dose is considered to be 100% bioavailable and the plasma concentration following iv administration of an aqueous formulation of GC4403 is also shown. In this example, the intraduodenal administration of a 10 mg/kg dose of 10% by weight formulation of the bis-racemic-phenylglycine derivative of GC4403 (GC4717) as its 10% by weight slurry in Capmul MCM is compared to iv administration of GC4403 itself in the same set of pigs.

The Examples cited above show that the axial ligands bonded to the Mn(II) ion can exert a very profound and previously unpredicted effect on the ability of these complexes to penetrate the GI tract and become orally bioavailable. We have found that there exists a fairly narrow structural subset of ligands that can give greatly enhanced gastrointestinal (GI) uptake and consequently greatly enhanced oral bioavailability. This subset of axial ligand structures providing enhanced oral bioavailability includes those shown in FIG. 10.

Figure 10:
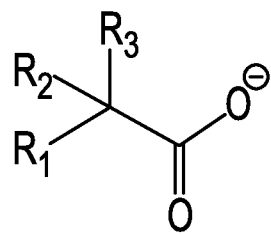
FIG. 10 is an illustration of a subset of axial ligand structures providing enhanced oral bioavailability.
Figure 10:
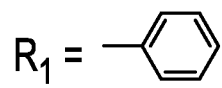
Figure 10:
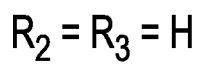
Figure 10:
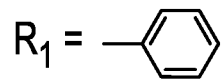
Figure 10:
Figure 10:
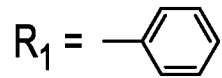
Figure 10:
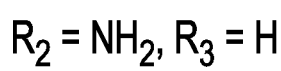
Figure 10:
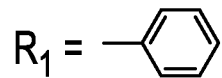
Figure 10:
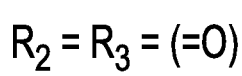
Figure 10:
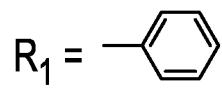
Figure 10:
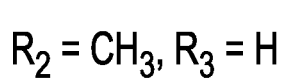
Figure 11:
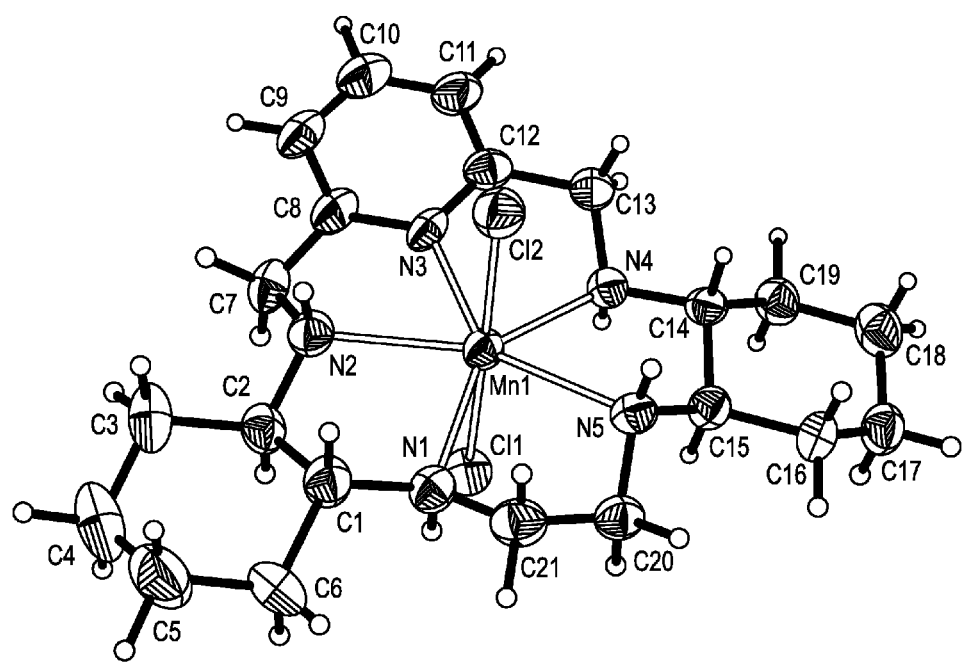
FIG. 11 is an X-ray crystal structure of GC4403 (as reported in Riley et al., *Advances in Inorganic Chemistry*, Vol. 59, pp. 233-263 (2007)).
Figure 12:
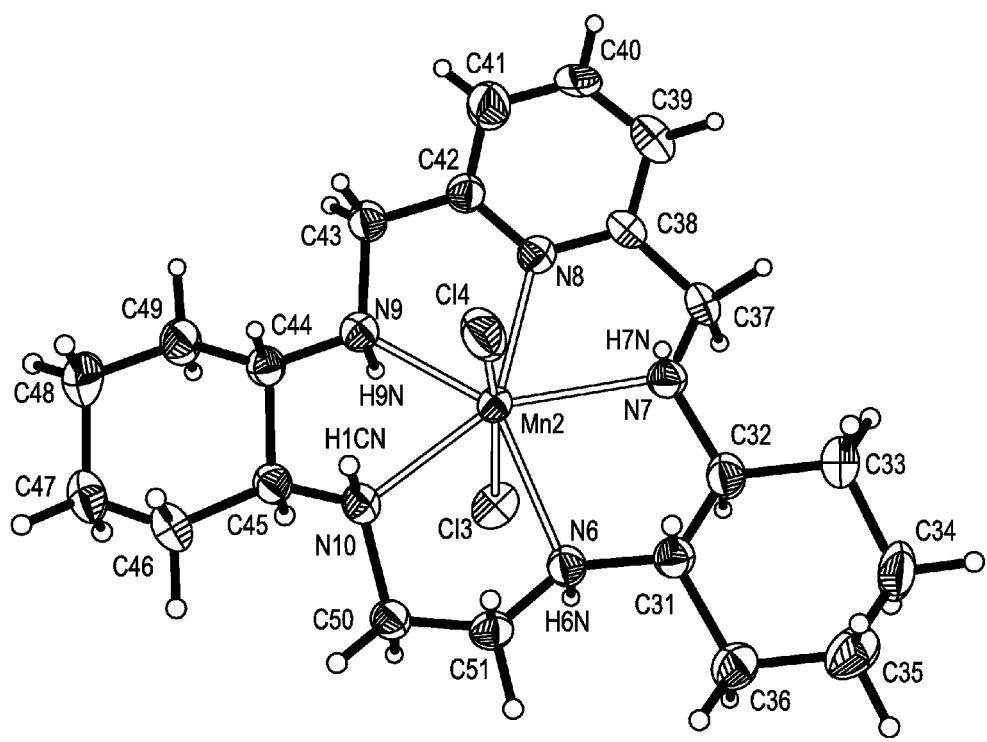
FIG. 12 is an X-ray crystal structure of GC4419 obtained by the methodology reported in Riley et al., *Advances in Inorganic Chemistry*, Vol. 59, pp. 233-263 (2007).

There are some notable structural features affecting bioavailability. First, a wide structural range of alkyl carboxylic acids were screened for oral bioavailability in various oils and it was observed that they are not equally effective at affording high oral bioavailability. In fact, the propionato ligand (and related lactato ligand—a propionato ligand with OH substituted for H, and likely other ligands based on the propionato ligand) affords much better bioavailability than any of the other carboxylato ligands; such as the one carbon atom shorter chain, acetato, or the longer chain carboxylato ligands such as butyrato or octanoato. Second, there is a unique class of axial ligands which are derived from the Phenylacetic acid; i.e., the phenylacetato ligand. These derivatives are shown in FIG. 10. All of the complexes derived from this phenylacetato class of ligands have greatly enhanced bioavailability compared to the parent dichloro complex or to other alkyl carboxylato complexes, including the acetato or other higher molecular weight carboxylato ligand derived complexes. Third, one of these derivatives is based on the amino acid, Phenylglycine. The racemic-phenylglycinato ligand enhances the bioavailability with all of the various pentaazamacrocyclic ligands tested showing that this is not just an isolated effect with the parent manganese pentaaza macrocyclic ring complex of GC4419, but is generic to this family of Mn(II) complexes. Additionally, the L-Phenylglycinato derivative of GC4419, GC4702, is actually much better absorbed than other amino acid ligands such as L-phenylalaninato or the L-valininato complexes, or the rac-phenylglycinato complex, GC4720. Further, this bioavailability enhancing property may be restricted to the phenylglycinato ligand derivatives (again a derivative of phenylacetic acid) as exemplified by the very poor bioavailability of the complexes derived from the L-Phenylalanine congener or the L-valine congener, although it is possible that other amino acid ligands, in particular the L-alanine congener that falls within the class of propionato-based ligands described above, may also provide good bioavailability.

REFERENCES

1. Suenderhauf, C., Parrott, N.; "A Physiologically Based Pharmacokinetic Model of the Minipig: Data Compilation and Model Implementation", Pharm. Res., 30(1), 1-15 (2013).
2. Salvemini, D., Wang, Z-Q., Zweier, J. L., Samouilov, A., Macarthur, H., Misko, T. P., Currue, M. G., Cuzzocrea, S., Sikorski, J. A., Riley, D. P., "*A Nonpeptidyl Mimic of Superoxide Dismutase with Therapeutic Activity in Rats*", Science, 286, October 8, 304-6 (1999).
3. U.S. Pat. No. 8,263,568
4. U.S. Pat. No. 8,444,856
5. Aston, K., Rath, N., Naik, A., Slomczynska, U., Schall, O F., Riley, D. P., "Computer-Aided Design (CAD) of Mn(II) Complexes: Superoxide Dismutase Mimetics with Catalytic Activity Exceeding the Native Enzyme", Inorg. Chem., 40, 1779-89 (2001).

What is claimed is:
1. A pentaaza macrocyclic ring complex corresponding to the following formula:

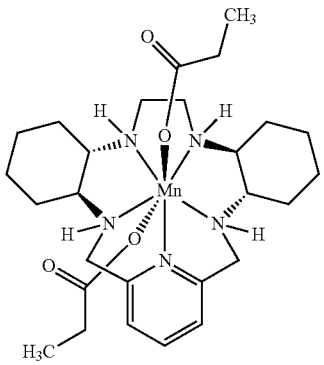

2. A pharmaceutical composition comprising the pentaaza macrocyclic ring complex of claim 1 and a pharmaceutically acceptable excipient.

3. The pharmaceutical composition of claim 2 wherein the composition comprises linoleoyl polyoxyl-6 glycerides (NF).

4. The pharmaceutical composition of claim 2 wherein the pharmaceutical composition is suitable for oral administration to a human subject.

5. The pharmaceutical composition of claim 2 wherein the pharmaceutical composition is in a solid or semi-solid dosage form.

6. The pharmaceutical composition of claim 2 wherein the pharmaceutical composition is in the form of at least one selected from the group consisting of a tablet, gelatin capsule, HPMC capsule, gel and suspension suitable for oral administration.

7. The pharmaceutical composition of claim 2 wherein the pharmaceutical composition comprises an enteric coating layer.

8. A pharmaceutical composition for oral administration comprising:
a pentaaza macrocyclic ring complex corresponding to the following formula:

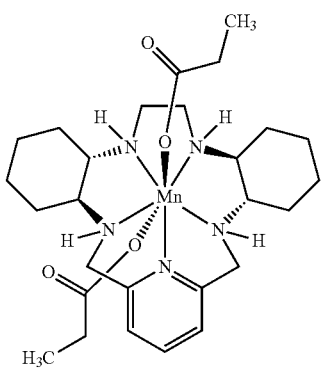

a pharmaceutically acceptable excipient comprising linoleoyl polyoxyl-6 glycerides (NF); and
an enteric coated capsule comprising hydroxypropylmethylcellulose (HPMC),
wherein the capsule comprises the pentaaza macrocyclic ring complex and pharmaceutically acceptable excipient contained therein.

* * * * *